US005962243A

United States Patent [19]
Brown et al.

[11] Patent Number: 5,962,243
[45] Date of Patent: Oct. 5, 1999

[54] METHODS FOR THE IDENTIFICATION OF FARNESYLTRANSFERASE INHIBITORS

[75] Inventors: Michael S. Brown; Joseph L. Goldstein; Guy L. James, all of Dallas, Tex.

[73] Assignee: Board of Regents, The University of Texas System, Austin, Tex.

[21] Appl. No.: 08/429,964

[22] Filed: Apr. 27, 1995

Related U.S. Application Data

[63] Continuation-in-part of application No. 08/021,625, Feb. 16, 1993, which is a continuation-in-part of application No. 07/822,011, Jan. 16, 1992, abandoned, which is a continuation-in-part of application No. 07/937,893, Dec. 22, 1992, which is a continuation of application No. PCT/US91/02650, Apr. 18, 1991, which is a continuation-in-part of application No. 07/615,715, Nov. 20, 1990, Pat. No. 5,141,851, which is a continuation-in-part of application No. 07/510,706, Apr. 18, 1990, abandoned.

[51] Int. Cl.$^6$ .............................. C12Q 1/48; C12N 9/10; C07H 21/04
[52] U.S. Cl. ......................... 435/15; 435/193; 536/23.2
[58] Field of Search ........................... 435/15, 193, 69.1, 435/240.2, 252.3, 320.1; 514/2; 530/329, 330; 536/23.2

[56] References Cited

U.S. PATENT DOCUMENTS

| | | | |
|---|---|---|---|
| 4,677,069 | 6/1987 | Chen et al. | 435/226 |
| 5,026,554 | 6/1991 | Bartizal et al. | 424/404 |
| 5,043,268 | 8/1991 | Stock | 435/15 |
| 5,055,487 | 10/1991 | Bartizal et al. | 514/452 |
| 5,104,975 | 4/1992 | McCormick et al. | 530/350 |
| 5,185,248 | 2/1993 | Barcacid | 435/15 |
| 5,202,456 | 4/1993 | Rando | 558/438 |
| 5,234,849 | 8/1993 | McCormick et al. | 436/501 |
| 5,238,922 | 8/1993 | Graham et al. | 514/18 |
| 5,245,061 | 9/1993 | Singh | 554/121 |
| 5,326,773 | 7/1994 | de Solms et al. | 514/336 |
| 5,340,828 | 8/1994 | Graham et al. | 514/357 |
| 5,352,705 | 10/1994 | Deana et al. | 514/630 |
| 5,443,956 | 8/1995 | Carney | 435/7.23 |
| 5,525,479 | 6/1996 | Anthony et al. | 435/15 |

FOREIGN PATENT DOCUMENTS

| | | |
|---|---|---|
| 0 456 180 | 11/1991 | European Pat. Off. ......... C12N 9/10 |
| 0 461 869 A2 | 12/1991 | European Pat. Off. . |
| 0 520 823 | 12/1992 | European Pat. Off. . |
| 0 523 873 | 1/1993 | European Pat. Off. . |
| 0 528 486 | 2/1993 | European Pat. Off. . |
| 0 535 730 | 4/1993 | European Pat. Off. . |
| 0 535 731 | 4/1993 | European Pat. Off. . |
| 2 261 373 | 5/1993 | United Kingdom . |
| 2 261 374 | 5/1993 | United Kingdom . |
| 2 261 375 | 5/1993 | United Kingdom . |
| WO 91/16340 | 10/1991 | WIPO . |
| WO 94/03597 | 2/1994 | WIPO . |
| WO 94/04561 | 3/1994 | WIPO . |
| WO 94/10184 | 5/1994 | WIPO . |
| WO 95/12572 | 5/1995 | WIPO . |
| WO 96/21456 | 7/1996 | WIPO . |

OTHER PUBLICATIONS

Lacal et al., "Expression of normal and transforming H–ras genes . . . " (1984) PNAS 81:5305.

Anderegg et al., JBC 263:18236 (1988) Structure of Saccharomyces cerevisiae Mating Hormone a–factor : Identification of S–farnesyl cysteine as a structural component.

Towler et al., PNAS 83:2812 (1986) Protein fatty acid acylation: Enzymatic synthesis of an N–myristoylglycyl peptide.

Towler et al., JBC 262:1030 (1987) Amino terminal processing of proteins by N–myristoylation: Substrate specificity of N–myristoyl transferase.

Clark et al., "Posttranslational Modification of the Ha–ras oncogrne Protein: Evidence for a Third Class of Protein Carboxyl Methyltransferases," Proc. Natl. Acad. Sci. USA, 85:4643–4647, 1988.

Hancock et al., "All ras Proteins are Polyisoprenylated but Only come Are Palmitoylated," Cell, 57:1167–77, 1989.

Schafer et al., "Genetic and Pharmacological Suppression of Oncogenic Mutatins in RAS Genes of Yeast and Humans," Science, 245:379–385, 1989.

BOS, "ras Oncogenes in Human Cancer: A Review," Cancer Research, 49:4682–4689, 1989.

Lowy et al., "New Clue to Ras Lipid Glue," Nature, 341:384–85, 1989.

Casey et al., "p21ras Is Modified by a Farnesyl Isoprenoid," Proc. Natl. Acad. Sci. USA, 86:8323–8327, 1989.

Goldstein et al., "Regulation of the Mevalonate Pathway," Nature, 343:425–430, 1990.

Reiss et al., Inhibition of Purified $p21^{ras}$ Farnesyl:Protein Transferase by Cys–AAX Tetrapeptidesanne et al. Cell, 62:81–88, 1990.

Schaber et al., "Polyisoprenylation of Ras in Vitro by a Farnesyl–Protein Transferase," J. Biolog. Chem., 265(25):14701–14704, 1990.

Manne et al., "Identification and Preliminary Characterization of Protein–Cysteine Farnesyltransferase," Proc. Natl. Acad. Sci. USA, 87:7541–7545, 1990.

Reiss et al., "Sequence Requirement for Peptide Recognition by Rat Brain $p21^{ras}$ Protein Farnesyltransferase," Proc. Natl. Acad. Sci. USA, 88:732–736, 1991.

Chen, et al., "cDNA Cloning and Expression of the Peptide–Binding β Subunit of Rat $p21^{ras}$ Farnesyltransferase, the Counterpart of Yeast DPR1/RAM1," Cell, 66:327–334, 1991.

(List continued on next page.)

Primary Examiner—Robert A. Wax
Assistant Examiner—Elizabeth Slobodyansky
Attorney, Agent, or Firm—Arnold White & Durkee

[57] ABSTRACT

Disclosed are methods and compositions for the identification of inhibitors of farnesyltransferase enzymes involved in the prenylation of various cellular proteins, including cancer related ras proteins, such as $p21^{ras}$, particularly, K-rasB. Enclosed are procedures for using purified farnesyltransferase enzymes and K-rasB proteins in screening protocols for the identification of possible anticancer agents that inhibit the enzyme and thereby prevent prenylation of proteins such as K-RasB.

34 Claims, 42 Drawing Sheets

OTHER PUBLICATIONS

Goldstein, et al., "Nonfarnesylated Tetrapeptide Inhibitors of Protein Farnesyltransferase," *J. Biol. Chem.*, 266(24):15575–15578, 1991.

Goodman, et al., "Structure and Expression of Yeast DPR1, a Gene Essential for the Processing and Intracellular Localization of ras Proteins," *Yeast*, 4:271–281, 1988.

Goodman, et al., "Mutants of *Saccharomyces cerevisiae* Defective in the Frnesylation of Ras Proteins," *Proc. Natl. Acad. Sci.*, 87:9665–9669, 1990.

Schaber, et al., "Polyisoprenylation of Ras in Vitro by a Farnesyl–Protein Transferase," *Chem. Abstr.*, 114:302, Abstract # 38170r, 1991.

Kim, et al., "Prenylation of Mammalian Ras Protein in Xenopus Oocytes," *Chem. Abstr.*, 114:373, Abstract # 3711r, 1991.

Kohl et al., "Structural Homology Among Mammalian and *Saccharomyces cerevisiae* Isoprenyl–protein Transferases," *J. Biol. Chem.*, 266(28):18884–18888, 1991.

He et al., "RAM2, an essential gene of yeast, and RAM1 encode the two polypeptide components of the farnesyltransferase that prenylates a–factor and Ras proteins," *PNAS*, 88:11373–11377, 1991.

International Search Report mailed Dec. 9, 1991.

Reiss, et al., "Divalent Cation and Prenyl Pyrophosphate Specificites of the Protein Farnesyltransferase from Rat Brain, a Zinc Metalloenzyme," *J. Biol. Chem.*, 267:6403–6408, 1992. Published in USA.

Seabra, et al., "Protein Farnesyltransferase and Geranylgeranyltransferase Share a Common α Subunit," *Cell*, 65:429–434, 1991. Published in USA.

Reiss, et al., "Purification of ras Farnesyl:Protein Transferase," *Methods: A Companion to Methods in Enzymology*, 1(3):241–245, 1990. Published in USA.

Nancy E. Kohl, et al., "Selective Inhibition of ras–Dependent Transformation by a Farnesyltransferase Inhibitor", *Science*, 260:1934–1937 (1993).

International Search Report, mailed Jan. 24, 1994.

Barbacid, "ras Genes," *Ann. Rev. Biochem*, 56:779–827, 1987.

Capon et al., "Activation of Ki–ras2 gene in human colon and lung carcinomas by two different point mutations," *Nature* 304:507–513, 1983.

Chen et al., "Cloning and expression of a cDNA encoding the α subunit of rat p21$^{ras}$ protein farnesyltransferase," *Proc. Natl. Acad. Sci. USA*, 88:11368–11372, 1991.

Cremers et al., "REP–2, a Rab Escort Protein Encoded by the Choroideremia–like Gene," *The Journal of Biological Chemistry*, 269(3): 2111–2117, 1994.

James et al., "Benzodiazepine Peptidomimetics: Potent Inhibitors of Ras Farnesylation in Animal Cells," *Science*, 260:1937–1942, 1993.

James et al., "Benzodiazepine Peptidomimetic BZA–5B Interrupts the MAP Kinase Activation Pathway in H–Ras–transformed Rat–1 Cells, but Not in Untransformed Cells," *TheJournal of Biological Chemistry*, 269(44):27705–27714, 1994.

McCoy et al., "Human Colon Carcinoma Ki–ras2 Oncogene and Its Corresponding Proto–Oncogene," *Molecular and Cellular Biology*, 4(8):1577–1582, 1984.

McGrath et al., "Structure and organization of the human Ki–ras proto–oncogene and a related processed pseudogene," *Nature*, 304:501–506, 1983.

Shimizu et al., "Structure of the Ki–ras gene of the human lung carcinoma cell line Calu–1," *Nature*, 304:497–500, 1983.

Yokoyama et al., "A protein geranylgeranyltransferase from bovine brain: Implications for protein prenylation specificity," *Proc. Natl. Acad. Sci. USA*, 88:5302–5306, 1991.

Zhang et al., "cDNA Cloning and Expression of Ray and Human Protein Geranylgeranyltransferase Type–I," *The Journal of Biological Chemistry*, 269(5):3175–3180, 1994.

James et al., "Polylysine and CVIM Sequences of K –RasB Dictate Specificity of Prenylation and Confer Resistance to Benzodiazepine Peptidomimetic in vitro," *J. Biol. Chem*, 270(11):6221–6226, 1995.

Reiss et al., "Purification of Ras Farnesyl: Protein Transferase," Methods, 1(3):241–245, 1990.

PCT Search Report mailed Oct. 12, 1996.

PCR Primer α1 →

GA$^T_C$ GCI ATI GA$^A_G$ $^T_C$TA AAC GCA GCC AAC TAT ACG GTC TGG CAC TT (SEQ. ID NO: 57)
Asp Ala Ile Glu Leu Asn Ala Ala Asn Tyr Thr Val Trp His Phe Arg
(SEQ. ID NO: 59)

(SEQ. ID NO: 58) CAI ACC GTA AA$^G_A$ $^G_T$C
← PCR Primer α2

FIG. 16A

RAT FT-α    1  MAATEGVGESAPGGEPGQPEQPPPPPPPPAQQPQEEMAAEAGFAAASP
           51  MDDGFLSLDSPTYVLYRDRAEWADIDPVPQNDGPSPVVQIIYSEKFRDVY
          101  DYERAVLQRDERSERAFKITRDAIELNAANYTVWHFRRVLRSIQKDLQE
          151  EMNYIIAIEEQPKNYQVWHHRVLVEWLKDPS--QELEFIADILNQDAK
          199  NYHAWQHRQWVIQEERLWDNELQYVDQLKEDVRNNSVWNQRHFVISNTT
          249  GYSDRAVLEREMQYTLEMIKLVPHNFSAWNYIKG--IL-QDR--GLSRY
          293  PNLLNQLID-L-QPSHSSPYLIAFLVDIYEDMLENQCDNKEDILNKALEL
          341  CEILAKEKDIIRKEYWRYIGRSLQSKHSRESDIPASV  377  (SEQ. ID NO:1)

FIG. 17

```
Rat FT-β    1  M--ASSSS-----E-TYYCPPSSSPV--WSEPLYSLRPEHARERLQDDSV

41  ETVISIEQAKVEEKIQEVFSSYKFNHLVERLVLQREKHFHYL-KRGLRQLTDAYECLDAS

100  RPWLCYWILHSTELIDEPIPQIVATDVCQFLEL-CQSPDGG-EGGGPGQYPHLAPTYAAV

158  NAL-CIIGTEEAYNVINREKLIDYLYSLKQPDGSE-LMHVGGEVDVRSAYCAASVASLIN

216  IITPDLFEGTAEWIARCONWEGGIGGVP-GMEAHGGYTFCGIAALVILKKERSINLKSLL

275  QWVTSRQMRFEGGFQGRCNKLVDGCYSFWQAGLLPLLHRALHAQGDPALSMSHWMFHQQA

335  LPEYILMCCQ-CPAGGLLDKPGKSRDFYHTQYCISGLSIAQHFGSGAMLHCVVMGVPENV

394  LQFHPVNIGPDK-VIQATTHFL-QKFVPGFEECEDAVISDPATD  437  (SEQ. ID NO: 3)
```

```
GGCGAGATGGCGGCCACCGAGGGGGTCGGGGAGGCTGCGCAAGGGGGGCGAGCCCGGGCAG      60
    MetAlaAlaThrGluGlyValGlyGluAlaAlaAlaGlnGlyGlyGluProGlyGln        18
                                         Ser Pro

CCGGCGCAACCCCCGCCCCCAGCCGCACCCGCGCCCAGCAGCAGCACAAGGAAGAG          120
Pro AlaGlnProProProGlnProHisProProProGlnGlnGlnHisLysGluGlu          38
    Glu              Pro Pro          Ala    ProGlnGlu

ATGGCGGCCGAGGCTGGGGAAGCCGGTGCCCCCCATGGACGACGACGGGTTTGTGAGCCTG    180
MetAlaAlaGluAlaGlyGluAlaGlyAlaProMetAspAspAspGlyPheValSerLeu        58
                            Ala                        Leu

GACTCGCCCCTCCTATGTCCTGTACAGGGACAGAGAGCAGAATGGGCTGATATAGATCCGGTG  240
AspSerProSerTyrValLeuTyrArgAspArgAlaGluTrpAlaAspIleAspProVal        78
          Thr

CCGCAGAATGATGGCCCCAATCCCGTGGTCCAGATCATTTATAGTGACAAATTTAGAGAT    300
ProGlnAsnAspGlyProAsnProValValGlnIleIleTyrSerAspLysPheArgAsp        98
                        Ser                    Glu

GTTTATGATTACTTCCGAGCTGTCCTGCAGCGTGATGAAAGAAGTGAACGAGCTTTTAAG    360
ValTyrAspTyrPheArgAlaValLeuGlnArgAspGluArgSerGluArgAlaPheLys       118
```

FIG. 23A

```
CTAACCCGGGATGCTATTGAGTTAAATGCAGCCAATTATACAGTGTGGCATTTCCGGAGA      420
LeuThrArgAspAlaIleGluLeuAsnAlaAlaAsnTyrThrValTrpHisPheArgArg      138

GTTCTTTTGAAGTCACTTCAGAAGGATCTACATGAGGAAATGAACTACATCACTGCAATA      480
ValLeuLeuLysSerLeuGlnLysAspLeuHisGluMetAsnTyrIleThrAlaIle        158
           Arg               Gln                  Ile

ATTGAGGAGCAGCCCAAAAACTATCAAGTTTGGCATCATAGGCGAGTATTAGTGGAATGG      540
IleGluGluGlnProLysAsnTyrGlnValTrpHisHisArgArgValLeuValGluTrp      178

CTAAGAGATCCATCTCAGGAGCTTGAATTTATTGCTGATATTCTTAATCAGGATGCAAAG      600
LeuArgAspProSerGlnGluLeuGluPheIleAlaAspIleLeuAsnGlnAspAlaLys      198
   Lys

AATTATCATGCCTGGCAGCATGGACAATGGGTTATTCAGGAATTTAAACTTTGGATAAT      660
AsnTyrHisAlaTrpGlnHisArgGlnTrpValIleGlnGluPheLysLeuTrpAspAsn    218
                                       Arg

GAGCTGCAGTATGTGGACCAACTTCTGAAAGAGGATGTGAGAAATAACTCTGTCTGGAAC      720
GluLeuGlnTyrValAspGlnLeuLeuLysGluAspValArgAsnAsnSerValTrpAsn      238

CAAAGATACTTCGTTATTCTAACACCACTGGCTACAATGATCGTGCTGTATTGGAGAGA      780
GlnArgTyrPheValIleSerAsnThrThrGlyTyrAsnAspArgAlaValLeuGluArg     258
      His                            Ser
```

FIG. 23B

```
GAAGTCCAATACACTCTGGAAATGATTAAACTAGTACCACATAATGAAAGTGCATGGAAC  840
GluValGlnTyrThrLeuGluMetIleLysLeuValProHisAsnGluSerAlaTrpAsn  278

TATTTGAAAGGGATTTTGCAGGATCGTGGTCTTTCCAAATATCCTAATCTGTTAAATCAA  900
TyrLeuLysGlyIleLeuGlnAspArgGlyLeuSerLysTyrProAsnLeuLeuAsnGln  298
                                    Arg

TTACTTGATTTACAACCAAGTCATAGTTCCCCCTACCTAATTGCCTTTCTTGTGGATATC  960
LeuLeuAspLeuGlnProSerHisSerSerProTyrLeuIleAlaPheLeuValAspIle  318

TATGAAGACATGCTAGAAAATCAGTGTGACAATAAGGAAGACATTCTTAATAAAGCATTA  1020
TyrGluAspMetLeuGluAsnGlnCysAspAsnLysGluAspIleLeuAsnLysAlaLeu  338

GAGTTATGTGAAATCCTAGCTAAAGAAAAGGACACTATAAGAAAGGAATATTGGAGATAC  1080
GluLeuCysGluIleLeuAlaLysGluLysAspThrIleArgLysGluTyrTrpArgTyr  358

ATTGGAAGATCCCTTCAAAGCAAACACAGCACAGAAAATGACTCACCAACAAATGTACAG  1140
IleGlyArgSerLeuGlnSerLysHisSerThrGluAsnAspSerProThrAsnValGln  378
                              Arg   Ser   Ile   AlaSer   End

CAATAACACCATCCAGAAGAACTTGATGGAATGCTTTTATTTTTTATTAAGGGACCCTGC  1200
Gln(SEQ. ID NO:3)                                             379
```

FIG. 23C

AGGAGTTTCACACGAGAGTGGTCCTTCCCTTGCCTGTGGTGTAAAAGTGCATCACACAG 1260

GTATTGCTTTTAACAAGAACTGATGCTCCTTGGGTGCTGCTACTCAGACTAGCTCT 1320

AAGTAATGTGATTCTTCTAAAGCAAAGTCATTGGATGGGAGGAGGAAGAAAAAGTCCCAT 1380

AAAGGAACTTTTGTAGTCTTATCAACATATAATCTAATCCCTTAGCATCAGCTCCCT 1440

CAGTGGTACATGCGTCAAGATTTGTAGCAGTAATAACTGCAGGTCACTTGTATGTAATGG 1500

ATGTGAGGTAGCCGAAGTTTGGTTCAGTAAGCAGGAATACAGTCGTTCCATCAGAGCTG 1560

GTCTGCACACTCACATTATCTTGCTATCACTGTAACCAACTAATGCCAAAAGAACGGTTT 1620

TGTAATAAAATTATAGCTGTATCTAAAAAAAAAAAAAAAAAAAAAAA (SEQ. ID NO:6) 1670

FIG. 23D

```
GTAGAAGAAAAGATCCAAGAGGTCTTCAGTTCTTACAAGTTCAACCACCTTGTACCAAGG    60
ValGluGluLysIleGlnGluValPheSerSerTyrLysPheAsnHisLeuValProArg    20

CTTGTTTTGCAGAGGGAGAAGCACTTCCATTATCTGAAAAGAGGCCTTGACAACTGACA   120
LeuValLeuGlnArgGluLysHisPheHisTyrLeuLysArgGlyLeuArgGlnLeuThr    40

GATGCCTATGAGTGTCTGGATGCCAGCCGCCCATGGCTCTGCTATTGGATCCTGCACAGC   180
AspAlaTyrGluCysLeuAspAlaSerArgProTrpLeuCysTyrTrpIleLeuHisSer    60

TTGGAACTGCTAGATGAACCCATCCCCCAGATAGTGGCTACAGATGTGTGTCAGTTCCTG   240
LeuGluLeuLeuAspGluProIleProGlnIleValAlaThrAspValCysGlnPheLeu    80

GAGCTGTGTCAGAGCCCAGAAGGTGGCTTTGGAGGAGACCCGGTCAGTATCCACACCTT   300
GluLeuCysGlnSerPro GlyGlyPheGlyGlyGlyProGlyProHisLeu   100
                   Asp

GCACCCACATATGCAGCAGTCAATGCATTGTGCATCATTGGCATCGAGGAGGCCTATGAC   360
AlaProThrTyrAlaAlaValAsnAlaLeuCysIleIleGlyThrGluGluAlaTyrAsp   120
                                                          Asn

ATCATTAACAGAGAGAAGCTTCTTCAGTATTTGTACTCCCTGAAGCAACCTGACGGCTCC   420
IleIleAsnArgGluLysLeuLeuGlnTyrLeuTyrSerLeuLysGlnProAspGlySer   140
Val
```

FIG. 24A

```
TTCTCATGTCGGAGGTGAGGTGGATGTGAGAAGGCATACTGTGCTGCCTCCGTA          480
PheLeuMetHisValGlyGlyGluValAspValArgSerAlaTyrCysAlaAlaSerVal    160

GCCTGCTGACCAACATCATCACTCCAGACCTCTTTGAGGGCACTGCTGAATGGATAGCA    540
AlaSerLeuThrAsnIleIleThrProAspLeuPheGluGlyThrAlaGluTrpIleAla   180

AGGTGTCAGAACTGGGAAGGTGGCATTGGCGGGGTACCAGGGATGGAAGCCATGGTGGC    600
ArgCysGlnAsnTrpGluGlyGlyIleGlyGlyValProGlyMetGluAlaHisGlyGly   200

TATACCTTCTGTGGCCTGGCCGGCTGGTAATCCTCAAGAGGAACGTTCCTTGAACTTG    660
TyrThrPheCysGlyLeuAlaAlaLeuValIleLeuLysArgGluArgSerLeuAsnLeu  220
                                        Lys

AAGAGCTTATTACAATGGGTGACAAGCCGGCAGATGCTATTTGAAGGAGGATTTCAGGGC   720
LysSerLeuLeuGlnTrpValThrSerArgGlnMetLeuPheGluGlyGlyPheGlnGly  240
                                    Arg

CGCTGCAACAAGCTGGTGGATGGCTGCTACTCCTTCTGGCAGGCGGGGCTCCTGCCCCTG   780
ArgCysAsnLysLeuValAspGlyCysTyrSerPheTrpGlnAlaGlyLeuLeuProLeu  260

CTCCACCGCGCACTGCACGCCCAAGGTGACCCTGCCCTTAGCATGAGCCACTGGATGTTC   840
LeuHisArgAlaLeuHisAlaGlnGlyAspProAlaLeuSerMetSerHisTrpMetPhe  280
```

FIG. 24B

```
CATCAGCAGGCCCTGCAGGAGTACATCCTGATGTGCTGCCAGTGCCCTGCGGGGGGCTT      900
HisGlnAlaLeuGlnGluTyrIleLeuMetCysCysGlnCysProAlaGlyGlyLeu        300

CTGGATAAACCTGGCAAGTCGCGTGATTTCTACCACACCTGCTACTGCCTGAGCGGCCTG     960
LeuAspLysProGlyLysSerArgAspPheTyrHisThrCysTyrCysLeuSerGlyLeu     320

TCCATAGCCCAGCACTTCGGCAGGGAGCCATGTTGCATGATGGTCCTGGGTGTGCCC        1020
SerIleAlaGlnHisPheGlySerGlyAlaMetLeuHisAspValVal LeuGlyValPro     340
                                                 Met

GAAAACGCTCTGCAGCCCACTCACCCAGTGTACAACATTGGACCAGACAAGGTGATCCAG     1080
GluAsnAlaLeuGlnProThrHisProValTyrAsnIleGlyProAspLysValIleGln     360
         Val

GCCACTACATACTTTCTACAGAAGCCAGTCCCAGGTTTTGAGGAGCTTAAGGATGAGACA     1140
AlaThrThr Tyr PheLeuGlnLysProGlyPheGluGlu LeuLysAspGluThr         380
          His                             CysGlu    AlaVal

TCGGCAGAGCCTGCAACCGACTAGAGAGGACCTGGGTCCCGGCAGCTCTTTGCTCACCCATC  1200
SerAlaGluProAlaThrAsp       (SEQ. ID NO:7)                       387
ThrSerAsp

TCCCCAGTCAGACAAGGTTTATAGGTTTCAATACATACTGCATTCTGT    (SEQ. ID NO:8)  1248
```

FIG. 24C

| Protein | COOH-Terminal Sequence | SEQ ID NO |
|---|---|---|
| H-Ras | D E S G P G C M S C K C V L S | SEQ ID NO: 72 |
| K-RasB | K K K K K K S K T K C V I M | SEQ ID NO: 73 |
| H-Ras CVIM | D E S G P G C M S C K C V I M | SEQ ID NO: 74 |
| H-Ra(K$_n$)CVLS | K K K K K K S K T K C V L S | SEQ ID NO: 75 |
| H-Ras(K$_n$)CVIM | K K K K K K S K T K C V I M | SEQ ID NO: 73 |
| Rap1B | P V P G K A R K K S S C Q L L | SEQ ID NO: 76 |

FIG. 25

| Wild-type Ras | $I_{0.5}$(nM) |
|---|---|
| △ H-RasCVLS | 1.6 |
| ■ H-RasB | 13 |
| Chimeric Ras | |
| ▲ H-Ras($K_n$)CVLS | 1.6 |
| ◐ H-RasCVIM | 1.6 |
| ◨ H-Ras($K_n$)CVIM | 13 |

5,962,243

SEQUENCE LISTING (1) GENERAL INFORMATION:

(iii) NUMBER OF SEQUENCES: 85

(2) INFORMATION FOR SEQ ID NO:1:

(i) SEQUENCE CHARACTERISTICS:
      (A) LENGTH: 377 amino acids
      (B) TYPE: amino acid
      (C) STRANDEDNESS: single
      (D) TOPOLOGY: linear (xi) SEQUENCE DESCRIPTION: SEQ ID NO:1:

```
Met Ala Ala Thr Glu Gly Val Gly Glu Ser Ala Pro Gly Gly Glu Pro
1               5                   10                  15

Gly Gln Pro Glu Gln Pro Pro Pro Pro Pro Pro Pro Ala Gln
            20              25                  30

Gln Pro Gln Glu Glu Glu Met Ala Ala Glu Ala Gly Glu Ala Ala Ala
        35                  40                  45

Ser Pro Met Asp Asp Gly Phe Leu Ser Leu Asp Ser Pro Thr Tyr Val
    50                  55                  60

Leu Tyr Arg Asp Arg Ala Glu Trp Ala Asp Ile Asp Pro Val Pro Gln
65                  70                  75                  80

Asn Asp Gly Pro Ser Pro Val Val Gln Ile Ile Tyr Ser Glu Lys Phe
                85                  90                  95

Arg Asp Val Tyr Asp Tyr Phe Arg Ala Val Leu Gln Arg Asp Glu Arg
            100                 105                 110

Ser Glu Arg Ala Phe Lys Leu Thr Arg Asp Ala Ile Glu Leu Asn Ala
        115                 120                 125

Ala Asn Tyr Thr Val Trp His Phe Arg Arg Val Leu Leu Arg Ser Leu
    130                 135                 140

Gln Lys Asp Leu Gln Glu Glu Met Asn Tyr Ile Ile Ala Ile Ile Glu
145                 150                 155                 160

Glu Gln Pro Lys Asn Tyr Gln Val Trp His His Arg Arg Val Leu Val
                165                 170                 175

Glu Trp Leu Lys Asp Pro Ser Gln Glu Leu Glu Phe Ile Ala Asp Ile
            180                 185                 190

Leu Asn Gln Asp Ala Lys Asn Tyr His Ala Trp Gln His Arg Gln Trp
```

```
                       195                   200                   205
Val Ile Gln Glu Phe Arg Leu Trp Asp Asn Glu Leu Gln Tyr Val Asp
    210                 215                 220

Gln Leu Lys Glu Asp Val Arg Asn Asn Ser Val Trp Asn Gln Arg
225                 230                 235                 240

His Phe Val Ile Ser Asn Thr Thr Gly Tyr Ser Asp Arg Ala Val Leu
                245                 250                 255

Glu Arg Glu Val Gln Tyr Thr Leu Glu Met Ile Lys Leu Val Pro His
                260                 265                 270

Asn Glu Ser Ala Trp Asn Tyr Leu Lys Gly Ile Leu Gln Asp Arg Gly
            275                 280                 285

Leu Ser Arg Tyr Pro Asn Leu Leu Asn Gln Leu Leu Asp Leu Gln Pro
290                 295                 300

Ser His Ser Ser Pro Tyr Leu Ile Ala Phe Leu Val Asp Ile Tyr Glu
305                 310                 315                 320

Asp Met Leu Glu Asn Gln Cys Asp Asn Lys Glu Asp Ile Leu Asn Lys
                325                 330                 335

Ala Leu Glu Leu Cys Glu Ile Leu Ala Lys Glu Lys Asp Thr Ile Arg
                340                 345                 350

Lys Glu Tyr Trp Arg Tyr Ile Gly Arg Ser Leu Gln Ser Lys His Ser
                355                 360                 365

Arg Glu Ser Asp Ile Pro Ala Ser Val
370                 375

(2) INFORMATION FOR SEQ ID NO:2:

(i) SEQUENCE CHARACTERISTICS:
        (A) LENGTH: 1701 base pairs
        (B) TYPE: nucleic acid
        (C) STRANDEDNESS: single
        (D) TOPOLOGY: linear (xi) SEQUENCE DESCRIPTION: SEQ ID NO:2:

GCGGGCCGCG GAGGGGGCGG GGCTCCACCA CCACCTCAGC TGCGGACGGA GGCGAGATGG      60

CGGCCACTGA GGGGGTCGGG GAATCTGCGC CAGGCGGTGA GCCGGGACAG CCAGAGCAGC    120

CGCCGCCCCC GCCTCCTCCG CCGCCAGCAC AGCAGCCGCA GGAAGAAGAG ATGGCGGCCG    180

AGGCCGGGGA AGCAGCGGCG TCCCCTATGG ACGACGGGTT TCTGAGCCTG GACTCGCCCA    240

CCTATGTCTT GTACAGGGAC AGGGCAGAGT GGGCTGACAT AGACCCAGTG CCCCAGAATG    300

ATGGCCCCAG TCCAGTGGTC CAGATCATCT ACAGTGAAAA GTTTAGAGAC GTCTATGATT    360

ACTTCCGAGC TGTTCTGCAG CGCGATGAAA GAAGCGAACG AGCCTTTAAG CTCACTCGAG    420

ATGCTATTGA GTTAAACGCA GCCAACTATA CGGTGTGGCA TTTTCGGAGA GTTCTCTTGA    480

GGTCGCTTCA GAAGGATCTG CAAGAAGAAA TGAACTACAT CATCGCAATA ATTGAGGAAC    540

AGCCCAAAAA CTATCAAGTT TGGCACCATA GGAGAGTATT AGTGGAGTGG CTGAAAGATC    600

CTTCTCAAGA GCTCGAGTTC ATCGCCGATA TCCTTAATCA GGATGCAAAG AATTACCATG    660

CCTGGCAGCA TCGACAGTGG GTCATTCAGG AGTTTCGACT TTGGGATAAT GAGCTGCAGT    720

ATGTGGACCA GCTTCTCAAA GAGGATGTGA GAAATAACTC TGTGTGGAAC CAAAGACACT    780

TCGTCATTTC TAATACCACT GGCTACAGTG ATCGCGCTGT GTTGGAGAGA GAAGTCCAAT    840

ATACTCTGGA AATGATCAAA TTAGTGCCAC ACAATGAGAG TGCGTGGAAC TACTTGAAAG    900

GGATTTTGCA GGACCGTGGT CTTTCCAGAT ACCCTAATCT ATTAAACCAG TTGCTTGATT    960

TACAACCAAG TCACAGCTCC CCCTACCTAA TTGCCTTTCT TGTGGATATC TATGAAGACA   1020
```

-continued

```
TGCTGGAAAA CCAGTGTGAC AACAAGGAGG ACATTCTTAA TAAAGCACTA GAGTTATGTG      1080

AGATTCTAGC TAAAGAAAAG GACACTATAA GAAAGGAATA TTGGAGATAT ATTGGACGGT      1140

CCCTCCAGAG TAAACACAGC AGAGAAAGTG ACATACCGGC GAGTGTATAG CAGCAAGAGC      1200

GGCTGGAAGA AGTGGACAAT GCTTTCTAAG GCCTCTTATT CGGGAGTGTA GAGCGGTTAG      1260

AGCGGTCATC TCATGCCTGT GAGCTAACGT TGTCCAGGTG CTGTTTCTAA CAAGAACTAA      1320

GGATGACTCC TGTGTCTGAC GCTGTTCAGA CTAGCTAAGA GTCGATTTCC TAAAGCAAGG      1380

TCATTGGAGG GGAGGGTGAA GAAAACTTTC CCGTAAAGGA ACTACTGCTT TTGTAGTCTT      1440

CCCAACATTT AATCCAATCC TGTAGAATCA GCATCTCCTG AAAGACATGG TGCACGGCTG      1500

TGTGCTGGGC GTGGCTAAGG GCAGCTGTGT CATGGGTTTG CAGTCATGGG AACCTCGGAG      1560

CGCTGCCCGG GACTGCATTG ATGATTAGGG CTGCTGGCCT CACCCACAGG ATCTTGCTAT      1620

CACTGTAACC AACTAATGCC AAAAGAAAGG TTTTATAATA AAATCACATT ATCTACAAAC      1680

AAAAAAAAAA AAAAAAAAA A                                                1701
```

(2) INFORMATION FOR SEQ ID NO:3:

(i) SEQUENCE CHARACTERISTICS:
        (A) LENGTH: 437 amino acids
        (B) TYPE: amino acid
        (C) STRANDEDNESS: single
        (D) TOPOLOGY: linear (xi) SEQUENCE DESCRIPTION: SEQ ID NO:3:

```
Met Ala Ser Ser Ser Phe Thr Tyr Tyr Cys Pro Pro Ser Ser Ser
  1               5                  10                  15

Pro Val Trp Ser Glu Pro Leu Tyr Ser Leu Arg Pro Glu His Ala Arg
                 20                  25                  30

Glu Arg Leu Gln Asp Asp Ser Val Glu Thr Val Thr Ser Ile Glu Gln
             35                  40                  45

Ala Lys Val Glu Glu Lys Ile Gln Glu Val Phe Ser Ser Tyr Lys Phe
         50                  55                  60

Asn His Leu Val Pro Arg Leu Val Leu Gln Arg Glu Lys His Phe His
 65                  70                  75                  80

Tyr Leu Lys Arg Gly Leu Arg Gln Leu Thr Asp Ala Tyr Glu Cys Leu
                 85                  90                  95

Asp Ala Ser Arg Pro Trp Leu Cys Tyr Trp Ile Leu His Ser Leu Glu
            100                 105                 110

Leu Leu Asp Glu Pro Ile Pro Gln Ile Val Ala Thr Asp Val Cys Gln
        115                 120                 125

Phe Leu Glu Leu Cys Gln Ser Pro Asp Gly Gly Phe Gly Gly Gly Pro
    130                 135                 140

Gly Gln Tyr Pro His Leu Ala Pro Thr Tyr Ala Ala Val Asn Ala Leu
145                 150                 155                 160

Cys Ile Ile Gly Thr Glu Glu Ala Tyr Asn Val Ile Asn Arg Glu Lys
                165                 170                 175

Leu Leu Gln Tyr Leu Tyr Ser Leu Lys Gln Pro Asp Gly Ser Phe Leu
            180                 185                 190

Met His Val Gly Gly Glu Val Asp Val Arg Ser Ala Tyr Cys Ala Ala
        195                 200                 205

Ser Val Ala Ser Leu Thr Asn Ile Ile Thr Pro Asp Leu Phe Glu Gly
    210                 215                 220

Thr Ala Glu Trp Ile Ala Arg Cys Gln Asn Trp Glu Gly Gly Ile Gly
225                 230                 235                 240
```

```
Gly Val Pro Gly Met Glu Ala His Gly Gly Tyr Thr Phe Cys Gly Leu
                245                 250                 255

Ala Ala Leu Val Ile Leu Lys Lys Glu Arg Ser Leu Asn Leu Lys Ser
            260                 265                 270

Leu Leu Gln Trp Val Thr Ser Arg Gln Met Arg Phe Glu Gly Gly Phe
                275                 280                 285

Gln Gly Arg Cys Asn Lys Leu Val Asp Gly Cys Tyr Ser Phe Trp Gln
290                 295                 300

Ala Gly Leu Leu Pro Leu Leu His Arg Ala Leu His Ala Gln Gly Asp
305                 310                 315                 320

Pro Ala Leu Ser Met Ser His Trp Met Phe His Gln Gln Ala Leu Gln
                325                 330                 335

Glu Tyr Ile Leu Met Cys Cys Gln Cys Pro Ala Gly Gly Leu Leu Asp
                340                 345                 350

Lys Pro Gly Lys Ser Arg Asp Phe Tyr His Thr Cys Tyr Cys Leu Ser
                355                 360                 365

Gly Leu Ser Ile Ala Gln His Phe Gly Ser Gly Ala Met Leu His Asp
            370                 375                 380

Val Val Met Gly Val Pro Glu Asn Val Leu Gln Pro Thr His Pro Val
385                 390                 395                 400

Tyr Asn Ile Gly Pro Asp Lys Val Ile Gln Ala Thr Thr His Phe Leu
                405                 410                 415

Gln Lys Pro Val Pro Gly Phe Glu Glu Cys Glu Asp Ala Val Thr Ser
                420                 425                 430

Asp Pro Ala Thr Asp
            435

(2) INFORMATION FOR SEQ ID NO:4:

(i) SEQUENCE CHARACTERISTICS:
        (A) LENGTH: 2464 base pairs
        (B) TYPE: nucleic acid
        (C) STRANDEDNESS: single
        (D) TOPOLOGY: linear (xi) SEQUENCE DESCRIPTION: SEQ ID NO:4:

CGGGCGCGTT GTTGCTGGAC GAAGCTGAGT CCTATACAGC GCTCGCAGCT CTCCCGATCA     60

TGGCTTCTTC GAGTTCCTTC ACCTATTATT GTCCTCCATC TTCTTCCCCT GTTTGGTCAG    120

AACCGCTGTA TAGTCTGAGA CCTGAGCACG CGCGGGAGCG GTTGCAAGAC GACTCAGTGG    180

AAACAGTCAC GTCCATAGAA CAGGCCAAAG TAGAAGAAAA GATCCAGGAG GTCTTCAGTT    240

CTTACAAGTT TAACCACCTC GTACCAAGGC TCGTTCTGCA GAGGGAGAAG CACTTCCATT    300

ATCTGAAAAG AGGCCTTCGA CAACTGACAG ATGCCTATGA GTGTCTGGAT GCCAGCCGCC    360

CCTGGCTCTG CTACTGGATC CTGCACAGCT TGGAGCTCCT CGACGAACCC ATCCCCCAAA    420

TAGTGGCTAC AGATGTGTGT CAGTTCTTGG AGCTGTGTCA GAGTCCAGAC GGTGGCTTTG    480

GAGGGGGCCC TGGTCAGTAC CCACACCTCG CTCCCACGTA TGCAGCTGTC AACGCGCTAT    540

GCATCATTGG CACGGAGGAA GCCTACAACG TCATTAACAG AGAGAAGCTC CTTCAGTACT    600

TGTACTCCCT AAAGCAACCG GATGGCTCTT TTCTCATGCA CGTCGGAGGA GAGGTGGATG    660

TAAGAAGTGC GTACTGTGCT GCCTCAGTAG CCTCTCTCAC CAACATCATC ACTCCTGACC    720

TCTTCGAAGG CACTGCTGAA TGGATAGCAA GGTGCCAGAA CTGGGAAGGC GGCATTGGCG    780

GGGTGCCAGG GATGGAAGCC CACGGTGGCT ACACCTTCTG TGGCTTGGCT GCGCTGGTGA    840

TCCTCAAGAA GGAACGTTCT TTGAACCTGA AGAGCTTGCT ACAATGGGTG ACAAGCCGGC    900
```

```
AGATGCGGTT CGAAGGAGGA TTTCAGGGCC GCTGCAACAA GCTGGTGGAC GGCTGCTACT    960

CCTTCTGGCA GGCAGGACTT CTGCCCCTGT TGCACCGGGC ACTCCACGCT CAAGGTGACC   1020

CTGCCCTCAG CATGAGCCAC TGGATGTTCC ATCAGCAGGC GCTGCAGGAG TACATCCTCA   1080

TGTGCTGCCA GTGTCCGGCT GGGGGTCTCC TGGACAAACC TGGCAAGTCA CGTGACTTCT   1140

ACCATACTTG CTACTGCCTG AGCGGCCTGT CCATTGCCCA GCATTTTGGA AGTGGAGCCA   1200

TGCTGCACGA TGTGGTCATG GGTGTGCCTG AAAATGTTCT GCAGCCCACT CACCCTGTGT   1260

ACAACATCGG ACCTGATAAG GTGATCCAGG CCACCACACA CTTTCTGCAG AAGCCGGTCC   1320

CAGGCTTTGA GGAATGCGAA GATGCGGTGA CCTCAGATCC TGCCACTGAC TAGAGGACCC   1380

CATGGCTCCC CCAAATCCCC CGTCAGACAA GGTTTCTCCG TTTGGGTACA TAGCACAGTC   1440

CGTGCTACTT GAGCCTTGGC CACTGTGGAG TTGTGGTTTC TTTGTCCTTT CCTGTCAAAC   1500

AAAACAAAGC CATCAGCTCT GGGTTGGAAT ACACAATGGT GTGATTTTTA AAATTATTTT   1560

CATACCTGTC AAACCAAAAC TCTGGGAGCC GATGTAGTAA GCAGGGTTGG AGAGCAATGC   1620

ATGCTGGGAA GCAGCAGCCT CCTCCAGCAG CCAGGCCCAC AATGCTGAAA TGGAAGGTGT   1680

CTGTGAGTAT CTCCACATCA CAGCCACTGC TGTGCCTCCC ACCTACACAC CATTCAGTCA   1740

GCAGATGGGC TCCTCTCTGG TATAAATGTC AGCTCTGTGC AAGGGCGGCG CTGTGGGTCC   1800

AGCCAATACA CGCTCTCTGG AAAACAGCAC TGGGCTCCAG TGGGCATATT CATACTTGTC   1860

TCTTTTACCC CAGTCATTTG CGAAGGACAG GGGCCAGGAA TGAAGAAGGG TCTTAGATTG   1920

AGCCCTCCCC ACAACCTGAG GAGAACTGAT CTCATATTTC TCCAAGGCCA TGTTTGTATG   1980

AGCAAGACTT GTTTTGCCCT AAGTATGACG ACTAGACCCA GGTAATCAAT TATGAGTGGA   2040

AAATCAACCT CTAGGTGAAC TCTGTGCCAG AGGAAGCAGC CTCCCCAGTG TCCAGCCCCC   2100

GCCTCTCCCC ATCATGTACC AGGAGAGGCC CTCCTCACGG CAGTGCTGCA GCCCAGGCTC   2160

CTTCTAGTCC TTTCTCCCCA CCCACCCTCC AAGCACAGTC TCTTTTCTCA TCCAGGGTGT   2220

TAACACTACT AAGGCTTCAC CGTAATCGAT CACTCAGGAT TTACTCCTGC CCTGCCCACT   2280

CCAGGCTCTC TGAAACACAG TCAAGTGCTA GGCAAGCTAG CTGCTGCTGG ACAGTGACC   2340

AGCAGGAAGG CAAGTGCTGT CCGTGTGCTG AATTCTGGAA CTGCCTCTGC ACCGGCTGAG   2400

TTTGCTCACC TATCCACTGC TACAGTCATA GCAAGCTCAT GCCGCTGTCC CAGCCTGTGC   2460

GAGC                                                               2464
```

(2) INFORMATION FOR SEQ ID NO:5:

(i) SEQUENCE CHARACTERISTICS:
    (A) LENGTH: 379 amino acids
    (B) TYPE: amino acid
    (C) STRANDEDNESS: single
    (D) TOPOLOGY: linear (xi) SEQUENCE DESCRIPTION: SEQ ID NO:5:

```
Met Ala Ala Thr Glu Gly Val Gly Glu Ala Ala Gln Gly Gly Glu Pro
 1               5                  10                  15

Gly Gln Pro Ala Gln Pro Pro Gln Pro His Pro Pro Pro Gln
            20                  25                  30

Gln Gln His Lys Glu Glu Met Ala Ala Glu Ala Gly Glu Ala Val Ala
        35                  40                  45

Ser Pro Met Asp Asp Gly Phe Val Ser Leu Asp Ser Pro Ser Tyr Val
    50                  55                  60

Leu Tyr Arg Asp Arg Ala Glu Trp Ala Asp Ile Asp Pro Val Pro Gln
65                  70                  75                  80
```

```
Asn Asp Gly Pro Asn Pro Val Val Gln Ile Ile Tyr Ser Asp Lys Phe
                85                  90                  95

Arg Asp Val Tyr Asp Tyr Phe Arg Ala Val Leu Gln Arg Asp Glu Arg
            100                 105                 110

Ser Glu Arg Ala Phe Lys Leu Thr Arg Asp Ala Ile Glu Leu Asn Ala
        115                 120                 125

Ala Asn Tyr Thr Val Trp His Phe Arg Arg Val Leu Leu Lys Ser Leu
    130                 135                 140

Gln Lys Asp Leu His Glu Glu Met Asn Tyr Ile Thr Ala Ile Ile Glu
145                 150                 155                 160

Glu Gln Pro Lys Asn Tyr Gln Val Trp His His Arg Arg Val Leu Val
                165                 170                 175

Glu Trp Leu Arg Asp Pro Ser Gln Glu Leu Glu Phe Ile Ala Asp Ile
            180                 185                 190

Leu Asn Gln Asp Ala Lys Asn Tyr His Ala Trp Gln His Arg Gln Trp
        195                 200                 205

Val Ile Gln Glu Phe Lys Leu Trp Asp Asn Glu Leu Gln Tyr Val Asp
    210                 215                 220

Gln Leu Leu Lys Glu Asp Val Arg Asn Asn Ser Val Trp Asn Gln Arg
225                 230                 235                 240

Tyr Phe Val Ile Ser Asn Thr Thr Gly Tyr Asn Asp Arg Ala Val Leu
                245                 250                 255

Glu Arg Glu Val Gln Tyr Thr Leu Glu Met Ile Lys Leu Val Pro His
            260                 265                 270

Asn Glu Ser Ala Trp Asn Tyr Leu Lys Gly Ile Leu Gln Asp Arg Gly
        275                 280                 285

Leu Ser Lys Tyr Pro Asn Leu Leu Asn Gln Leu Leu Asp Leu Gln Pro
    290                 295                 300

Ser His Ser Ser Pro Tyr Leu Ile Ala Phe Leu Val Asp Ile Tyr Glu
305                 310                 315                 320

Asp Met Leu Glu Asn Gln Cys Asp Asn Lys Glu Asp Ile Leu Asn Lys
                325                 330                 335

Ala Leu Glu Leu Cys Glu Ile Leu Ala Lys Glu Lys Asp Thr Ile Arg
            340                 345                 350

Lys Glu Tyr Trp Arg Tyr Ile Gly Arg Ser Leu Gln Ser Lys His Ser
        355                 360                 365

Thr Glu Asn Asp Ser Pro Thr Asn Val Gln Gln
    370                 375

(2) INFORMATION FOR SEQ ID NO:6:

(i) SEQUENCE CHARACTERISTICS:
        (A) LENGTH: 1664 base pairs
        (B) TYPE: nucleic acid
        (C) STRANDEDNESS: single
        (D) TOPOLOGY: linear (xi) SEQUENCE DESCRIPTION: SEQ ID NO:6:

ATGGCGGCCA CCGAGGGGGT CGGGGAGGCT GCGCAAGGGG GCGAGCCCGG GCAGCCGGCG    60

CAACCCCCGC CCCAGCCGCA CCCACCGCCG CCCCAGCAGC AGCACAAGGA AGAGATGGCG   120

GCCGAGGCTG GGAAGCCGT GGCGTCCCCC ATGGACGACG GGTTTGTGAG CCTGGACTCG   180

CCCTCCTATG TCCTGTACAG GGACAGAGCA GAATGGGCTG ATATAGATCC GGTGCCGCAG   240

AATGATGGCC CCAATCCCGT GGTCCAGATC ATTTATAGTG ACAAATTTAG AGATGTTTAT   300

GATTACTTCC GAGCTGTCCT GCAGCGTGAT GAAAGAAGTG AACGAGCTTT TAAGCTAACC   360
```

```
CGGGATGCTA TTGAGTTAAA TGCAGCCAAT TATACAGTGT GGCATTTCCG GAGAGTTCTT      420

TTGAAGTCAC TTCAGAAGGA TCTACATGAG GAAATGAACT ACATCACTGC AATAATTGAG      480

GAGCAGCCCA AAAACTATCA AGTTTGGCAT CATAGGCGAG TATTAGTGGA ATGGCTAAGA      540

GATCCATCTC AGGAGCTTGA ATTTATTGCT GATATTCTTA ATCAGGATGC AAAGAATTAT      600

CATGCCTGGC AGCATCGACA ATGGGTTATT CAGGAATTTA AACTTTGGGA TAATGAGCTG      660

CAGTATGTGG ACCAACTTCT GAAAGAGGAT GTGAGAAATA ACTCTGTCTG GAACCAAAGA      720

TACTTCGTTA TTTCTAACAC CACTGGCTAC AATGATCGTG CTGTATTGGA GAGAGAAGTC      780

CAATACACTC TGGAAATGAT TAAACTAGTA CCACATAATG AAAGTGCATG GAACTATTTG      840

AAAGGGATTT TGCAGGATCG TGGTCTTTCC AAATATCCTA ATCTGTTAAA TCAATTACTT      900

GATTTACAAC CAAGTCATAG TTCCCCCTAC CTAATTGCCT TTCTTGTGGA TATCTATGAA      960

GACATGCTAG AAAATCAGTG TGACAATAAG GAAGACATTC TTAATAAAGC ATTAGAGTTA     1020

TGTGAAATCC TAGCTAAAGA AAAGGACACT ATAAGAAAGG AATATTGGAG ATACATTGGA     1080

AGATCCCTTC AAAGCAAACA CAGCACAGAA AATGACTCAC CAACAAATGT ACAGCAATAA     1140

CACCATCCAG AAGAACTTGA TGGAATGCTT TTATTTTTTA TTAAGGGACC CTGCAGGAGT     1200

TTCACACGAG AGTGGTCCTT CCCTTTGCCT GTGGTGTAAA AGTGCATCAC ACAGGTATTG     1260

CTTTTTAACA AGAACTGATG CTCCTTGGGT GCTGCTGCTA CTCAGACTAG CTCTAAGTAA     1320

TGTGATTCTT CTAAAGCAAA GTCATTGGAT GGGAGGAGGA AGAAAAGTC CCATAAAGGA      1380

ACTTTTGTAG TCTTATCAAC ATATAATCTA ATCCCTTAGC ATCAGCTCCT CCCTCAGTGG     1440

TACATGCGTC AAGATTTGTA GCAGTAATAA CTGCAGGTCA CTTGTATGTA ATGGATGTGA     1500

GGTAGCCGAA GTTTGGTTCA GTAAGCAGGG AATACAGTCG TTCCATCAGA GCTGGTCTGC     1560

ACACTCACAT TATCTTGCTA TCACTGTAAC CAACTAATGC CAAAAGAACG GTTTTGTAAT     1620

AAAATTATAG CTGTATCTAA AAAAAAAAAA AAAAAAAAA AAAA                       1664
```

(2) INFORMATION FOR SEQ ID NO:7:

(i) SEQUENCE CHARACTERISTICS:
        (A) LENGTH: 387 amino acids
        (B) TYPE: amino acid
        (C) STRANDEDNESS: single
        (D) TOPOLOGY: linear (xi) SEQUENCE DESCRIPTION: SEQ ID NO:7:

```
Val Glu Glu Lys Ile Gln Glu Val Phe Ser Ser Tyr Lys Phe Asn His
 1               5                  10                  15

Leu Val Pro Arg Leu Val Leu Gln Arg Glu Lys His Phe His Tyr Leu
                20                  25                  30

Lys Arg Gly Leu Arg Gln Leu Thr Asp Ala Tyr Glu Cys Leu Asp Ala
            35                  40                  45

Ser Arg Pro Trp Leu Cys Tyr Trp Ile Leu His Ser Leu Glu Leu Leu
        50                  55                  60

Asp Glu Pro Ile Pro Gln Ile Val Ala Thr Asp Val Cys Gln Phe Leu
65                  70                  75                  80

Glu Leu Cys Gln Ser Pro Glu Gly Gly Phe Gly Gly Pro Gly Gln
                85                  90                  95

Tyr Pro His Leu Ala Pro Thr Tyr Ala Ala Val Asn Ala Leu Cys Ile
                100                 105                 110

Ile Gly Thr Glu Glu Ala Tyr Asp Ile Ile Asn Arg Glu Lys Leu Leu
            115                 120                 125

Gln Tyr Leu Tyr Ser Leu Lys Gln Pro Asp Gly Ser Phe Leu Met His
```

```
                130                 135                 140
Val Gly Gly Glu Val Asp Val Arg Ser Ala Tyr Cys Ala Ala Ser Val
145                 150                 155                 160

Ala Ser Leu Thr Asn Ile Ile Thr Pro Asp Leu Phe Glu Gly Thr Ala
                165                 170                 175

Glu Trp Ile Ala Arg Cys Gln Asn Trp Glu Gly Gly Ile Gly Gly Val
                180                 185                 190

Pro Gly Met Glu Ala His Gly Gly Tyr Thr Phe Cys Gly Leu Ala Ala
                195                 200                 205

Leu Val Ile Leu Lys Arg Glu Arg Ser Leu Asn Leu Lys Ser Leu Leu
210                 215                 220

Gln Trp Val Thr Ser Arg Gln Met Leu Phe Glu Gly Gly Phe Gln Gly
225                 230                 235                 240

Arg Cys Asn Lys Leu Val Asp Gly Cys Tyr Ser Phe Trp Gln Ala Gly
                245                 250                 255

Leu Leu Pro Leu Leu His Arg Ala Leu His Ala Gln Gly Asp Pro Ala
                260                 265                 270

Leu Ser Met Ser His Trp Met Phe His Gln Ala Leu Gln Glu Tyr
                275                 280                 285

Ile Leu Met Cys Cys Gln Cys Pro Ala Gly Gly Leu Leu Asp Lys Pro
                290                 295                 300

Gly Lys Ser Arg Asp Phe Tyr His Thr Cys Tyr Cys Leu Ser Gly Leu
305                 310                 315                 320

Ser Ile Ala Gln His Phe Gly Ser Gly Ala Met Leu His Asp Val Val
                325                 330                 335

Leu Gly Val Pro Glu Asn Ala Leu Gln Pro Thr His Pro Val Tyr Asn
                340                 345                 350

Ile Gly Pro Asp Lys Val Ile Gln Ala Thr Thr Tyr Phe Leu Gln Lys
                355                 360                 365

Pro Val Pro Gly Phe Glu Glu Leu Lys Asp Glu Thr Ser Ala Glu Pro
                370                 375                 380

Ala Thr Asp
385

(2) INFORMATION FOR SEQ ID NO:8:

(i) SEQUENCE CHARACTERISTICS:
        (A) LENGTH: 1248 base pairs
        (B) TYPE: nucleic acid
        (C) STRANDEDNESS: single
        (D) TOPOLOGY: linear (xi) SEQUENCE DESCRIPTION: SEQ ID NO:8:

GTAGAAGAAA AGATCCAAGA GGTCTTCAGT TCTTACAAGT TCAACCACCT TGTACCAAGG      60

CTTGTTTTGC AGAGGGAGAA GCACTTCCAT TATCTGAAAA GAGGCCTTCG ACAACTGACA     120

GATGCCTATG AGTGTCTGGA TGCCAGCCGC CCATGGCTCT GCTATTGGAT CCTGCACAGC     180

TTGGAACTGC TAGATGAACC CATCCCCCAG ATAGTGGCTA CAGATGTGTG TCAGTTCCTG     240

GAGCTGTGTC AGAGCCCAGA AGGTGGCTTT GGAGGAGGAC CCGGTCAGTA TCCACACCTT     300

GCACCCACAT ATGCAGCAGT CAATGCATTG TGCATCATTG CACCGAGGA GGCCTATGAC     360

ATCATTAACA GAGAGAAGCT TCTTCAGTAT TTGTACTCCC TGAAGCAACC TGACGGCTCC     420

TTTCTCATGC ATGTCGGAGG TGAGGTGGAT GTGAGAAGCG CATACTGTGC TGCCTCCGTA     480

GCCTCGCTGA CCAACATCAT CACTCCAGAC CTCTTTGAGG GCACTGCTGA ATGGATAGCA     540

AGGTGTCAGA ACTGGGAAGG TGGCATTGGC GGGGTACCAG GGATGGAAGC CCATGGTGGC     600
```

```
TATACCTTCT GTGGCCTGGC CGCGCTGGTA ATCCTCAAGA GGGAACGTTC CTTGAACTTG    660

AAGAGCTTAT TACAATGGGT GACAAGCCGG CAGATGCTAT TTGAAGGAGG ATTTCAGGGC    720

CGCTGCAACA AGCTGGTGGA TGGCTGCTAC TCCTTCTGGC AGGCGGGGCT CCTGCCCCTG    780

CTCCACCGCG CACTGCACGC CCAAGGTGAC CCTGCCCTTA GCATGAGCCA CTGGATGTTC    840

CATCAGCAGG CCCTGCAGGA GTACATCCTG ATGTGCTGCC AGTGCCCTGC GGGGGGGCTT    900

CTGGATAAAC CTGGCAAGTC GCGTGATTTC TACCACACCT GCTACTGCCT GAGCGGCCTG    960

TCCATAGCCC AGCACTTCGG CAGCGGAGCC ATGTTGCATG ATGTGGTCCT GGGTGTGCCC   1020

GAAAACGCTC TGCAGCCCAC TCACCCAGTG TACAACATTG ACCAGACAA GGTGATCCAG    1080

GCCACTACAT ACTTTCTACA GAAGCCAGTC CCAGGTTTTG AGGAGCTTAA GGATGAGACA   1140

TCGGCAGAGC CTGCAACCGA CTAGAGGACC TGGGTCCCGG CAGCTCTTTG CTCACCCATC   1200

TCCCCAGTCA GACAAGGTTT ATACGTTTCA ATACATACTG CATTCTGT              1248
```

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:9:

```
Thr Lys Cys Val Ile Met
1               5
```

(2) INFORMATION FOR SEQ ID NO:10:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:10:

```
Cys Val Ile Met
1
```

(2) INFORMATION FOR SEQ ID NO:11:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:11:

```
Lys Lys Ser Lys Thr Lys Cys Val Ile Met
1               5                   10
```

(2) INFORMATION FOR SEQ ID NO:12:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:12:

```
Cys Xaa Xaa Xaa
1
```

(2) INFORMATION FOR SEQ ID NO:13:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:13:

Cys Ser Ile Met
1

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:14:

Cys Ala Ile Met
1

(2) INFORMATION FOR SEQ ID NO:15:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:15:

Arg Ala Ser Asn Arg Ser Cys Ala Ile Met
1             5                 10

(2) INFORMATION FOR SEQ ID NO:16:

(i) SEQUENCE CHARACTERISTICS:
        (A) LENGTH: 10 amino acids
        (B) TYPE: amino acid
        (C) STRANDEDNESS: single
        (D) TOPOLOGY: linear (xi) SEQUENCE DESCRIPTION: SEQ ID NO:16:

Thr Gln Ser Pro Gln Asn Cys Ser Ile Met
1             5                 10

(2) INFORMATION FOR SEQ ID NO:17:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:17:

Cys Ile Ile Met
1

(2) INFORMATION FOR SEQ ID NO:18:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:18:

Cys Val Val Met
1

(2) INFORMATION FOR SEQ ID NO:19:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:19:

Cys Val Leu Ser
1

(2) INFORMATION FOR SEQ ID NO:20:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:20:

Cys Val Leu Met
1

(2) INFORMATION FOR SEQ ID NO:21:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:21:

Cys Cys Val Gln
1

(2) INFORMATION FOR SEQ ID NO:22:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:22:

Cys Ile Ile Cys
1

(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:23:

Cys Ile Ile Ser
1

(2) INFORMATION FOR SEQ ID NO:24:

(i) SEQUENCE CHARACTERISTICS:
        (A) LENGTH: 4 amino acids
        (B) TYPE: amino acid
        (C) STRANDEDNESS: single (D) TOPOLOGY: linear (xi) SEQUENCE DESCRIPTION: SEQ ID NO:24:

Cys Val Ile Ser
1

(2) INFORMATION FOR SEQ ID NO:25:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:25:

Cys Val Ile Ala
1

(2) INFORMATION FOR SEQ ID NO:26:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:26:

Cys Val Ile Leu
1

(2) INFORMATION FOR SEQ ID NO:27:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:27:

Cys Leu Ile Leu
1

(2) INFORMATION FOR SEQ ID NO:28:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:28:

Cys Leu Leu Leu
1

(2) INFORMATION FOR SEQ ID NO:29:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:29:

Cys Thr Val Ala
1

(2) INFORMATION FOR SEQ ID NO:30:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:30:

Cys Val Ala Met
1

(2) INFORMATION FOR SEQ ID NO:31:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:31:

Cys Lys Ile Met
1

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:32:

Cys Leu Ile Met
1

(2) INFORMATION FOR SEQ ID NO:33:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:33:

Cys Phe Ile Met
1

(2) INFORMATION FOR SEQ ID NO:34:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:34:

Cys Val Phe Met
1

(2) INFORMATION FOR SEQ ID NO:35:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:35:

Cys Val Ile Phe
1

(2) INFORMATION FOR SEQ ID NO:36:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:36:

Cys Glu Ile Met
1

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:37:

Cys Gly Ile Met
1

(2) INFORMATION FOR SEQ ID NO:38:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:38:

Cys Pro Ile Met
1

(2) INFORMATION FOR SEQ ID NO:39:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:39:

Cys Val Tyr Met
1

(2) INFORMATION FOR SEQ ID NO:40:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:40:

Cys Val Thr Met
1

(2) INFORMATION FOR SEQ ID NO:41:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:41:

Cys Val Pro Met
1

(2) INFORMATION FOR SEQ ID NO:42:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:42:

Cys Val Ser Met
1

(2) INFORMATION FOR SEQ ID NO:43:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:43:

Cys Val Ile Val
1

(2) INFORMATION FOR SEQ ID NO:44:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:44:

Cys Val Ile Pro
1

(2) INFORMATION FOR SEQ ID NO:45:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:45:

Cys Val Ile Ile
1

(2) INFORMATION FOR SEQ ID NO:46:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:46:

Cys Val Trp Met
1

(2) INFORMATION FOR SEQ ID NO:47:

(i) SEQUENCE CHARACTERISTICS:
        (A) LENGTH: 4 amino acids (B) TYPE: amino acid
            (C) STRANDEDNESS: single
            (D) TOPOLOGY: linear (xi) SEQUENCE DESCRIPTION: SEQ ID NO:47:

Cys Ile Phe Met
1

(2) INFORMATION FOR SEQ ID NO:48:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:48:

Cys Asn Phe Asp Asn Pro Val Ser Gln Lys Thr Thr
1               5                   10

(2) INFORMATION FOR SEQ ID NO:49:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO:49:

Thr Lys Val Cys Ile Met
1               5

(2) INFORMATION FOR SEQ ID NO:50:

(i) SEQUENCE CHARACTERISTICS:
            (A) LENGTH: 10 amino acids
            (B) TYPE: amino acid
            (C) STRANDEDNESS: single
            (D) TOPOLOGY: linear (xi) SEQUENCE DESCRIPTION: SEQ ID NO:50:

Lys Asn Asn Leu Lys Asp Cys Gly Leu Phe
1               5                   10

(2) INFORMATION FOR SEQ ID NO:51:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:51:

Cys Val Lys Met
1

(2) INFORMATION FOR SEQ ID NO:52:

(i) SEQUENCE CHARACTERISTICS:
            (A) LENGTH: 4 amino acids
            (B) TYPE: amino acid
            (C) STRANDEDNESS: single
            (D) TOPOLOGY: linear (xi) SEQUENCE DESCRIPTION: SEQ ID NO:52:

Cys Val Ile Lys
1

(2) INFORMATION FOR SEQ ID NO:53:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:53:

Lys Thr Ser Cys Val Ile Met
1            5

(2) INFORMATION FOR SEQ ID NO:54:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:54:

Cys Xaa Ile Met
1

(2) INFORMATION FOR SEQ ID NO:55:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:55:

Cys Val Xaa Met
1

(2) INFORMATION FOR SEQ ID NO:56:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:56:

Cys Val Ile Xaa
1

(2) INFORMATION FOR SEQ ID NO:57:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:57:

GANGCNATNG ANNT                                        14

(2) INFORMATION FOR SEQ ID NO:58:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:58:

CNNAANTGCC ANAC                                        14

(2) INFORMATION FOR SEQ ID NO:59:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:59:

```
Asp Ala Ile Glu Leu Asn Ala Ala Asn Tyr Thr Val Trp His Phe Arg
1               5                  10                  15
```

(2) INFORMATION FOR SEQ ID NO:60:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:60:

```
GCNTANTGNG CNGC                                                14
```

(2) INFORMATION FOR SEQ ID NO:61:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:61:

```
GGNGTNAGNA TNAT                                                14
```

(2) INFORMATION FOR SEQ ID NO:62:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:62:

```
GCGTACTGTG CGGCCTCAGT AGCCTCTCTC ACCAACATNA TCAC               44
```

(2) INFORMATION FOR SEQ ID NO:63:

(i) SEQUENCE CHARACTERISTICS:
        (A) LENGTH: 16 amino acids
        (B) TYPE: amino acid
        (C) STRANDEDNESS: single
        (D) TOPOLOGY: linear (xi) SEQUENCE DESCRIPTION: SEQ ID NO:63:

```
Ala Tyr Cys Ala Ala Ser Val Ala Ser Leu Thr Asn Ile Ile Thr Pro
1               5                  10                  15
```

(2) INFORMATION FOR SEQ ID NO:64:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:64:

```
GANGCNATNG ANNTAAACGC ACGGAACTAT ACGGTCTGGC ACTT               44
```

(2) INFORMATION FOR SEQ ID NO:65:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:65:

Cys Ala Ile Leu
1

(2) INFORMATION FOR SEQ ID NO:66:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:66:

Cys Ile Lys Ser
1

(2) INFORMATION FOR SEQ ID NO:67:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:67:

Leu Gln Ser Lys His Ser Arg Glu Ser Asp Ile Pro Ala Ser Val
1               5                   10                  15

(2) INFORMATION FOR SEQ ID NO:68:

(i) SEQUENCE CHARACTERISTICS:
        (A) LENGTH: 17 amino acids
        (B) TYPE: amino acid
        (C) STRANDEDNESS: single
        (D) TOPOLOGY: linear (xi) SEQUENCE DESCRIPTION: SEQ ID NO:68:

Ile Gln Ala Thr Thr His Phe Leu Gln Lys Pro Val Pro Gly Phe Glu
1               5                   10                  15
Glu (2) INFORMATION FOR SEQ ID NO:69:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:69:

GACTCGAGTC GACATCGAT                                            19

(2) INFORMATION FOR SEQ ID NO:70:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:70:

Leu Xaa Asp Asp Xaa Xaa Glu
1               5

(2) INFORMATION FOR SEQ ID NO:71:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:71:

Cys Xaa Xaa Leu
1

(2) INFORMATION FOR SEQ ID NO:72:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:72:

Asp Glu Ser Gly Pro Gly Cys Met Ser Cys Lys Cys Val Leu Ser
1               5                  10                  15

(2) INFORMATION FOR SEQ ID NO:73:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:73:

Lys Lys Lys Lys Lys Lys Ser Lys Thr Lys Cys Val Ile Met
1               5                  10

(2) INFORMATION FOR SEQ ID NO:74:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:74:

Asp Glu Ser Gly Pro Gly Cys Met Ser Cys Lys Cys Val Ile Met
1               5                  10                  15

(2) INFORMATION FOR SEQ ID NO:75:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:75:

Lys Lys Lys Lys Lys Ser Lys Ser Cys Lys Cys Val Leu Ser
1               5                   10                  15

(2) INFORMATION FOR SEQ ID NO:76:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:76:

Pro Val Pro Gly Lys Ala Arg Lys Lys Ser Ser Cys Gln Leu Leu
1               5                   10                  15

(2) INFORMATION FOR SEQ ID NO:77:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:77:

Lys Lys Lys Lys Lys Lys Ser Lys Thr Lys
1               5                   10

(2) INFORMATION FOR SEQ ID NO:78:

(i) SEQUENCE CHARACTERISTICS:
        (A) LENGTH: 377 amino acids
        (B) TYPE: amino acid
        (C) STRANDEDNESS: single
        (D) TOPOLOGY: linear (xi) SEQUENCE DESCRIPTION: SEQ ID NO:78:

Met Val Ala Thr Glu Asp Glu Arg Leu Ala Gly Ser Gly Glu Gly Glu
1               5                   10                  15

Arg Leu Asp Phe Leu Arg Asp Arg His Val Arg Phe Phe Gln Arg Cys
                20                  25                  30

Leu Gln Val Leu Pro Glu Arg Tyr Ser Ser Leu Glu Thr Ser Arg Leu
            35                  40                  45

Thr Ile Ala Phe Phe Ala Leu Ser Gly Leu Asp Met Leu Asp Ser Leu
        50                  55                  60

Asp Val Val Asn Lys Asp Asp Ile Ile Glu Trp Ile Tyr Ser Leu Gln
65                  70                  75                  80

Val Leu Pro Thr Glu Asp Arg Ser Asn Leu Asn Arg Cys Gly Phe Arg
                85                  90                  95

Gly Ser Ser Tyr Leu Gly Ile Pro Phe Asn Pro Ser Lys Ala Pro Gly
            100                 105                 110

Thr Ala His Pro Tyr Asp Ser Gly His Ile Ala Met Thr Tyr Thr Gly
            115                 120                 125

Leu Ser Cys Leu Val Ile Leu Gly Asp Asp Leu Ser Arg Val Asn Lys
        130                 135                 140

Glu Ala Cys Leu Ala Gly Leu Arg Ala Leu Gln Leu Glu Asp Gly Ser
145                 150                 155                 160

Phe Cys Ala Val Pro Glu Gly Ser Glu Asn Asp Met Arg Phe Val Tyr
                165                 170                 175

-continued

```
Cys Ala Ser Cys Ile Cys Tyr Met Leu Asn Asn Trp Ser Gly Met Asp
            180                 185                 190

Met Lys Lys Ala Ile Thr Tyr Ile Arg Arg Ser Met Ser Tyr Asp Asn
            195                 200                 205

Gly Leu Ala Gln Gly Ala Gly Leu Glu Ser His Gly Gly Ser Thr Phe
            210                 215                 220

Cys Gly Ile Ala Ser Leu Cys Leu Met Gly Lys Leu Glu Glu Val Phe
225                 230                 235                 240

Ser Glu Lys Glu Leu Asn Arg Ile Lys Arg Trp Cys Ile Met Arg Gln
            245                 250                 255

Gln Asn Gly Tyr His Gly Arg Pro Asn Lys Pro Val Asp Thr Cys Tyr
            260                 265                 270

Ser Phe Trp Val Gly Ala Thr Leu Lys Leu Leu Lys Ile Phe Gln Tyr
            275                 280                 285

Thr Asn Phe Glu Lys Asn Arg Asn Tyr Ile Leu Ser Thr Gln Asp Arg
            290                 295                 300

Leu Val Gly Gly Phe Ala Lys Trp Pro Asp Ser His Pro Asp Ala Leu
305                 310                 315                 320

His Ala Tyr Phe Gly Ile Cys Gly Leu Ser Leu Met Glu Glu Ser Gly
            325                 330                 335

Ile Cys Lys Val His Pro Ala Leu Asn Val Ser Thr Arg Thr Ser Glu
            340                 345                 350

Arg Leu Leu Asp Leu His Gln Ser Trp Lys Thr Lys Asp Ser Lys Gln
            355                 360                 365

Cys Ser Glu Asn Val His Ile Ser Thr
370                 375
```

(2) INFORMATION FOR SEQ ID NO:79:

(i) SEQUENCE CHARACTERISTICS:
        (A) LENGTH: 1969 base pairs
        (B) TYPE: nucleic acid
        (C) STRANDEDNESS: single
        (D) TOPOLOGY: linear (xi) SEQUENCE DESCRIPTION: SEQ ID NO:79:

```
GAATAAAATG AACAATTCAG TTCCTCAGTC ACATGAGCTG TGTGTCAAAT GCACAACAGC     60

CGTATGTGGC TCGTGGCCCC TGTACCGGAC ACTCCCATCC CTGCAGAGTT ACTGGACAGT    120

GCTGATCTAG GGATTCTGTT ACAAAATCCA TGAAAGTGTT CAGCACAATG CCGGGCCCAT    180

ATAAACGTCA GTAGTTGTTG TTATTATAAT TAGTCTTGAC CCAACGGCAA ATTCACTTTG    240

AGACCTTAGA TAAATCACTC TACCTCTCTG AGCCTGGTTT CCTTGCCCTA AAAGGATGGC    300

AAGGGGCTGG GCATGGTGGC CACTGAGGAT GAGAGGCTAG CAGGGAGCGG TGAGGGAGAG    360

CGGCTGGATT TCTTACGGGA TCGGCACGTG CGATTTTTCC AGCGCTGCCT CCAGGTTTTG    420

CCGGAGCGCT ATTCTTCACT CGAGACAAGC AGGTTGACAA TTGCATTTTT TGCACTCTCC    480

GGGCTGGATA TGTTGGATTC CTTAGATGTG GTGAACAAAG ATGATATAAT AGAGTGGATT    540

TATTCCCTGC AGGTCCTTCC CACAGAAGAC AGATCAAATC TAAATCGCTG TGGTTTCCGA    600

GGCTCTTCAT ACCTGGGTAT TCCGTTCAAT CCATCAAAGG CTCCTGGAAC AGCTCATCCT    660

TATGATAGTG GCCACATTGC AATGACCTAC ACTGGCCTCT CATGCTTAGT TATTCTTGGA    720

GACGACTTAA GCCGAGTAAA TAAAGAAGCT TGCTTAGCGG GCTTGAGAGC CCTTCAGCTG    780

GAAGATGGGA GTTTTGTGC AGTACCTGAA GGCAGTGAAA ATGACATGCG ATTTGTGTAC    840

TGTGCTTCCT GTATTTGCTA TGCTCAACAA ACTGGTCAG GCATGGATAT GAAAAAAGCC    900
```

-continued

```
ATCACCTATA TTAGAAGGAG TATGTCCTAT GACAATGGAC TGGCACAGGG AGCTGGACTT    960

GAATCTCATG GAGGATCAAC TTTTTGTGGC ATTGCCTCAC TATGTCTGAT GGGTAAACTA   1020

GAAGAAGTTT TTTCAGAAAA AGAATTGAAC AGGATAAAGA GGTGGTGTAT AATGAGGCAA   1080

CAAAATGGTT ATCATGGAAG ACCTAATAAG CCTGTAGACA CCTGTTATTC TTTTTGGGTG   1140

GGAGCAACTC TGAAGCTTCT AAAAATTTTC CAATACACTA ACTTTGAGAA AAATAGAAAT   1200

TACATCTTAT CAACTCAAGA TCGCCTTGTA GGGGGATTTG CCAAGTGGCC AGACAGTCAT   1260

CCAGATGCTT TGCATGCATA CTTTGGGATC TGTGGCCTGT CACTAATGGA GGAAAGTGGA   1320

ATTTGTAAAG TTCATCCTGC TCTGAATGTA AGCACACGGA CTTCTGAACG CCTTCTAGAT   1380

CTCCATCAAA GCTGGAAAAC CAAGGACTCT AAACAATGCT CAGAGAATGT ACATATCTCC   1440

ACATGACTGA TTTTAGATTG GGAGGGTGGG GGGGATTTGT AGCATAACTG TAGCTCAAGT   1500

TTAAAAGCCA TGTATAACCA AGTGTGCTCT TTTTTTAAAA GGTAGAGTCT TACAATCAAA   1560

TCTCCTGCTG ATTTCACTTT GGGATATGGT CTTGAGCCAG TAATCTTTAT ACTGGGTTTC   1620

AAGAAAATCT TTGTTGAAGT TTGAACCACA ACTTTGTCGT GGTTCTTAAA TGTTTATACT   1680

GTATTTCTAA GAAGTTGTTT GAGGCAAATT AACTGTATGT GTGTAGGTTA TCTTTTTAAA   1740

AACTCTTCAG TGCAAATTGT ATCTTATTAT AAAATGGACA CAAATTTTCA AGTTTACACT   1800

TCATATAGCA TTGATAATCT TCAGGTGAAC ACTTAGTGAT CATTTAAAAA GCTCACTGCT   1860

GATCGTAGAA AATTTGCTTT AATTAATTAA GTATCTGGGA TTATTCTTTG AAAACAGATG   1920

ACCATAATTT TTTTTAAAGA AGAGTGACTT ATTTTGTCTT ATTCTTAAG              1969
```

(2) INFORMATION FOR SEQ ID NO:80:

(i) SEQUENCE CHARACTERISTICS:
        (A) LENGTH: 377 amino acids
        (B) TYPE: amino acid
        (C) STRANDEDNESS: single
        (D) TOPOLOGY: linear (xi) SEQUENCE DESCRIPTION: SEQ ID NO:80:

```
Met Ala Ala Thr Glu Asp Asp Arg Leu Ala Gly Ser Gly Glu Gly Glu
1               5                   10                  15

Arg Leu Asp Phe Leu Arg Asp Arg His Val Arg Phe Phe Gln Arg Cys
                20                  25                  30

Leu Gln Val Leu Pro Glu Arg Tyr Ser Ser Leu Glu Thr Ser Arg Leu
            35                  40                  45

Thr Ile Ala Phe Phe Ala Leu Ser Gly Leu Asp Met Leu Asp Ser Leu
        50                  55                  60

Asp Val Val Asn Lys Asp Asp Ile Ile Glu Trp Ile Tyr Ser Leu Gln
65                  70                  75                  80

Val Leu Pro Thr Glu Asp Arg Ser Asn Leu Asp Arg Cys Gly Phe Arg
                85                  90                  95

Gly Ser Ser Tyr Leu Gly Ile Pro Phe Asn Pro Ser Lys Asn Pro Gly
                100                 105                 110

Thr Ala His Pro Tyr Asp Ser Gly His Ile Ala Met Thr Tyr Thr Gly
            115                 120                 125

Leu Ser Cys Leu Ile Ile Leu Gly Asp Asp Leu Ser Arg Val Asp Lys
        130                 135                 140

Glu Ala Cys Leu Ala Gly Leu Arg Ala Leu Gln Leu Glu Asp Gly Ser
145                 150                 155                 160

Phe Cys Ala Val Pro Glu Gly Ser Glu Asn Asp Met Arg Phe Val Tyr
                165                 170                 175
```

```
Cys Ala Ser Cys Ile Cys Tyr Met Leu Asn Asn Trp Ser Gly Met Asp
            180                 185                 190

Met Lys Lys Ala Ile Ser Tyr Ile Arg Arg Ser Met Ser Tyr Asp Asn
            195                 200                 205

Gly Leu Ala Gln Gly Ala Gly Leu Glu Ser His Gly Gly Ser Thr Phe
            210                 215                 220

Cys Gly Ile Ala Ser Leu Cys Leu Met Gly Lys Leu Glu Glu Val Phe
225                 230                 235                 240

Ser Glu Lys Glu Leu Asn Arg Ile Lys Arg Trp Cys Ile Met Arg Gln
                245                 250                 255

Gln Asn Gly Tyr His Gly Arg Pro Asn Lys Pro Val Asp Thr Cys Tyr
            260                 265                 270

Ser Phe Trp Val Gly Ala Thr Leu Lys Leu Leu Lys Ile Phe Gln Tyr
            275                 280                 285

Thr Asn Phe Glu Lys Asn Arg Asn Tyr Ile Leu Ser Thr Gln Asp Arg
            290                 295                 300

Leu Val Gly Gly Phe Ala Lys Trp Pro Asp Ser His Pro Asp Ala Leu
305                 310                 315                 320

His Ala Tyr Phe Gly Ile Cys Gly Leu Ser Leu Met Glu Glu Ser Gly
            325                 330                 335

Ile Cys Lys Val His Pro Ala Leu Asn Val Ser Thr Arg Thr Ser Glu
            340                 345                 350

Arg Leu Arg Asp Leu His Gln Ser Trp Lys Thr Lys Asp Ser Lys Gln
            355                 360                 365

Cys Ser Asp Asn Val His Ile Ser Ser
370                 375
```

(2) INFORMATION FOR SEQ ID NO:81:

(i) SEQUENCE CHARACTERISTICS:
        (A) LENGTH: 1568 base pairs
        (B) TYPE: nucleic acid
        (C) STRANDEDNESS: single
        (D) TOPOLOGY: linear (xi) SEQUENCE DESCRIPTION: SEQ ID NO:81:

```
GGACAGCGCA TGGCGGCCAC AGAGGATGAC AGACTGGCGG GGAGCGGAGA AGGAGAACGG      60

CTGGATTTCC TGCGGGACCG ACACGTGCGG TTCTTCCAGC GCTGCCTCCA GGTCTTGCCG     120

GAGCGGTATT CTTCGCTGGA GACCAGCAGG CTGACAATTG CATTTTTTGC ACTCTCTGGG     180

CTGGATATGT TGGACTCCTT GGATGTGGTG AACAAAGACG ATATAATAGA GTGGATTTAT     240

TCCTTGCAGG TTCTTCCCAC AGAAGACAGG TCAAATCTGG ATCGCTGTGG TTTCCGAGGT     300

TCTTCATATT TGGGTATTCC ATTCAACCCA TCAAAGAATC CAGGCACAGC TCATCCTTAT     360

GACAGTGGAC ACATAGCGAT GACTTACACT GGTCTTTCCT GTTTAATTAT TCTTGGAGAT     420

GATTTAAGCC GAGTAGATAA AGAAGCTTGC TTAGCAGGCT TGAGAGCACT TCAGCTGGAA     480

GATGGGAGCT TCTGTGCTGT TCCTGAAGGC AGTGAGAATG ACATGAGGTT TGTGTACTGT     540

GCTTCCTGCA TTTGCTATAT GCTCAACAAC TGGTCAGGCA TGGATATGAA GAAAGCCATC     600

AGCTACATTA GAAGAAGTAT GTCCTATGAC AATGGCCTGG CACAGGGGGC AGGACTTGAG     660

TCTCATGGAG GATCCACCTT TTGTGGCATT GCGTCACTGT GCCTGATGGG TAAACTGGAA     720

GAAGTTTTTT CAGAGAAAGA ACTGAACCGG ATAAAGAGGT GGTGCATAAT GAGGCAGCAG     780

AACGGGTACC ACGGAAGACC TAACAAGCCT GTCGACACCT GTTACTCTTT CTGGGTGGGA     840

GCAACACTAA AGCTTTTGAA AATTTTCCAG TACACTAACT TTGAGAAGAA TAGGAATTAC     900
```

```
ATCTTATCAA CTCAGGATCG CCTTGTTGGG GGATTTGCTA AATGGCCAGA CAGTCATCCA      960

GATGCTTTGC ATGCGTACTT CGGGATCTGT GGCCTGTCAC TAATGGAGGA GAGTGGAATT     1020

TGTAAAGTTC ATCCTGCTCT GAATGTAAGC ACACGAACTT CTGAGCGCCT CCGAGATCTC     1080

CATCAAAGCT GGAAGACCAA GGACTCTAAA CAGTGCTCAG ACAATGTCCA TATTTCCAGT     1140

TGACTAACCC TGGGGTAAAG GGTGTGTAGC ATACGTGTAG CTCAAGGTTA AAAGCCATGT     1200

GTAACCAAGT GTGCTCTTCT TTAAGGGTTA GTCGTAAAAG TCAGAAGCGT GTACTGCTAG     1260

TTCTTCAGGA TATGCTCTTA GGCCAGTGAC CACTGTCATG GATTTCAAGA AAATCCTTGT     1320

TGACGTGTGG ACATCAGCAG AACTCTGGTA TGGTTCTTAA CTGTTACACT GTGTTTCTGA     1380

GACCTTTCAT GGGGCAGATA TGTTTGTAGG TTATCTTCTT AAAACCCTCA GTACAAGTTC     1440

TGGCTTACAA AATGTACGTA AACCTTCAAA ACAAGTTTAC ACTCCATATG GCATTGATAA     1500

TCTTCAGGTG AGCATTTAAC GATCACTTAA AAATCGCTAC TGCTGATGGG AAGAAATTTG     1560

TTTATCCG                                                             1568
```

(2) INFORMATION FOR SEQ ID NO:82:

(i) SEQUENCE CHARACTERISTICS:
        (A) LENGTH: 189 amino acids
        (B) TYPE: amino acid
        (C) STRANDEDNESS: single
        (D) TOPOLOGY: linear (xi) SEQUENCE DESCRIPTION: SEQ ID NO:82:

```
Met Thr Glu Tyr Lys Leu Val Val Gly Ala Cys Gly Val Gly Lys
1               5                   10                  15

Ser Ala Leu Thr Ile Gln Leu Ile Asp Asn His Phe Val Asp Glu Tyr
                20                  25                  30

Asp Pro Thr Ile Glu Asp Ser Tyr Arg Lys Gln Val Val Ile Asp Gly
                35                  40                  45

Glu Thr Cys Leu Leu Asp Ile Leu Asp Thr Ala Gly Gln Glu Glu Tyr
            50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
                100                 105                 110

Leu Val Gly Asn Lys Cys Asp Leu Pro Ser Arg Thr Val Asp Thr Lys
                115                 120                 125

Gln Ala Gln Asp Leu Ala Arg Ser Tyr Gly Ile Pro Phe Ile Gln Thr
            130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
                180                 185
```

(2) INFORMATION FOR SEQ ID NO:83:

(i) SEQUENCE CHARACTERISTICS:
        (A) LENGTH: 574 base pairs
        (B) TYPE: nucleic acid
        (C) STRANDEDNESS: single
        (D) TOPOLOGY: linear (xi) SEQUENCE DESCRIPTION: SEQ ID NO:83:

```
ATGACTGAAT ATAAACTTGT GGTAGTTGGA GCTTGTGGCG TAGGCAAGAG TGCCTTGACG        60
ATACAGCTAA TTGACAATCA TTTTGTGGAC GAATATGATC CAACAATAGA GGATTCCTAC       120
AGGAAGCAAG TAGTAATTGA TGGAGAAACC TGTCTCTTGG ATATTCTCGA CACAGCAGGT       180
CAAGAGGAGT ACAGTGCAAT GAGGGACCAG TACATGAGGA CTGGGGAGGG CTTTCTTTGT       240
GTATTTGCCA TAAATAATAC TAAATCATTT GAAGATATTC ACCATTATAG AGAACAAATT       300
AAAAGAGTTA AGGACTCTGA AGATGTACCT ATGGTCCTAG TAGGAAATAA ATGTGATTTG       360
CCTTCTAGAA CAGTAGACAC AAAACAGGCT CAGGACTTAG CAAGAAGTTA TGGAATTCCT       420
TTTATTCAAA CATCAGCAAA GACAAGACAG AGAGTGGAGG ATGCTTTTTA TACATTGGTG       480
AGAGAGATCC GACAATACAG ATTGAAAAAA ATCAGCAAAG AAGAAAAGAC TCCTGGCTGT       540
GTGAAAATTA AAAATGCAT TATAATGTAA TCTG                                    574
```

(2) INFORMATION FOR SEQ ID NO:84:

(i) SEQUENCE CHARACTERISTICS:
        (A) LENGTH: 188 amino acids
        (B) TYPE: amino acid
        (C) STRANDEDNESS: single
        (D) TOPOLOGY: linear (xi) SEQUENCE DESCRIPTION: SEQ ID NO:84:

```
Met Thr Glu Tyr Lys Leu Val Val Val Gly Ala Cys Gly Val Gly Lys
1               5                  10                  15

Ser Ala Leu Thr Ile Gln Leu Ile Asp Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Gln Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

(2) INFORMATION FOR SEQ ID NO:85:

(i) SEQUENCE CHARACTERISTICS:
        (A) LENGTH: 607 base pairs
        (B) TYPE: nucleic acid
        (C) STRANDEDNESS: single
        (D) TOPOLOGY: linear (xi) SEQUENCE DESCRIPTION: SEQ ID NO:85:

-continued

```
ATGACTGAAT ATAAACTTGT GGTAGTTGGA GCTTGTGGCG TAGGCAAGAG TGCCTTGACG      60

ATACAGCTAA TTGACAATCA TTTTGTGGAC GAATATGATC CAACAATAGA GGATTCCTAC     120

AGGAAGCAAG TAGTAATTGA TGGAGAAACC TGTCTCTTGG ATATTCTCGA CACAGCAGGT     180

CAAGAGGAGT ACAGTGCAAT GAGGGACCAG TACATGAGGA CTGGGGAGGG CTTTCTTTGT     240

GTATTTGCCA TAAATAATAC TAAATCATTT GAAGATATTC ACCATTATAG AGAACAAATT     300

AAAAGAGTTA AGGACTCTGA AGATGTACCT ATGGTCCTAG TAGGAAATAA ATGTGATTTG     360

CCTTCTAGAA CAGTAGACAC AAAACAGGCT CAGGACTTAG CAAGAAGTTA TGGAATTCCT     420

TTTATTCAAA CATCAGCAAA GACAAGACAG GGTGTTGATG ATGCCTTCTA TACATTAGTT     480

CGAGAAATTC GAAAACATAA AGAAAAGATG AGCAAAGATG GTAAAAAGAA GAAAAAGAAG     540

TCAAAGACAA AGTGTGTAAT TATGTAAATA CAATTTGTAC TTTTTTCTTA AGGCATACTA     600

GTACAAG                                                                607
```

METHODS FOR THE IDENTIFICATION OF FARNESYLTRANSFERASE INHIBITORS

This application is a continuation-in-part of copending U.S. Ser. No. 08/021,625, filed Feb. 16, 1993; which is a continuation-in-part of U.S. Ser. No. 07/822,011, filed Jan. 16, 1992, abandoned; which is a continuation-in-part of U.S. Ser. No. 07/937,893, filed Dec. 22, 1992, which is a national stage application of PCT/US/91/02650, filed Apr. 18, 1991; which is a continuation-in-part of U.S. Ser. No. 07/615,715, filed Nov. 20, 1990 (now U.S. Pat. No. 5,141,851); which is a continuation-in-part application of U.S. Ser. No. 07/510, 706, filed Apr. 18, 1990, abandoned. Each of the foregoing applications are incorporated herein by reference without disclaimer.

The government owns certain rights in the present invention pursuant to NIH grant numbers 5-PO1-HL20948, HG00298 and T32 GM08404.

BACKGROUND OF THE INVENTION

1. Field of the Invention

This invention relates to assay methods for detecting inhibitors of farnesyltransferase enzymes. In particular, the invention relates to methods for detecting inhibitors using K-rasB preparations as the farnesyl acceptor substances.

2. Description of the Related Art

In recent years, some progress has been made in the elucidation of cellular events lending to the development or progression of various types of cancers. A great amount of research has centered on identifying genes which are altered or mutated in cancer relative to normal cells. In fact, genetic research has led to the identification of a variety of gene families in which mutations can lead to the development of a wide variety of tumors. The ras gene family is a family of closely related genes that frequently contain mutations involved in many human tumors, including tumors of virtually every tumor group (see, e.g., Bos, 1989). In fact, altered ras genes are the most frequently identified oncogenes in human tumors (Barbacid, 1987).

The ras gene family comprises three genes, H-ras, K-ras and N-ras, which encode similar proteins with molecular weights of about 21,000 (Barbacid, 1987). These proteins, often termed p21$^{ras}$, comprise a family of GTP-binding and hydrolyzing proteins that regulate cell growth when bound to the inner surface of the plasma membrane (Hancock, et al., 1989). Overproduction of P21$^{ras}$ proteins or mutations that abolish their GTP-ase activity lead to uncontrolled cell division (Gibbs et al., 1989). However, the activity of normal and oncogenic Ras proteins requires their attachment to the inner leaflet of the plasma membrane. This process is initiated by the covalent attachment of a hydrophobic farnesyl group to a cysteine at the fourth position from the COOH-terminus of the Ras protein. Mutation of this cysteine to a serine prevents farnesylation, abrogates membrane attachment, and abolishes the transforming ability of oncogenic Ras proteins (Hancock et al., 1989; Schafer and Rine, 1992).

Four Ras proteins, designated H-Ras, N-Ras, K-rasA, and K-RasB, are expressed in animal cells (Barbacid, 1987). K-rasA and K-rasB are alternatively spliced products of a single gene (Barbacid, 1987). These proteins resemble each other closely with the exception of their COOH-terminal domains. All of them are believed to function similarly in activating cell growth. All four terminate in CAAX boxes with the following sequences: CVIM (K-rasB), CIIM (K-rasA), CVVM (N-Ras), and CVLS (H-Ras). K-rasB differs from the other three forms of Ras because it contains a prominent string of lysine residues (8 lysines among the 10 residues immediately adjacent to the farnesylated cysteine). These lysines assist in the membrane attachment of farnesylated K-rasB, presumably by binding to negatively charged phospholipids on the inner surface of the plasma membrane (Hancock et al., 1990). H-Ras is the form most often studied experimentally in cell culture. However, mutations in K-RasB are by far the most frequent in human tumors (Barbacid, 1987).

Farnesylation of Ras proteins is catalyzed by a heterodimeric enzyme, CAAX farnesyltransferase (farnesyltransferase), which was first purified and cloned from rat brain (Example I herein) and subsequently purified from bovine brain (Pompliano et al., 1993). This Zn$^{2+}$-containing enzyme catalyzes the Mg$^{2+}$-dependent transfer of a farnesyl group from farnesyl pyrophosphate (FPP) to Ras proteins and several other proteins, including nuclear lamins (Reiss et al., 1992).

CAAX farnesyltransferase is one of two enzymes that attach isoprenes to cysteines at the fourth position from the COOH-terminus of proteins (Brown and Goldstein, 1993; Casey, 1992). The second enzyme, CAAX geranylgeranyltransferase, is also known as geranylgeranyltransferase type-I or geranylgeranyltransferase-1. This enzyme transfers a 20-carbon geranylgeranyl group, which is even more hydrophobic than the 15-carbon farnesyl. Both prenyltransferases recognize COOH-terminal tetrapeptides that are designated as CAAX boxes in which C is cysteine, A stands for an aliphatic amino acid, and X is a variable amino acid that dictates the relative specificity of the protein for the two prenyltransferases. In most farnesylated proteins, including Ras proteins and nuclear lamins, X is methionine or serine. Geranylgeranylated proteins, including the GTP-binding protein Rap1B and the γ-subunits of heterotrimeric G proteins, usually terminate in leucine (Brown and Goldstein, 1993; Casey, 1992; Reiss et al., 1992; Moores et al., 1991).

CAAX farnesyltransferase and geranylgeranyltransferase-1 are both α/β heterodimers (Brown and Goldstein, 1993; Casey, 1992; Moomaw and Casey, 1992; Yokoyama and Gelb, 1993). The α subunits of the two enzymes are identical (Example III herein, Seabra et al., 1991; Zhang et al., 1994), and the two rat β subunits show 28% identity (Zhang et al., 1994). Genetic studies in yeast confirm that the α-subunits of the two enzymes are the product of the same gene (Schafer and Rine, 1992). So far it has not been possible to separate the α and β subunits without denaturation, nor is it possible to produce high levels of one without the other by overexpression in animal (Chen et al., 1991b) or Sf9 cells (Chen et al., 1993; James et al., 1993). The β-subunit of rat brain farnesyltransferase binds the CAAX substrate, as determined from cross-linking studies (see Examples, Reiss et al., 1991). The role of the α-subunit has not yet been delineated (Andres et al., 1993).

The existence of a shared α-subunit suggests that the two CAAX prenyltransferases may have some overlapping substrate specificity. Consistent with this notion, studies with partially purified geranylgeranyltransferase-1 showed that its substrate specificity overlaps that of farnesyltransferase. Yokoyama et al. (1991) showed that geranylgeranyltransferase-1 will transfer [$^3$H] geranylgeranyl to a peptide corresponding to the COOH-terminal 10 residues of lamin B, which terminates in serine, albeit at much lower efficiency than was observed for leucine-terminated peptides. Moreover, the enzyme was able to attach [$^3$]farnesyl as well as [$^3$H]geranylgeranyl to peptides that terminate in leucine. In yeast, Trueblood et al. (1993) showed that the consequences of a deletion mutant of the β-subunit of CAAX farnesyltransferase could be overcome partially by overexpression of the β subunit of the geranylgeranyltransferase-1, and vice versa.

Although it appears to be clear that prenylation is a key event in ras-related cancer development, the nature of this event has remained obscure. Little is known, for example, of the role of farnesyltransferase enzyme involved in ras tumorigenesis or required by the tumor cell to achieve prenylation. If the mechanisms that underlie farnesylation of cancer-related proteins could be elucidated, then procedures and even pharmacologic agents could be developed in an attempt to control or inhibit expression of the oncogenic phenotype in a wide variety of cancers.

SUMMARY OF THE INVENTION

The present invention, in general and overall sense, concerns improved assay methods for farnesyltransferase assays, as may be used, e.g., in detecting inhibitors of farnesyltransferase. In particular, the invention provides improved assay methods for detecting inhibitors of farnesyltransferase using K-RasB proteins or peptides as the prenyl acceptor substances.

One aspect of the invention is the identification and characterization of an enzyme, termed CAAX farnesyltransferase or farnesyltransferase, involved in the oncogenic process through the transfer of farnesyl groups to various proteins including oncogenic ras proteins. The invention concerns, in part, the molecular cloning of mammalian farnesyltransferase subunits, the purification of the native or recombinant enzyme, protein and peptide substances that are capable of inhibiting the enzyme, and assay methods, particularly those using K-RasB, for the identification of further inhibitory compounds.

A certain object of the present invention is therefore to provide ready means for obtaining farnesyltransferase enzymes, by purification of the native enzyme from tissues of choice, or by purification of the recombinant enzyme from host cells that express the constituent subunits, which methods are proposed to be generally applicable to the purification of all such farnesyl protein transferases.

It is an additional object of the invention to provide means for obtaining these enzymes in a relatively purified form, allowing their use in predictive assays for identifying compounds having the ability to reduce the activity of or inhibit the farnesyltransferase activity, particularly in the context of $p21^{ras}$ proteins and, most preferably, in the context of K-RasB.

It is a still further object of the invention to identify classes of compounds that demonstrate farnesyltransferase inhibiting activity, along with a potential application of these compounds in the treatment of cancer, particularly ras-related cancers, and most particularly those K-rasB-related cancers that are prevalent in patients.

1. Farnesyltransferase Characterization

Accordingly, in certain embodiments, the present invention relates to compositions that include a purified farnesyltransferase enzyme, characterized as follows:

(a) capable of catalyzing the transfer of farnesyl to a protein or peptide having a farnesyl acceptor moiety;
(b) capable of binding to an affinity chromatography medium comprised of TKCVIM (SEQ ID NO:9) coupled to a suitable matrix;
(c) exhibiting a molecular weight of between about 70,000 and about 100,000 upon gel filtration chromatography; and
(d) having a farnesyltransferase activity that is capable of being inhibited by one of the following peptides:
  i) TKCVIM (SEQ ID NO:9);
  ii) CVIM (SEQ ID NO:10); or
  iii) KKSKTKCVIN (SEQ ID NO:11).

As used herein, the phrase "capable of catalyzing the transfer of farnesol to a protein or peptide having a farnesyl acceptor moiety," is intended to refer to the functional attributes of farnesyltransferase enzymes of the present invention, which catalyze the transfer of farnesol, typically in the form of all-trans farnesol, from all-trans farnesyl pyrophosphate to proteins which have a sequence recognized by the enzyme for attachment of the farnesyl moieties. Thus, the term "farnesyl acceptor moiety" is intended to refer to any protein, polypeptide or peptide that includes a recognition sequence, typically a short amino acid recognition sequence, which is recognized by the enzyme and to which a farnesyl group will be attached by such an enzyme. Preferred examples of farnesyl acceptor moieties are K-rasB proteins and peptides.

Farnesyl acceptor moieties have been characterized by others in various proteins as a four amino acid sequence found at the carboxyl terminus of target proteins. This four amino acid sequence has been characterized as CAAX (SEQ ID NO:12), wherein "C" is a cysteine residue, "A" refers to any aliphatic amino acid, and "X" refers to any amino acid. Of course, the term "aliphatic amino acid" is well-known in the art to mean any amino acid having an aliphatic side chain, such as, for example, leucine, isoleucine, alanine, methionine, valine, etc. While the most preferred aliphatic amino acids, for the purposes of the present invention include valine and isoleucine, it is believed that virtually any aliphatic amino acids in the designated position can be recognized within the farnesyl acceptor moiety. In addition, the enzyme has been shown to recognize a peptide containing a hydroxylated amino acid (serine) in place of an aliphatic amino acid (CSIM; SEQ ID NO:13).

Principal examples of proteins or peptides having a farnesyl acceptor moiety, for the purposes of the present invention, will be the $p21^{ras}$ proteins, including $p21^{H-ras}$, $p21^{K-rasA}$, $p21^{N-ras}$, and in particular, $p21^{K-rasB}$. Thus, in light of the present disclosure, a wide variety of peptidyl sequences having a farnesyl acceptor moiety are apparent. The use of $p21^{K-rasB}$, also termed simply, K-rasB, is currently preferred as mutations in K-rasB are by far the most frequent in human tumors.

As outlined above, the inventors have discovered that the farnesyltransferase enzyme is capable of binding to an affinity chromatography medium comprised of the peptide TKCVIM (SEQ ID NO:9), coupled to a suitable matrix. This feature of the farnesyltransferase enzyme was discovered by the present inventors in developing techniques for its isolation. Surprisingly, it has been found that the coupling of a peptide such as one which includes CVIM (SEQ ID NO:10), as does TKCVIM (SEQ ID NO:9), to a suitable chromatography matrix allows for the purification of the protein to a significant degree, presumably through interaction and binding of the enzyme to the peptidyl sequence. A basis for this interaction could be posited as due to the apparent presence of a farnesyl acceptor moiety within this peptide.

The phrase "capable of binding to an affinity chromatography medium comprised of TKCVIM coupled to a suitable matrix," is intended to refer to the ability of the protein to bind to such a medium under conditions as specified herein below. There will, of course, be conditions, such as when the pH is below 6.0, wherein the farnesyltransferase enzyme will not bind effectively to such a matrix. However, through practice of the techniques disclosed herein, one will be enabled to achieve this important objective.

There are numerous chromatography matrixes which are known in the art that can be applied to the practice of this invention. The inventors prefer to use activated CH-Sepharose® 4B, to which peptides such as TKCVIM (SEQ ID NO:9), or which incorporate the CVIM (SEQ ID NO:10) structure, can be readily attached and washed with little difficulty. However, the present invention is by no means limited to the use of CH-Sepharose® 4B, and subunit migrating slightly higher than the β subunit, which suggests that the α subunit may be slightly larger. From tryptic peptide sequence analyses and molecular cloning the nature of the α and β subunits as distinct proteins, encoded by separate genes, has been confirmed. Peptide sequences obtained from the rat brain subunits were subsequently found to be consistent with the amino acid sequences predicted by the DNA coding sequences:

TABLE I

Rat Farnesyltransferase Peptide Sequences

α subunit:

```
                                                                              *
1)  *  R  A  E  W  A  D  I  D  P  V  P  Q  N  D  G  P  S  P  V  V  Q  I  I  Y  S  K
    D                                                                              E
2)  D  A  I  E  L  N  A  A  N  Y  T  V  W  H  F  R
                                        *  *  *
3)  H  F  V  I  S  N  T  T  G  Y  S  D  H  R  R
                                        R  A  V
4)  V  L  V  E  W  L  K
5)  L  V  P  H  N  E  S  A  W  N  Y  L  K
                                        *  *
6)  L  W  D  N  E  L  Q  Y  V  D  Q  L  L  K
```

β subunit:

```
7)  *  A  Y  C  A  A  S  V  A  S  L  T  N  I  I  T  P  D  L  F  E  G  V  K  E
    S                                                                T  A
8)  *  L  L  Q  W  V  T  S  R  G
    S                          Q
9)  *  I  Q  A  T  T  H  F  L  Q  K  P  V  P  G  F  E  E  C  E  D  A  V  T  *  D  P
    V                                                                      S
10) I  Q  E  V  F  S  S  Y  K
11) F  E  G  G  F  Q  G  R
12) F  N  H  L  V  P  P  R
                   P
```

The sequences shown in Table I were obtained from HPLC-purified tryptic peptides isolated from the α- or β- subunit of purified rat farnesyltransferase (Reiss et al., 1991). Each peptide represents a pure species from a single HPLC peak. Asterisks denote ambiguous residues from amino acid sequencing. The amino acid sequences of all 6 peptides of each subunit (shown above) are found within continuous segments of the amino acid sequence predicted from the respective cDNA clones (SEQ ID NO:1; SEQ ID NO:3), except for the differences indicated below certain of the peptide sequences.

includes within its intended scope the use of any suitable matrix for performing affinity chromatography known in the art. Examples include solid matrices with covalently bound linkers, and the like, as well as matrices that contain covalently associated avidin, which can be used to bind peptides that contain biotin.

Farnesyltransferase enzymes of the present invention have typically been found to exhibit a molecular weight of between about 70,000 and about 100,000 upon gel filtration chromatography. For comparison purposes, this molecular weight was identified for farnesyl protein transferase through the use of a Superose 12 column, using a column size, sample load and parameters as described herein below.

It is quite possible, depending on the conditions employed, that different chromatographic techniques may demonstrate a farnesyltransferase protein that has an apparent molecular weight somewhat different than that identified using the preferred techniques set forth in the examples. It is intended therefore, that the molecular weight determination and range identified for farnesyltransferase in the examples which follow, are designated only with respect to the precise techniques disclosed herein.

It has been determined that the farnesyltransferase can be characterized as including two subunits, each having a molecular weight of about 45 to 50 kDa, as estimated by SDS polyacrylamide gel electrophoresis (SDS/PAGE). These subunits have been designated as α and β, with the α

The inventors have found that the holoenzyme forms a stable complex with all-trans [$^3$H]farnesyl pyrophosphate (FPP) that can be isolated by gel electrophoresis. The [$^3$]FPP is not covalently bound to the enzyme, and is released unaltered when the enzyme is denatured. When incubated with an acceptor such as p21$^{H\text{-}ras}$, the complex transfers [$^3$H]farnesyl from the bound [$^3$H]FPP to the ras protein. Furthermore, crosslinking studies have shown that p21$^{H\text{-}ras}$ binds to the β subunit, raising the possibility that the [$^3$H]FPP binds to the α subunit. If this is the case, it would invoke a reaction mechanism in which the α subunit act as a prenyl pyrophosphate carrier that delivers FPP to p21$^{H\text{-}ras}$, which is bound to the β subunit. Interestingly, the inventors have recently discovered that the α subunit is shared with another prenyltransferase, geranylgeranyltransferase-1, that attaches 20-carbon geranylgeranyl to, among others, Ras-related proteins.

An additional property discovered for prenyltransferase enzymes is that they can be inhibited by peptides or proteins, particularly short peptides, which include certain structural features, related in some degree to the farnesyl acceptor moiety discussed above. As used herein, the word "inhibited" refers to any degree of inhibition and is not limited for these purposes to only total inhibition. Thus, any degree of partial inhibition or relative reduction in farnesyltransferase, or even geranylgeranyltransferase activity is intended to be included within the scope of the term "inhibited." Inhibition in this context includes the phenomenon by which a chemical constitutes an alternate substrate for the enzyme, and is therefore farnesylated in preference to the ras protein, as well as inhibition where the compound does not act as an alternate substrate for the enzyme.

2. Preparation of Farnesyltransferase

The present invention is also concerned with techniques for the identification and isolation of farnesyltransferase enzymes, and particularly mammalian farnesyltransferases. Techniques are herein disclosed for the isolation of farnesyltransferase which are believed to be applicable to the purification of the native protein, or alternatively, to the purification of the recombinant enzyme following the molecular cloning and co-expression of the constituent subunits.

An important feature of the purification scheme disclosed herein involves the use of short peptide sequences which the inventors have discovered will bind the enzyme, allowing their attachment to chromatography matrices, such matrices may, in turn, be used in connection with affinity chromatography to purify the enzyme to a relative degree. Thus, in certain embodiments, the present invention is concerned with a method of preparing a farnesyltransferase enzyme which includes the steps of:

(a) preparing a cellular extract which includes the enzyme;

(b) subjecting the extract to affinity chromatography on an affinity chromatography medium to bind the enzyme thereto, the medium comprised of a farnesyltransferase binding peptide coupled to a suitable matrix;

(c) washing the medium to remove impurities; and (d) eluting the enzyme from the washed medium.

Thus, the first step of the purification protocol involves simply preparing a cellular extract which includes the enzyme. The inventors have discovered that the enzyme is soluble in buffers such as low-salt buffers, and it is proposed that virtually any buffer of this type can be employed for initial extraction of the protein from the tissue of choice or from recombinant cells in which the constituent subunits of the enzyme are expressed. The inventors prefer a 50 mM Tris-chloride, pH 7.5, buffer which includes a divalent chelator (e.g., 1 mM EDTA, 1 mM EGTA), as well as protease inhibitors such as phenylmethylsulphonyl fluoride (PMSF) and/or leupeptin. Of course, those of skill in the art will recognize that a variety of other types of buffers may be employed as extractants where desired, so long as the enzyme is extractable in such a buffer and its subsequent activity is not adversely affected to a significant degree.

In embodiments concerning the purification of the native enzyme, the choice of tissue from which one will seek to obtain the farnesyltransferase enzyme is not believed to be of crucial importance. In fact, it is believed that farnesyltransferases are components of virtually all living cells. Therefore, the tissue of choice will typically be that which is most readily available to the practitioner. In that farnesyltransferase action appears to proceed similarly in most systems studied, including, cultured hamster cells, rat brain, and even yeast, it is believed that this enzyme will exhibit similar qualities, regardless of its source of isolation.

In preferred purification embodiments, the inventors have isolated the native enzyme from rat brains in that this source is readily available. However, numerous other sources are contemplated to be directly applicable for isolation of the native enzyme, especially mammalian tissues such as liver, and human placenta, and also reticulocytes, or even yeast. Those of skill in the art, in light of the present disclosure, should appreciate that the techniques disclosed herein will be generally applicable to all such farnesyltransferases.

It will also be appreciated that the enzyme may be purified from recombinant cells prepared in accordance with the present invention. The techniques disclosed for the isolation of native farnesyltransferase are believed to be equally applicable to the purification of the protein from recombinant host cells, whether bacterial or eukaryotic, in which DNA segments encoding the selected constituent subunit has been expressed or co-expressed.

After the cell extract is prepared the enzyme is preferably subjected to two partial purification steps prior to affinity chromatography. These steps comprise preliminary treatment with 30% saturated ammonium sulfate which removes certain contaminants by precipitation. This is followed by treatment with 50% saturated ammonium sulfate, which precipitates the farnesyltransferase. The pelleted enzyme is then dissolved in a suitable buffer, such as 20 mM Tris-chloride (pH 7.5) containing 1 mM DTT and 20 $\mu$M $ZnCl_2$, dialyzed against the same buffer, and then subjected to further purification steps.

In preferred preparation embodiments, the dialyzed solution containing the enzyme is applied to a column containing an ion exchange resin such as Mono Q. After washing of the column to remove contaminants, the enzyme is eluted with a gradient of 0.25–1.0 M NaCl in the same buffer. The enzyme activity in each fraction is assayed as described below, and the fractions containing active enzyme are pooled and applied to the affinity column described below.

It is, of course, recognized that the preliminary purification steps described above are preferred laboratory procedures that might readily be replaced with other procedures of equivalent effect such as ion exchange chromatography on other resins or gel filtration chromatography. Indeed, it is possible that these steps could even be omitted and the crude cell extract might be carried directly to affinity chromatography.

After the preliminary purification steps, the extract may be subjected to affinity chromatography on an affinity chromatography medium which includes a farnesyltransferase binding peptide coupled to a suitable matrix. Typically, preferred farnesyltransferase binding peptides will comprise a peptide of at least 4 amino acids in length and will include a carboxyl terminal sequence of CAAX (SEQ ID NO:12), wherein:

C=cysteine;

A=an aliphatic or hydroxy amino acid; and

X=any amino acid.

Preferred binding peptides of the present invention which fall within the above general formula include structures such as CVIM (SEQ ID NO:10), CSIM (SEQ ID NO:13) and CAIM (SEQ ID NO:14), all of which structures are found to naturally occur in proteins which are believed to be acted upon by farnesyl protein transferases in nature. Particularly preferred are relatively short peptides, such as on the order of about 4 to about 10 amino acids in length which incorporate one of the foregoing binding sequences. Of particular preference is the peptide TKCVIM (SEQ ID NO:9), which has been effectively employed by the inventors in the isolation of farnesyl protein transferase.

The next step in the overall general purification scheme involves simply washing the medium to remove impurities. That is, after subjecting the extract to affinity chromatography on the affinity matrix, one will desire to wash the matrix in a manner that will remove the impurities while leaving the farnesyltransferase enzyme relatively intact on the medium. A variety of techniques are known in the art for washing matrices such as the one employed herein, and all such washing techniques are intended to be included within the scope of this invention. Of course, for washing purposes, one will not desire to employ buffers that will release or otherwise alter or denature the enzyme. Thus, one will typically want to employ buffers which contain non-denaturing detergents such as octylglucoside buffers, but will want to avoid buffers containing, e.g., chaotropic reagents which serve to denature proteins, as well as buffers of low pH (e.g., less than 7), or of high ionic strength (e.g., greater than 1.0 M), as these buffers tend to elute the bound enzyme from the affinity matrix.

After the matrix-bound enzyme has been sufficiently washed, for example in a medium-ionic strength buffer at essentially neutral pH, the specifically bound material can be eluted from the column by using a similar buffer but of reduced pH (for example, a pH of between about 4 and 5.5). At this pH, the enzyme will typically be found to elute from the preferred affinity matrices disclosed in more detail hereinbelow.

While it is believed that advantages in accordance with the invention can be realized simply through affinity chromatography techniques, additional benefits will be achieved through the application of additional purification techniques, such as gel filtration techniques. For example, the inventors have discovered that Sephacryl® S-200 high resolution gel columns can be employed with significant benefit in terms of protein purification. However, the present disclosure is by no means limited to the use of Sephacryl® S-200, and it is believed that virtually any type of gel filtration arrangement can be employed with some degree of benefit. For example, one may wish to use techniques such as gel filtration, employing media such as Superose®, agarose, or even Sephadex®.

Through the application of various of the foregoing approaches, the inventors have successfully achieved farnesyltransferase enzyme compositions of relatively high specific activity, measured in terms of ability to transfer farnesol from all-trans farnesyl pyrophosphate. For the purposes of the present invention, one unit of activity is defined as the amount of enzyme that transfers 1 pmol of farnesol from all-trans farnesyl pyrophosphate (FPP) into acid-precipitable $p21^{H\text{-}ras}$ per hour under the conditions set forth in Example I. Thus, in preferred embodiments the present invention is concerned with compositions of farnesyltransferase which include a specific activity of between about 5 and about 10 units/mg of protein. In more preferred embodiments, the present invention is concerned with compositions which exhibit a farnesyltransferase specific activity of between about 500 and about 600,000 units/mg of protein. Thus, in terms of the unit definition set forth above, the inventors have been able to achieve compositions having a specific activity of up to about 600,000 units/mg using techniques disclosed herein.

3. Cloning of Farnesyltransferase Subunits

Important aspects of the present invention concern isolated DNA segments and recombinant vectors encoding the α and β subunits of mammalian farnesyltransferases and the creation of recombinant host cells through the application of DNA technology, which express one, or preferably both, of these polypeptides.

As used herein, the term "DNA segment" in intended to refer to a DNA molecule which has been isolated free of total genomic DNA of a particular species. Therefore, a DNA segment encoding a subunit of farnesyltransferase is intended to refer to a DNA segment which contains such coding sequences yet is isolated away from total genomic DNA of the species from which the DNA is obtained. Included within the term "DNA segment", are DNA segments which may be employed in the preparation of vectors, as well as the vectors themselves, including, for example, plasmids, cosmids, phage, viruses, and the like.

In particular embodiments, the invention concerns isolated DNA segments and recombinant vectors incorporating DNA sequences which encode a farnesyltransferase subunit that includes within its amino acid sequence the amino acid sequence of SEQ ID NO:1 or SEQ ID NO:3, corresponding to rat brain farnesyltransferase subunits α and β, respectively. Moreover, in other particular embodiments, the invention concerns isolated DNA segments and recombinant vectors incorporating DNA sequences which encode a farnesyltransferase subunit that includes within its amino acid sequence the amino acid sequence of SEQ ID NO:5 or SEQ ID NO:7, corresponding to human farnesyltransferase subunits α and β, respectively. Recombinant vectors and isolated segments may therefore variously include the α or β subunit coding regions themselves, coding regions bearing selected alterations or modifications in the basic coding region or may encode larger polypeptides which nevertheless include sequences which will confer farnesyltransferase activity when said polypeptide is combined with the alternate subunit.

However, it will be understood that this aspect of the invention is not limited to the particular nucleic acid and amino acid sequences of SEQ ID NO:1 and SEQ ID NO:2 and SEQ ID NO:5 and SEQ ID NO:6 (α subunit) or SEQ ID NO:3 and SEQ ID NO:4 and SEQ ID NO:7 and SEQ ID NO:8 (β subunit). Accordingly, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

The recombinant cloning of cDNAs encoding the farnesyltransferase α and β subunits was achieved through the use of the peptide sequence information set forth above which was used in the preparation of subunit-specific oligonucleotides. Such oligonucleotides could be employed in the direct hybridization screening of a clone bank. However, the inventors preferred to use the peptide sequences in the preparation of primers for use in PCR amplification and partial sequencing of the selected subunit gene to confirm the underlying DNA sequence, and to prepare longer and more specific probes for use in clone bank screening.

In screening for the farnesyltransferase subunit-specific sequences, the inventors chose to use a cDNA clone bank prepared from poly A+ RNA. However, it is believed that the type of clone bank used is not crucial and that, if desired, one could employ a genomic clone bank. Similarly, in that the farnesyltransferase enzyme appears to be fairly ubiquitous in nature, it is believed that virtually any eukaryotic cell source may be employed for the preparation of RNA from which the clone bank is to be generated. One may mention by way of example, yeast, mammalian, plant, eukaryotic parasites and even viral-infected types of cells as the source of starting poly A+ RNA.

As the protein was initially purified from a mammalian source (rat), it is contemplated that particular advantages may be found in the use of mammalian cells, such as rat or human cell lines, as an RNA source. One may, of course, wish to first test such a cell line to ensure that relatively high levels of the farnesyltransferase enzyme are being produced by the selected cells. Rat brain, PC12 (a rat adrenal tumor cell line) and KNRK (a newborn rat kidney cell line) were preferred by the present inventors as they exhibited high levels of endogenous farnesyltransferase activity.

The type of cDNA clone bank used in the screening procedure is not believed to be particularly critical. However, one will likely find particular benefit through the preparation and use of a phage-based bank, such as λgt10 or λgt11, preferably using a particle packaging system. Phage-based cDNA banks are preferred because of the large numbers of recombinants that may be prepared and screened will relative ease. The manner in which the cDNA itself is prepared is again not believed to be particularly crucial. However, the inventors successfully employed both oligo dT and randomly primed cDNA, from a consideration of the difficulties which may arise in the reverse transcription of a large mRNA molecule.

Once a clone bank has been prepared, it may be screened in a number of fashions. For example, as mentioned above, one could employ the subunit peptide sequences set forth above for the preparation of nucleotide probes with which to directly screen the clone bank. A more preferable approach was found to be to use such sequences in the preparation of primers which may were used in PCR-based reactions to amplify and then sequence portions of the selected subunit gene, to thereby confirm the actual underlying DNA sequence, and to prepare longer and more specific probes for further screening. These primers may also be employed for the preparation of cDNA clone banks which are enriched for 3' and/or 5' sequences. This may be important, e.g., where less than a full length clone is obtained through the initially prepared bank.

If a less than full length clone was obtained on initial screening, the entire sequence could be subsequently obtained through the application of 5' and/or 3' extension technology, as required. The techniques for obtaining an extended farnesyltransferase subunit clone will be known to those of skill in the art in light of the present disclosure. The procedures used are those described in Frohman et al. (1988), involving a combination of reverse transcription, tailing with terminal deoxytransferase and, finally, PCR.

It is proposed that the DNA segments of the present invention may be employed for a variety of applications. For example, a particularly useful application concerns the recombinant production of the individual subunits or proteins or peptides whose structure is derived from that of the subunits, or in the recombinant production of the holoenzyme following co-expression of the two subunits. Additionally, the farnesyltransferase-encoding DNA segments of the present invention can also be used in the preparation of nucleic acid probes or primers, which can, for example, be used in the identification and cloning of farnesyltransferase genes or related genomic sequences, or in the study of subunit(s) expression, and the like.

4. Expression of Farnesyltransferase Subunits

Turning firstly to the expression of the cloned subunits. Once a suitable (full length if desired) clone or clones have been obtained, whether they be cDNA based or genomic, one may proceed to prepare an expression system for the recombinant preparation of one, or preferably both, of the subunits. The engineering of DNA segment(s) for expression in a prokaryotic or eukaryotic system may be performed by techniques generally known to those of skill in recombinant expression. It is believed that virtually any expression system may be employed in the expression of either or both subunits. Both subunits of the enzyme have been successfully co-expressed in eukaryotic expression systems with the production of active enzyme, but it is envisioned that bacterial expression systems may ultimately be preferred for the preparation of farnesyltransferase for all purposes. The cDNAs for both subunits have been separately expressed in bacterial systems, with the encoded proteins being expressed as fusions with *Schistosoma japonicum* glutathione S-transferase. It is believed that bacterial expression will ultimately have numerous advantages over eukaryotic expression in terms of ease of use and quantity of materials obtained thereby. Furthermore, it is proposed that co-transformation of host cells with DNA segments encoding both the α and β subunits will provide a convenient means for obtaining active enzyme. However, separate expression followed by reconstitution is also certainly within the scope of the invention. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of either, or preferably, both of the farnesyltransferase subunits, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes the enzyme, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

As noted above, it is proposed that in embodiments concerning the production of farnesyltransferase enzyme, the α and β subunits may be co-expressed in the same cell. This may be achieved by co-transfecting the cell with two distinct recombinant vectors, each bearing a copy of either the α- or β-encoding DNA. Alternatively, a single recombinant vector may be constructed to include the coding regions for both of the subunits, which could then be expressed in cells transfected with the single vector. In either event, the term "co-expression" herein refers to the expression of both the α and β subunits of farnesyltransferase in the same recombinant cell.

It is contemplated that virtually any of the commonly employed host cells can be used in connection with the expression of one, or preferably both, of the farnesyltransferase subunits in accordance herewith. Examples include cell lines typically employed for eukaryotic expression such as 239, AtT-20, HepG2, VERO, HeLa, CHO, WI 38, BHK, COS-7, RIN and MDCK cell lines. A preferred line for use in eukaryotic expression embodiments of the present invention has been found to be the human embryonic kidney cell line, 293.

In accordance with the general guidelines described above, a preferred method for expressing farnesyltransferase DNA has been found to be the transfection of human embryonic kidney 293 cells with expression vectors termed pFT-α or pFT-β. The pFT expression vectors are constructed from pCMV5, a plasmid that contains the promoter-enhancer region of the major immediate early gene of human cytomegalovirus (Andersson et al., 1989).

5. Nucleic Acid Hybridization

The DNA sequences disclosed herein will also find utility as probes or primers in nucleic acid hybridization embodiments. As such, it is contemplated that oligonucleotide fragments corresponding to the sequences of SEQ ID NO:2, SEQ ID NO:4, SEQ ID NO:6 and SEQ ID NO:8 for stretches of between about 10 nucleotides to about 30 nucleotides will find particular utility, with even longer sequences, e.g., 40, 50, 60, even up to full length, being even more particularly preferred. The ability of such nucleic acid probes to specifically hybridize to farnesyltransferase subunit-encoding sequences will enable them to be of use in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of farnesyltransferase genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and\or high temperature conditions, such as provided by 0.02 M–0.15 M NaCl at temperatures of 50° C. to 70° C. Such selective conditions tolerate little, if any, mismatch between the probe and the template or target strand, and would be particularly suitable for isolating farnesyltransferase genes.

Of course, for some applications, for example, where one desires to prepare mutants employing a mutant primer strand hybridized to an underlying template or where one seeks to isolate farnesyltransferase-encoding sequences for related species, functional equivalents, or the like, less stringent hybridization conditions will typically be needed in order to allow formation of the heteroduplex. In these circumstances, one may desire to employ conditions such as 0.15 M–0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one will likely desire to employ an enzyme tag such a urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

6. Biological Functional Equivalent Amino Acids

As mentioned above, modification and changes may be made in the structure of the farnesyltransferase subunits and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventors that various changes may be made in the sequence of the peptides (or underlying DNA) without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristics, these are: isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

As the relative hydropathic character of the amino acids determines the secondary structure of the resultant protein, which in turn defines the interaction of the protein with other molecules, for example, enzymes, substrates, inhibitors, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the side-chain substituents, for example, size, electrophilic character, charge, and the like. Exemplary substitutions which take various of the foregoing characteristics into consideration are well known to those of skill in the art and include: alanine, glycine and serine; arginine and lysine; glutamate and aspartate; serine and threonine; and valine, leucine and isoleucine.

While discussion has focused on functionally equivalent polypeptides arising from amino acid changes, it will be appreciated that these changes may be effected by alteration of the encoding DNA; taking into consideration also that the genetic code is degenerate and that two or more codons may code for the same amino acid.

7. Inhibitors of Farnesyltransferase

Of principal importance to the present invention is the discovery that proteins or peptides that incorporate a prenyl acceptor sequence, such as one of the acceptor sequences discussed above, function as inhibitors of prenyl protein transferases, and therefore may serve as a basis for anticancer therapy. In particular, it has been found that prenyl acceptor peptides can successfully function both as false substrates that serve to inhibit the prenylation of natural substrates such as $p21^{ras}$, and as direct inhibitors which are not themselves farnesylated. Compounds falling into the latter category are particularly important in that these compounds are "pure" inhibitors that are not consumed by the inhibition reaction and can continue to function as inhibitors. Both types of compounds constitute an extremely important aspect of the invention in that they provide a means for blocking farnesylation of $p21^{ras}$ proteins, for example, in affected cell systems.

The farnesyltransferase inhibitor embodiments of the present invention concern in a broad sense a peptide or protein other than $p21^{ras}$ proteins, lamin a or lamin b, or yeast mating factor a, which peptide or protein includes a prenyl acceptor sequence within its structure and is further capable of inhibiting the prenylation of $p21^{ras}$ and, in particular K-rasB, by a farnesyltransferase, or even by geranylgeranyltransferase-1.

In certain preferred embodiments, the farnesyltransferase inhibitor of the present invention will include a prenyl acceptor or inhibitory amino acid sequence having the amino acids CAAX (SEQ ID NO:12), wherein:

C=cysteine;

A=any aliphatic, aromatic or hydroxy amino acid; and

X=any amino acid.

Typically, the prenyl acceptor or inhibitory amino acid sequence will be positioned at the carboxyl terminus of the protein or peptide such that the cysteine residue is in the fourth position from the carboxyl terminus.

In certain preferred embodiments, the inhibitor will be a relatively short peptide such as a peptide from about 4 to about 10 amino acids in length. A particular preferred inhibitor tested is a tetrapeptide that incorporates the above-mentioned CAAX (SEQ ID NO:12) recognition structure. It is possible that even shorter peptides will ultimately be preferred for practice of the invention in that the shorter the peptide, the greater the uptake by such peptide by biological systems, and the reduced likelihood that such a peptide will be destroyed or otherwise rendered biologically ineffective prior to effecting inhibition. However, numerous suitable inhibitory peptides have been prepared and tested by the present inventors, and shown to inhibit enzymatic activities virtually completely, at reasonable concentrations, e.g., between about 1 and 3 μM (with 50% inhibitions on the order of 0.1 to 0.5 μM).

While, broadly speaking, it is believed that compounds exhibiting an $IC_{50}$ of between about 0.01 μM and 10 μM will have some utility as farnesyltransferase inhibitors, the more preferred compounds will exhibit an $IC_{50}$ of between 0.01 M and 1 μM. The most preferred compounds will generally have an $IC_{50}$ of between about 0.01 μM and 0.3 μM.

Exemplary peptides which have been prepared, tested and shown to inhibit farnesyltransferase, as exemplified by inhibiting farnesyltransferase at an $IC_{50}$ of between 0.01 and 10 μM include CVIM (SEQ ID NO:10); KKSKTKCVIM (SEQ ID NO:11); TKCVIM (SEQ ID NO:9); RASNR-SCAIM (SEQ ID NO:15); TQSPQNCSIM (SEQ ID NO:16); and the following tetrapeptides:

CIIM (SEQ ID NO:17); CVVM (SEQ ID NO:18); CVLS (SEQ ID NO:19); CVLM (SEQ ID NO:20); CAIM (SEQ ID NO:14); CSIM (SEQ ID NO:13); CCVQ (SEQ ID NO:21); CIIC (SEQ ID NO:22); CIIS (SEQ ID NO:23); CVIS (SEQ ID NO:24); CVIA (SEQ ID NO:25); CLIL (SEQ ID NO:27); CLLL (SEQ ID NO:28); CTVA (SEQ ID NO:29); CVAM (SEQ ID NO:30); CKIM (SEQ ID NO:31); CLIM (SEQ ID NO:32); CFIM (SEQ ID NO:33); CVFM (SEQ ID NO:34); CVIF (SEQ ID NO:35); CEIM (SEQ ID NO:36); CGIM (SEQ ID NO:37); CPIM (SEQ ID NO:38); CVYM (SEQ ID

NO:39); CVTM (SEQ ID NO:40); CVPM (SEQ ID NO:41); CVSM (SEQ ID NO:42); CVIV (SEQ ID NO:43); CVIP (SEQ ID NO:44); CVII (SEQ ID NO:45); CVWM (SEQ ID NO:46); CIFM (SEQ ID NO:47).

A variety of peptides have been synthesized and tested such that now the inventors can point out peptide sequences having particularly high inhibitory activity, i.e., wherein relatively lower concentrations of the peptides will exhibit an equivalent inhibitory activity ($IC_{50}$). Interestingly, it has been found that slight changes in the sequence of the acceptor site can result in loss of inhibitory activity. Thus, when TKCVIM is changed to TKVCIM, the inhibitory activity of the peptide is reversed. Similarly, when a glycine is substituted for one of the aliphatic amino acids in CAAX, a decrease in inhibitory activity is observed. However, it is proposed that as long as the general formula as discussed above is observed, one will achieve a structure that is inhibitory to farnesyltransferase. Furthermore, the testing of a candidate inhibitory peptide is straightforward given the assay methods disclosed herein.

A particularly important discovery is the finding that the incorporation of an aromatic residue such as phenylalanine, tyrosine or tryptophan into the third position of the CAAX (SEQ ID NO:12) sequence will result in a "pure" inhibitor. As used herein, a "pure" farnesyltransferase inhibitor is intended to refer to one which does not in itself act as a substrate for prenylation by the enzyme. This is particularly important in that the inhibitor is not consumed by the inhibition process, leaving the inhibitor to continue its inhibitory function unabated.

Exemplary compounds that have been tested and found to act as pure inhibitors include CVFM (SEQ ID NO:34), CVWM (SEQ ID NO:46), CVYM (SEQ ID NO:39), CIFM (SEQ ID NO:47), CV(pCl-F)M, L-penicillamine-VFM, and L-penicillamine-VIM. Pure inhibitors will therefore incorporate an inhibitory amino acid sequence rather than an acceptor sequence, with the inhibitory sequence characterized generally as having an aromatic moiety associated with the penultimate carboxyl terminal amino acid, whether it be an aromatic amino acid or another amino acid which has been modified to incorporate an aromatic structure (Goldstein et al., 1991).

Importantly, the pure inhibitor CVFM (SEQ ID NO:34) is the best inhibitor identified to date by the inventors. It should be noted that the related peptide, CFIM (SEQ ID NO:33) is not a "pure" inhibitor; its inhibitory activity is due to its action as a substrate for farnesylation.

The potency of CVFM peptides as inhibitors of the enzyme may be enhanced by attaching substituents such as fluoro, chloro or nitro derivatives to the phenyl ring. An example is parachlorophenylalanine, which has been tested and found to have "pure" inhibitory activity. It may also be possible to substitute more complex hydrophobic substances for the phenyl group of phenylalanine. These would include naphthyl ring systems.

The present inventors propose that additional improvements can be made in pharmaceutical embodiments of the inhibitor by including within their structure moieties which will improve their hydrophobicity, which it is proposed will improve the uptake of peptidyl structures by cells. Thus, in certain embodiments, it is proposed to add fatty acid or polyisoprenoid side chains to the inhibitor which, it is believed, will improve their lipophilic nature and enhance their cellular uptake.

Other possible structural modifications include the addition of benzyl, phenyl or acyl groups to the amino acid structures, preferably at a position sufficiently removed from the prenyl acceptor site, such as at the amino terminus of the peptides. It is proposed that such structures will serve to improve lipophilicity. In this regard, the inventors have found that N-acetylated and N-octylated peptides such as modified CVIM retain much of their inhibitory activity, whereas S-acetoamidated CVIN appears to lose much of its inhibitory activity.

The invention also contemplates that modifications can be made in the structure of inhibitory proteins or peptides to increase their stability within the body, such as modifications that will reduce or eliminate their susceptibility to degradation, e.g., by proteases. For example, the inventors contemplate that useful structural modifications will include the use of amino acids which are less likely to be recognized and cleaved by proteases, such as the incorporation of D-amino acids, or amino acids not normally found in proteins such as ornithine or taurine. Other possible modifications include the cyclization of the peptide, derivatization of the NH groups of the peptide bonds with acyl groups, etc.

8. Assays For Farnesyltransferase

In still further embodiments, the invention concerns a method for assaying farnesyltransferase activity in a composition. This is an important aspect of the invention in that such an assay system provides one with, not only the ability to follow the isolation and purification of native or recombinant enzymes, but also the ability to develop screening assays for candidate inhibitors of farnesyltransferase enzymes, discussed in more detail below.

As used herein, the term "prenyltransferase," is intended to refer to any enzyme that transfers a prenyl group from one moiety to another. CAAX prenyltransferase, is intended to refer to any enzyme that transfers a prenyl group from one moiety to another, wherein the acceptor moiety comprises a four amino acid sequence of CAAX (SEQ ID NO:12), as defined above, at the carboxyl terminus. The preferred example of a CAAX prenyltransferase is farnesyltransferase, but geranylgeranyltransferase-1 is also included within this term.

The assay methods of the invention, generally include determining the ability of a composition suspected of having farnesyltransferase activity to catalyze the transfer of a farnesyl group to an acceptor protein or peptide. A farnesyl acceptor protein or peptide is generally defined as a protein or peptide that will act as a substrate for farnesyltransferase and which includes a recognition site such as CAAX, as defined above. In preferred embodiments, a $p21^{ras}$ protein is used as the acceptor protein, with the use of K-rasB preparations being particularly preferred as acceptor moieties.

Typically, the assay protocol is carried out using all-trans farnesyl pyrophosphate as the prenyl donor in the reaction. One will find particular benefit in constructing an assay wherein a label is present on the farnesyl moiety of an all-trans farnesyl pyrophosphate, in that one can measure the appearance of such a label, for example, a radioactive label, in the farnesyl acceptor protein or peptide, such as K-RasB. A geranylgeranyl group may even be used as the prenyl moiety, as this is also transferred by CAAX prenyltransferases to CAAX prenyl acceptor proteins or peptides, such as K-rasB.

As with the characterization of the enzyme discussed above, the prenyl acceptor sequence which are employed in connection with the assay are generally defined by CAAX (SEQ ID NO:12), with preferred embodiments including sequences such as CVIM (SEQ ID NO:10), CSIM (SEQ ID NO:13), CAIM (SEQ ID NO:14), etc., all of which have been found to serve as useful enzyme substrates. Indeed, it is believed that most proteins or peptides that include a carboxyl terminal sequence of CAAX (SEQ ID NO:12) can be successfully employed in prenyl protein transferase assays. However, in certain preferred embodiments, sequences that include a lysine rich region immediately upstream of CAAX (SEQ ID NO:12), and in particular a lysine rich region followed by CVIM (SEQ ID NO:10) are preferred.

For use in these assays, a preferred prenyl acceptor protein or peptide will be a p21$^{ras}$ protein, and most preferably, a K-ras B protein or peptide. This is particularly true where one seeks to identify inhibitor substances, as discussed in more detail below, which function either as "false acceptors" in that they divert prenylation away from natural substrates by acting as substrates in and or themselves, or as "pure" inhibitors which are not in themselves prenylated. The advantage of employing a natural substrate such as p21$^{ras}$ is several fold, but includes the ability to separate the natural substrate from the false substrate to analyze the relative degrees of prenylation.

In the most preferred embodiments, the prenyl acceptor protein is a K-rasB protein, polypeptide or peptide. Not only does this have the advantage of being a natural substrate as described above, but the present inventors have surprisingly discovered that both CAAX prenyltransferase enzymes have a higher affinity for K-rasB than for H-Ras. Furthermore, K-rasB is less sensitive than H-Ras to inhibition by certain inhibitors, and so would be less susceptible to non-specific effects and false positives. Finally, K-RasB is the form of aberrant ras protein most often found in human cancers (Babacid, 1987), which means that the use of H-Ras in assays designed to identify inhibitors for ultimate clinical use, is less than optimal. Therefore, K-RasB is a better prenyl acceptor protein for use in assays to identify inhibitors of farnesylation and even geranylgeranylation.

However, for the purposes of simply assaying enzyme specific activity, e.g., assays which do not necessarily involve differential labeling or inhibition studies, one can readily employ short peptides as a prenyl acceptor in such protocols, such as peptides from about 4 to about 14 amino acids in length which incorporate the recognition signal at their carboxyl terminus. Exemplary prenyl acceptor protein or peptides include but are not limited to CVIM (SEQ ID NO:10); KKSKTKCVIM (SEQ ID NO:11); TKCVIM (SEQ ID NO:9); RASNRSCAIM (SEQ ID NO:15); TQSPQNCSIM (SEQ ID NO:16); CIIM (SEQ ID NO:17); CVVM (SEQ ID NO:18); CVLS (SEQ ID NO:19); KKKKKKSKTCVIM (SEQ ID NO:73); KKKKKKSKSCKCVLS (SEQ ID NO:75) and DESGPGCMSCKCVIM (SEQ ID NO:74).

9. Assays for Candidate Substances

In still further embodiments, the present invention concerns methods for identifying new prenyltransferase inhibitory compounds, which may be termed as "candidate substances." It is contemplated that these screening techniques will prove useful in the general identification of any compound that will serve the purpose of inhibiting farnesyltransferase. It is further contemplated that useful compounds in this regard will in no way be limited to proteinaceous or peptidyl compounds. In fact, it may prove to be the case that the most useful pharmacologic compounds for identification through application of the screening assay will be non-peptidyl in nature and, e.g., which will be recognized and bound by the enzyme, and serve to inactivate the enzyme through a tight binding or other chemical interaction.

Thus, in these embodiments, the present invention is directed to method for determining the ability of a candidate substance to inhibit a prenyltransferase enzyme, preferably farnesyltransferase, which methods generally include the steps of:

(a) obtaining an enzyme composition comprising a farnesyltransferase enzyme that is capable of transferring a farnesyl moiety to a K-rasB protein, polypeptide or peptide;

(b) obtaining a substrate composition comprising a K-rasB protein or peptide;

(c) admixing the enzyme composition with the substrate composition, and further admixing the resultant enzyme-substrate composition with a farnesyl pyrophosphate compound and a candidate substance; and (d) determining the ability of the farnesyltransferase to transfer a farnesyl moiety to the K-rasB protein or peptide in the presence of the candidate substance and in the absence of the candidate substance.

By determining the ability of farnesyltransferase to transfer a farnesyl moiety to a K-rasB protein or peptide both in the presence and in the absence of the candidate substance, one is able to determine the ability of the candidate substance to inhibit the farnesyltransferase enzyme. The method is equally suitable for use in assays using farnesyltransferase enzyme compositions in combination with farnesyl pyrophosphate and geranylgeranyltransferase-1 enzyme compositions and geranylgeranyl pyrophosphate. Although not currently preferred, it is contemplated that geranylgeranyltransferase maybe used in assays with either of the foregoing prenyl groups as it exhibits dual specificity.

In using farnesyltransferase, or even geranylgeranyltransferase-1 enzyme compositions, one will generally prepare a relatively purified form of the enzyme, whether from native or recombinant sources. This is an important aspect of the candidate substance screening assay in that without at least a relatively purified preparation, one will not be able to assay specifically for enzyme inhibition, as opposed to the effects of the inhibition upon other substances in the extract which then might affect the enzyme.

Native or recombinant farnesyltransferase may be purified, as described herein, from virtually any living cell. Basically, the process involves: preparing a cellular extract that includes the enzyme; subjecting the extract to affinity chromatography on an affinity chromatography medium to bind the enzyme thereto, the medium comprised of a farnesyltransferase binding peptide coupled to a suitable matrix; washing the medium to remove impurities; and eluting the enzyme from the washed medium.

Geranylgeranyltransferase-1 may also be purified in a similar manner to that as described for farnesyltransferase. However, there are alternative purification methods for both geranylgeranyltransferase-1 and farnesyltransferase. In one embodiment the method of purification may include multiple chromatographic steps without affinity chromatography (Yokoyama et al., 1991), another may include multiple chromatographic steps followed by affinity purification (Zhang et al., 1994 and Examples I and V, as disclosed herein). The type of medium used for the affinity chromatographic step may be varied as desired.

The source of enzyme for purification may be from natural sources or following expression in a recombinant host cell.

DNA segments encoding the shared farnesyltransferase and geranylgeranyltransferase α subunit is well known and exemplified herein, by SEQ ID NO:2 and SEQ ID NO:4. DNA segments encoding the β subunit of farnesyltransferase is also disclosed herein, by SEQ ID NO:6 and SEQ ID NO:8. The geranylgeranyltransferase-1 β subunit sequence is also known. For example, Zhang et al. (1994; incorporated herein by reference) describes both human and rat β subunit sequences. The DNA and amino acid sequences of the geranylgeranyltransferase-1 β subunit are also disclosed herein. SEQ ID NO:79 and SEQ ID NO:81 correspond to human and rat DNA sequences, respectively, and SEQ ID NO:78 and SEQ ID NO:80 correspond to human and rat amino acid sequence, respectively.

In one embodiment, a recombinant geranylgeranyltransferase-1 is prepared as a fusion protein with six histidine residues at the NH$_2$-terminus. The process involves the preparation of nucleic acids that encode for both the α and β subunits of geranylgeranyltransferase-1, wherein one of the subunits has been fused to a nucleic acid sequence corresponding to a string of histidine residues (Example V, as disclosed herein). This recombinant nucleic acid is then transfected into a suitable system where high level expression of the fusion protein ensues. Preferably, the fusion protein is co-transfected with its converse subunit and the two proteins expressed simultaneously to produce a functional geranylgeranyltransferase-1. A preferred expression system is disclosed herein, using baculovirus as the vector that infects *Spodoptera frugiperda* (Sf9) cells, which in turn, expresses the recombinant protein. After infection, Sf9 cells are collected by centrifugation, and washed. The cells are then lysed and the lysate is centrifuged. The supernatant may then be further purified by various chromatographic techniques or immediately subjected to Ni$^{2+}$-Sepharose® affinity chromatography as described by Cremers et al. (1994; incorporated herein by reference).

It is generally preferred that the farnesyltransferase or even geranylgeranyltransferase enzyme compositions be in a relatively purified form to achieve advantageous results in these assays. Methods for achieving the required purity are well known to those in the art and are described herein in significant detail.

In the present candidate screening assays, the substrate composition, i.e., the composition that includes the prenyl acceptor moiety, will be a composition that includes a K-rasB protein or peptide. K-rasB is preferred, as the majority of Ras-related human cancers contain oncogenic versions of K-rasB (Babacid, 1987). Furthermore, K-rasB is recognized as a substrate by both farnesyltransferase and geranylgeranyltransferase-1 at a high affinity. K-rasB is also less sensitive, than H-Ras, to inhibition by certain inhibitors, and so would be less likely to produce false positives results.

The term "K-rasB protein or peptide", as used herein, refers to any protein, polypeptide or peptide containing a CAAX carboxyl terminal sequence (SEQ ID NO:12), and preferably CVIM (SEQ ID NO:10), generally preceded by a lysine rich region. A "lysine rich region" is defined herein as any region of between about 5 or 6 and about 30 residues in length, wherein about one third or more of the amino acid residues are lysine. Preferably, a lysine rich region is a region of between about 5 or 6 and about 20 residues in length, wherein about one half or more of the amino acid residues are lysine. Most preferably, lysine rich regions will be between about 6 and about 12 residues in length, and will have sequences wherein between about two thirds and about three quarters, or more, of the amino acid residues are lysine.

In the native K-rasB sequence, the lysine rich region (KKKKKKSK, SEQ ID NO:77) is found immediately in front of the CVIM sequence (SEQ ID NO:10). The two sequences together give the wild type K-rasB carboxyl terminal sequence KKKKKKSKCVIM (SEQ ID NO:73). This is one preferred example of a "K-rasB sequence", i.e., a CAAX prenyl acceptor sequence of four residues preceded by a lysine rich sequence of eight residues, which contains seven lysines.

Any protein, polypeptide or peptide that contains SEQ ID NO:73, or an equivalent thereof, is considered to be a K-rasB protein, polypeptide or peptide in terms of the present invention, so long as it still functions as a prenyltransferase substrate and still accepts a prenyl moiety, and preferably, a farnesyl moiety. That is, so long as other sequence elements do not, by virtue of length, secondary or tertiary structure or primary sequence, negate or counteract the function of the prenyl acceptor and lysine rich sequences.

Even where the sequence of SEQ ID NO:73 is to be substantially used, as in a near-native K-rasB protein or a synthetic peptide, these K-rasB proteins and peptides are not limited to the presence of SEQ ID NO:73 itself. Certain modifications or changes may be made to this sequence and the protein or peptide would still be considered a K-rasB protein or peptide, as long as the protein or peptide retains like or otherwise desirable substrate and acceptor characteristics.

The preferred types of amino acid modification or changes that may be made to a K-rasB protein or peptide are described in detail hereinabove, under "Biological Functional Equivalent Amino Acids." Certain modifications or changes may include amino acid omissions from, or additions to, both the lysine rich region and the CAAX consensus motif. The distance between these sequences may also be varied, e.g., from zero to about five or so intervening residues. The length of protein or peptide containing such a sequence may, therefore, vary from a minimum of about 8 or 9 residues to a number limited only by structural constraints.

The desirable characteristic desired in a K-rasB protein or peptide in connection with the present invention, is the ability of the sequence to be recognized by one, or preferably, by both CAAX prenyltransferase enzymes and to act as an acceptor of a prenyl moiety.

In order to test whether a molecule has the desirable characteristics all that is required is that the molecule is included in an assay as disclosed herein (Example V), and determine whether it acts as a substrate for one or both of the two prenyl transferase enzymes and accepts prenyl groups.

K-rasB proteins and peptides may be prepared and purified by various processes. For larger polypeptides, including full-length and even longer K-rasB sequences, recombinant methods will generally be preferred. The DNA sequences encoding K-rasB are well known in the art, for example, as disclosed by Shimizu et al. (1983), McGrath et al. (1983), Capon et al. (1983), McCoy et al. (1984), Yamamoto et al. (1985) and Barbacid (1987). Each of the foregoing references, and specifically their figures, are incorporated herein by reference for the purposes of describing K-rasB DNA and amino acid sequences.

In addition to the teachings in the art, as described above, K-rasB sequences are also included herein. SEQ ID NO:83 and SEQ ID NO:85 are examples of human K-RasB DNA sequences, and SEQ ID NO:82 and SEQ ID NO:84 are examples of amino acid sequences of human K-rasB. As is known in the art, and particularly described by Capon et. al. (1983) and McGrath et al. (1983), the human gene is alternatively spliced and the translated protein may include one of two forms of exon IV. SEQ ID NO:83 and SEQ ID NO:82 correspond to the DNA and amino acid sequences of one form of human K-RasB, and SEQ ID NO:85 and SEQ ID NO:84 correspond to the DNA and amino acid sequences of the second human K-RasB, with sequence changes in exon IV.

Using sequence information, PCR protocols and/or conventional cloning techniques may be used to produce nucleic acids with appropriate sequences. K-rasB encoding vectors may be expressed in effective expression systems. A currently preferred system is the expression of a recombinant K-rasB sequence in *E. coli* as a fusion protein with 6 histidine residues at the $NH_2$-terminus, as described herein in Example V.

The K-rasB substrate or acceptor compositions, whether obtained from native or recombinant sources, and whether protein or peptide, will preferably be obtained at a greater than about 85–90%, or even 95% purity.

The amounts of K-RasB in an assay will preferably vary over a range of about 0 (as a control) to 100 μm, and more preferably, of about 0 (as a control) to 25 μm. This will of course depend on the type and purity of the K-rasB protein and the amount and type of inhibitor included in the assay.

The candidate screening assay is quite simple to set up and perform, and is related in many ways to the assay discussed above for determining enzyme activity. Thus, after obtaining a relatively purified preparation of the enzyme, either from native or recombinant sources, and a K-rasB protein or peptide-containing substrate composition, one will generally admix the enzyme and substrate preparations. One will then add the labeled prenyl pyrophosphate, preferably radioactively-labeled and incubate for 10 to 30 minutes or one hour, at 37° C. The amount of labeled prenyl group transferred to the substrate K-rasB protein or peptide will then be measured by separating the substrate from solution. This can be accomplished by various methods including TLC, filtration, gel electrophoresis, column chromatography and, preferably, ethanol precipitation.

The enzyme and substrate compositions will preferably be admixed under conditions that would normally allow the enzyme to perform its intended function, i.e., transfer of a prenyl group to a K-rasB substrate, but for the inclusion of a inhibitory substance. In this fashion, one can measure the ability of the candidate substance to reduce prenylation of K-rasB in the presence of the candidate substance, relative to its transferase ability in the absence of the candidate substance. Accordingly, one will desire to measure or otherwise determine the activity of the relatively purified enzyme in the absence of the added candidate substance relative to the activity in the presence of the candidate substance in order to assess the relative inhibitory capability of the candidate substance.

Any candidate substance that consistently reduces the activity of a CAAX prenyltransferase enzyme particularly, farnesyltransferase, below control levels, i.e., below the designated 100% value in the absence of the candidate substance, will be "an inhibitor" as defined herein. Moreover, useful inhibitors, including potentially clinically useful inhibitors, will preferably have a significant inhibitory effect. A "significant inhibitory effect," as used herein, will be defined as the ability to reduce farnesyltransferase activity to about 55 through 95%, preferably about 25 through 75%, and more preferably to about 5 through 25%, or even below, as compared to the 100% value in the absence of the candidate inhibitory substance.

10. Methods of Inhibiting Farnesyltransferase

In still further embodiments, the present invention is concerned with methods for inhibiting farnesyltransferase enzymes, which methods generally include subjecting a farnesyltransferase enzyme to an effective amount or concentration of a farnesyltransferase inhibitor, such as one of the family of peptidyl compounds discussed above, or with a candidate substance identified in accordance with the candidate screening assay embodiments. This is, of course, an important aspect of the invention in that it is believed that by inhibiting the farnesyltransferase enzyme, one will be enabled to treat various aspects of cancers, such as K-rasB-related cancers.

It is believed that the use of such inhibitors to block the attachment of prenyl groups to ras proteins in malignant cells of patients suffering with cancer or pre-cancerous states will serve to treat or palliate the cancer, and may be useful by themselves or in conjunction with other cancer therapies, including chemotherapy, resection, radiation therapy, and the like. This is particularly true for inhibitors of prenylation of K-rasB. As the majority of Ras-related human cancers involve oncogenic versions of K-rasB, inhibition of its activity, will have very significant consequences for cancer therapy.

BRIEF DESCRIPTION OF THE DRAWINGS

FIG. 16A. cDNA Probes Generated from a Knowledge of the Amino Acid Sequences of Peptides Derived from Rat Farnesyltransferase α and β Subunits. Primer α1 (SEQ ID NO:57) and Primer α2 (SEQ ID NO:58) were used in PCR with rat genomic DNA to obtain the nucleotide sequence encoding the amino acid sequence of the peptide shown (SEQ ID NO:59), as described in Example III. The nucleotide sequence 5'-ATIGAGTTAAACGCAGCCAACTATACGGTCTGGCACTT (a specific example in accordance with residues 6–54 of SEQ ID NO:64), was used as a probe to screen a rat brain cDNA library.

FIG. 16C. cDNA Probes Generated from a Knowledge of the Amino Acid Sequences of Peptides Derived from Rat Farnesyltransferase α and β Subunits. Nucleotide sequence encoding the peptide as derived from the above PCR (SEQ ID NO:62). Primer β3 and primer β4, the sequences of which are contained entirely within SEQ ID NO:62, were synthesized and used as the primers for 3'-end amplification of the cDNA, as described in Example III.

FIG. 17. Identification of the Amino Acids Within the Sequence of Rat Farnesyltransferase a Subunit (FT-α) (SEQ ID NO:1) which are Identical with those within the Sequence of Yeast RAM2. Amino acid residues are numbered on the left. Identical amino acids are boxed. The sequence of yeast RAM2 has been reported by He et al. (1991), and the non-identical residues are not shown.

FIG. 18. Identification of the Amino Acid Within the Sequence of Rat Farnesyltransferase β-Subunit (FT-β) (SEQ ID NO:3) which are Identical with those within the Sequence of Yeast DPR1/RAM1. Amino acid residues are numbered on the left. Identical amino acids are boxed. The sequence of yeast DPR1/RAM1 has been reported by Goodman et al. (1988), and the non-identical residues are not shown.

FIG. 23. Nucleotide Sequence (SEQ ID NO:6) and Deduced Amino Acid Sequence (SEQ ID NO:5) of a Full Length cDNA Encoding the Human Farnesyltransferase α Subunit, and Comparison with the Amino Acid Sequence of the Rat α Subunit. Amino acids are numbered on the left. Amino acid residue 1 is the putative initiator methionine. The translated 379 amino acid sequence of the human farnesyltransferase α subunit protein (SEQ ID NO:5) is shown beneath the nucleotide sequence (SEQ ID NO:6). Amino acid residues that differ from the rat protein are boxed and the corresponding amino acids in the rat sequence are shown below the human sequence.

FIG. 25. COOH-terminal sequences of wild-type and chimeric Ras proteins used in this study. All wild-type proteins and wild-type amino acid sequences are given in regular type. Bold type denotes K-rasB derived sequences substituted into H-Ras proteins. All sequences are those of human proteins.

FIG. 25).

DETAILED DESCRIPTION OF THE PREFERRED EMBODIMENTS

Figure 1A:
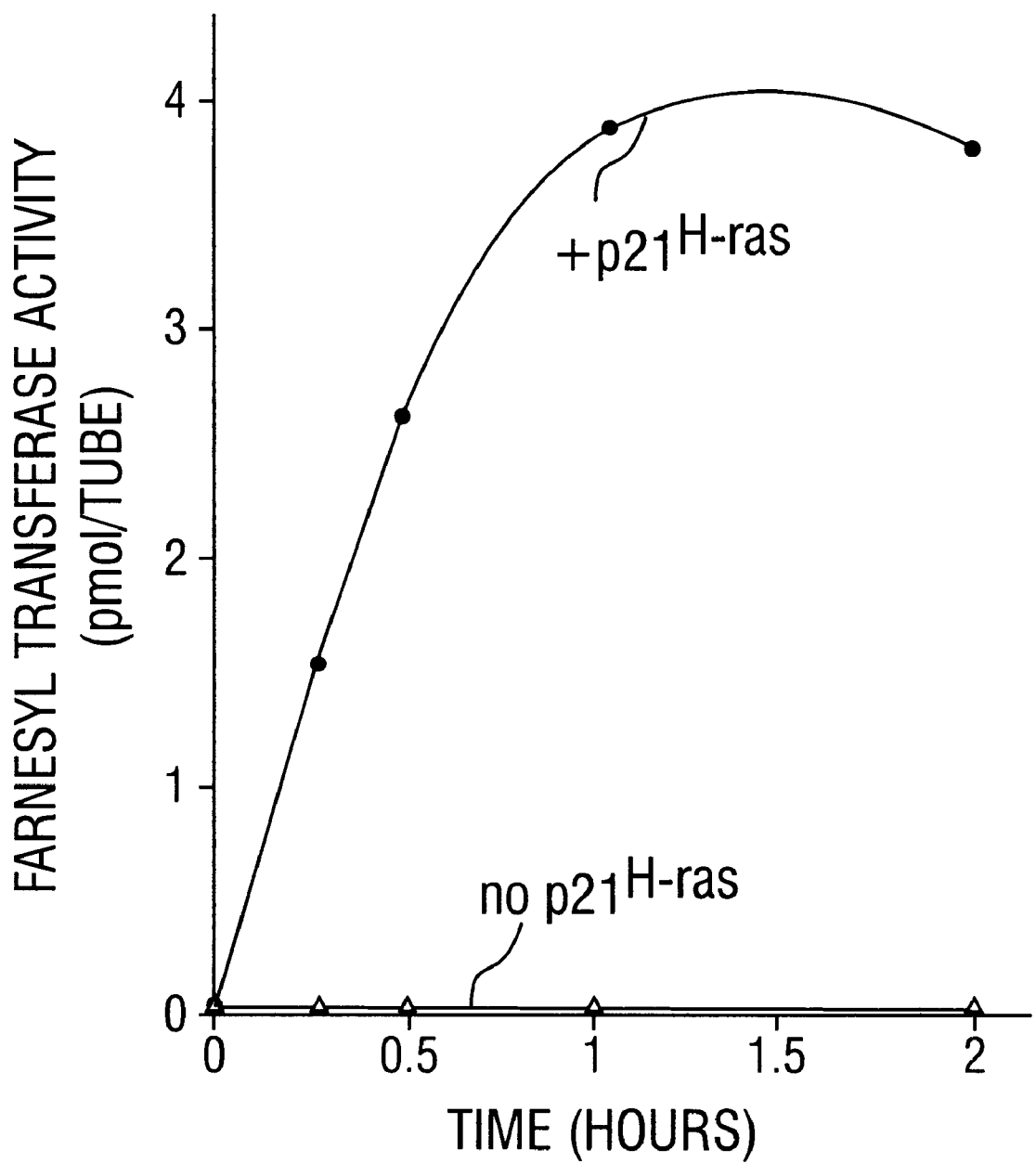
FIG. 1A. Transfer of Farnesol from [$^3$H]FPP to p21$^{H-ras}$ by Partially Purified Rat Brain Farnesyltransferase. Each standard assay mixture contained 10 pmoles of [$^3$H]FPP and 3.5 μg of partially purified farnesyltransferase in the absence (▲) or presence (●) of 40 μM p21$^{H-ras}$. Duplicate samples were incubated for the indicated time at 37° C., and TCA-precipitable radioactivity was measured as described in the Examples.

The following examples illustrate techniques discovered by the inventors for the identification and purification of mammalian farnesyl protein transferase enzymes, as well as techniques for their assay and for the screening of new compounds which may be employed to inhibit such enzymes. These studies also demonstrate a variety of peptidyl compounds which themselves can be employed to inhibit these enzymes. It should be appreciated by those of skill in the art that the techniques disclosed in the examples which follow represent laboratory techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Preparation and Characterization of Farnesyltransferase

1. Materials

Peptides were obtained from Peninsula Laboratories or otherwise synthesized by standard techniques. All peptides were purified on HPLC, and their identity was confirmed by amino acid analysis. Just prior to use, each peptide was dissolved at a concentration of 0.8 mM in 10 mM dithiothreitol (DTT), and all dilutions were made in 10 mM DTT. Unlabeled all-trans farnesyl pyrophosphate (FPP) was synthesized by the method of Davisson, et al. (1986). [1-³H] Farnesyl pyrophosphate (20 Ci/mmol) was custom synthesized by New England Nuclear. Geraniol and farnesol (both all-trans) were obtained from Aldrich Chemical. All-trans geranylgeraniol was obtained from R. Coates (University of Illinois).

Recombinant wild type human $p21^{H-ras}$ protein was produced in a bacterial expression system with pAT-rasH (provided by Channing J. Der, La Jolla Cancer Research Foundation, La Jolla, Calif.), an expression vector based on pXVR (Feig et al., 1986). The plasmid was transformed into E. coli JM105, and the recombinant $p21^{H-ras}$ protein was purified at 4° C. from a high speed supernatant of the bacterial extracts by sequential chromatography on DEAE-Sephacel® and Sephadex® G-75. Purity was ~90% as judged by Coomassie blue staining of SDS gels. Purified $p21^{H-ras}$ was concentrated to 15 mg/ml in 10 mM Trischloride (pH 7.5) containing 1 mM DTT, 1 mM EDTA, 3 mM $MgCl_2$, and 30 μM GDP and stored in multiple aliquots at −70° C.

2. Assay for Farnosyltransforase Activity

Farnesyltransferase activity was determined by measuring the amount of ³H-farnesol transferred from all-trans ³H]farnesyl pyrophosphate ([³H]FPP) to $p21^{H-ras}$ protein. The standard reaction mixture contained the following concentrations of components in a final volume of 25 μl: 50 mM Tris-chloride (pH 7.5), 50μM $ZnCl_2$, 20 mM KCl, 1 mM DTT, and 40 μM $p21^{H-ras}$. The mixture also contained 10 pmoles of [3H]FPP (~30,000 dpm/pmol) and 1.8–3.5 μg of partially purified farnesyltransferase (see below). After incubation for 1 hour at 37° C. in 12×75-mm borosilicate tubes, the reaction was stopped by addition of 0.5 ml of 4% SDS and then 0.5 ml of 30% trichloroacetic acid (TCA).

The tubes were vortexed and left on ice for 45–60 min, after which 2 ml of a 6% TCA/2% SDS solution were added. The mixture was filtered on a 2.5-cm glass fiber filter with a Hoefer filtration unit (FH 225). The tubes were rinsed twice with 2 ml of the same solution, and each filter was washed five times with 2 ml of 6% TCA, dried, and counted in a scintillation counter. One unit of activity is defined as the amount of enzyme that transfers 1 pmol of [$^3$H]farnesol from [$^3$H]FPP into acid-precipitable p21$^{H\text{-}ras}$ per hour under the standard conditions.

3. Purification of Farnesyltransferase

All steps were carried out at 4° C. except where indicated:

Step 1—Ammonium Sulfate Fractionation: Brains from 50 male Sprague-Dawley rats (100–150 g) were homogenized in 100 ml of ice-cold buffer containing 50 mM Tris-chloride (pH 7.5), 1 mM EDTA, 1 mM EGTA, 0.2 mM phenylmethylsulfonyl fluoride (PMSF), and 0.1 mM leupeptin, and the extract was spun at 60,000×g for 70 min. The supernatant was brought to 30% saturation with solid ammonium sulfate, stirred for 30 min on ice, and centrifuged at 12,000×g for 10 min to remove precipitated proteins. The resulting supernatant was adjusted to 50% saturation with ammonium sulfate, and the resulting pellet was dissolved in ~20 ml of 20 mM Tris-chloride (pH 7.5) containing 1 mM DTT and 20 $\mu$M ZnCl$_2$ and dialyzed for 4 hours against 4 liters of the same buffer and then 4 liters of fresh buffer of the same composition for 12 hours. The dialyzed material was divided into multiple aliquots and stored at −70° C.

Step 2—Ion-exchange Chromatography: A portion of the 30–50% ammonium sulfate fraction (200 mg protein) was chromatographed on a Mono Q 10/10 column using an FPLC system (Pharmacia LKB Biotechnology). The column was run as described in the legend to FIG. 5. Fractions eluting between 0.3 and 0.4 M NaCl contained the majority of the transferase activity. These fractions were pooled, divided into multiple aliquots, and stored at −70° C.

Step 3—Affinity Chromatography: An affinity column containing a peptide corresponding to the COOH-terminal six amino acids of p21$^{K\text{-}rasB}$ protein was prepared as follows. Fifteen mg of the peptide TKCVIM (SEQ ID NO:9) were coupled to 1 g of activated CH-Sepharose® 4B (Pharmacia LKB Biotechnology) according to the manufacturer's instructions. The resulting 2.5-ml slurry was poured into a column, and excess uncoupled peptide was removed by 10 cycles of alternating washes, each consisting of 40 column volumes of 0.1 M sodium acetate (pH 4.0) and then 0.1 M Tris-chloride (pH 8.0). Both buffers contained 1 M NaCl and 10 mM DTT. The column was stored at 4° C. in 20 mM Tris-chloride (pH 7.2) and 0.02% sodium azide. Fifteen mg of Mono Q-purified material in 10 ml were applied to a 1-ml peptide column equilibrated in 50 mM Tris-chloride (pH 7.5) containing 0.1 M NaCl and 1 mM DTT (Buffer A). The enzyme-containing solution was cycled through the column three times at room temperature. The column was washed with 20 ml of Buffer A containing 0.2% (w/v) octyl-β-D-glucopyranoside (Buffer B). The enzyme was eluted with 20 ml of 50 mM Tris-succinate (pH 5.0) containing 1 mM DTT, 0.1 M NaCl, and 0.2% octyl-β-D-glucopyranoside. The pH 5 eluate was concentrated and washed twice with a 10-fold excess of Buffer B in a CF25 Centriflo ultrafiltration cone (Amicon) and brought to 1 ml (10-fold concentration relative to the starting material).

Step 4—Gel Filtration: Affinity-purified farnesyltransferase (~1 $\mu$g) was chromatographed on a Superose 12 column as described in the legend to FIG. 7A.

In the enzyme characterization studies of FIG. 1A, FIG. 1B, FIG. 2A, FIG. 2B, FIG. 3, FIG. 4A, FIG. 4B, FIG. 8 and FIG. 9, a partially purified fraction of farnesyltransferase was used. This enzyme was prepared by Steps 1 and 2 as described above, after which 6 mg of the Mono Q-purified material was concentrated to 2 ml and then loaded onto a 1.6×50-cm Sephacryl® S-200 high resolution gel filtration column (Pharmacia LKB Biotechnology). The column was equilibrated with 50 mM Tris-chloride (pH 7.5) containing 1 mM DTT, 0.2 M NaCl, 20 $\mu$M ZnCl$_2$, and 0.2% octyl-β-glucopyranoside and eluted with the same buffer at a flow rate of 15 ml/hour. Only the peak fraction, containing 1 mg protein and 40% of initial activity, was used for studies.

4. Identification of $^3$H-Isoprenoid Transferred from [$^3$H]FPP

A modification of the procedure described by Casey et al. (Casey et al., 1989) was employed as follows: Briefly, two standard transferase reactions of 25-$\mu$l each were conducted for 1 hour at 37° C. The mixtures were then pooled, and a 25-$\mu$l aliquot from the 50-$\mu$l pooled sample was diluted to 250 $\mu$l with 2% (w/v) SDS. This mixture was precipitated with an equal volume of 30% TCA, filtered through nitrocellulose, (7 mm disc), washed twice with 250 $\mu$l 6% TCA/2% SDS followed by five washes with 5% TCA, digested with 8 $\mu$g trypsin, and subjected to cleavage with methyl iodide. The released $^3$H-isoprenoids were extracted into chloroform/methanol and chromatographed on a reverse-phase HPLC system as described in the legend to FIG. 4A and FIG. 4B.

5. Other Methods

SDS polyacrylamide gel electrophoresis was carried out as described by Laemmli (1970). Gels were calibrated with high range SDS-PAGE standards (Bio-Rad). Protein content of extracts was measured by the method of Lowry, et al. (Lowry et al., 1951) except for that of the affinity-purified material, which was estimated by comparison to the bovine serum albumin marker (M$_r$ 66,000) following SDS gel electrophoresis and Coomassie staining.

6. Results and Discussion

Figure 1B:
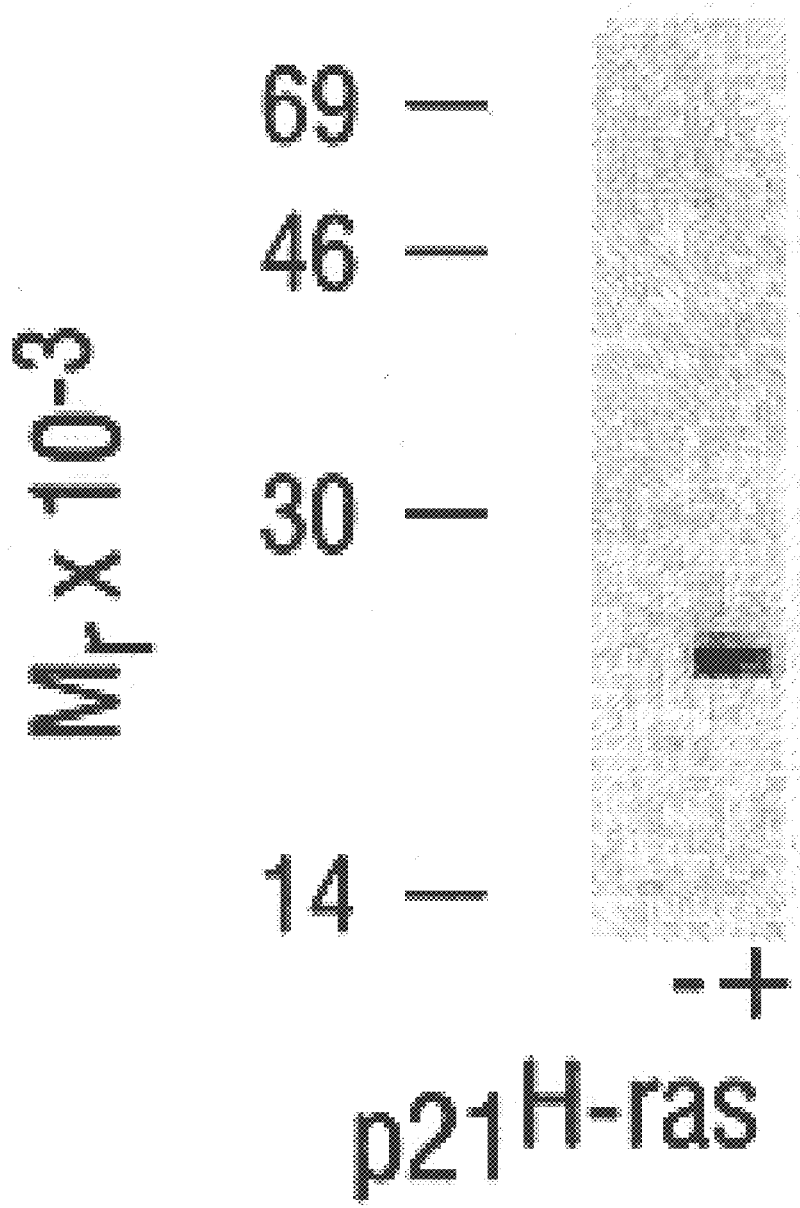
FIG. 1B. Transfer of Farnesol from [$^3$H]FPP to p21$^{H-ras}$ by Partially Purified Rat Brain Farnesyltransferase. The migration on a 12% SDS polyacrylamide gel of an aliquot from a reaction carried out, as described in FIG. 1A, for 1 h in the absence or presence of p21$^{H-ras}$. The gel was treated with Entensify solution (DuPont), dried, and exposed to XAR film for 2 days at −70° C.
Figure 2A:
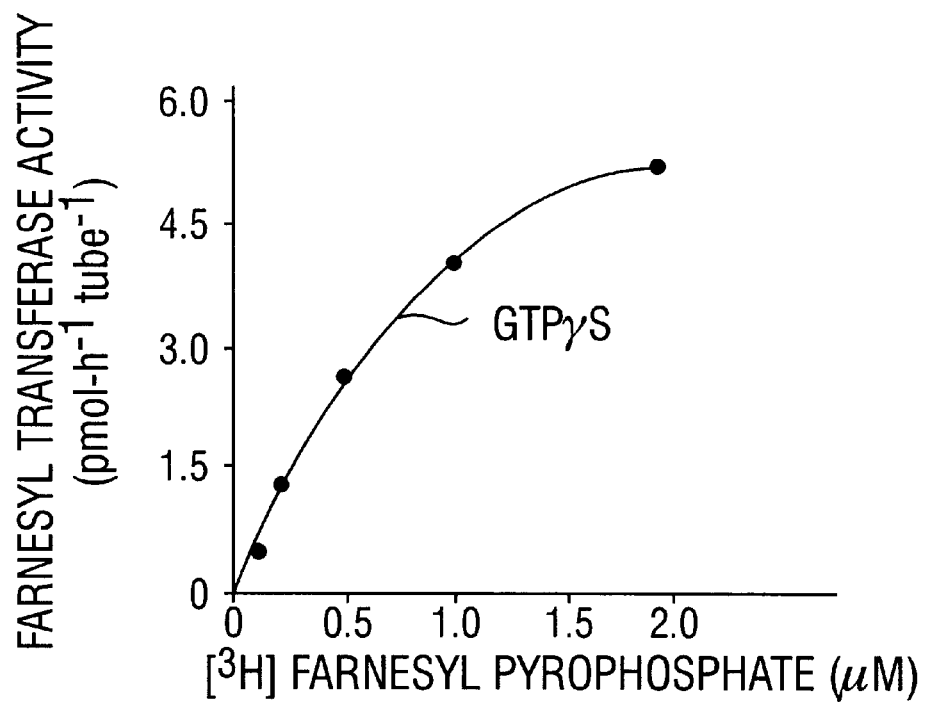
FIG. 2A. Substrate Saturation Curves for Farnesyltransferase. Each standard reaction mixture contained 1.8 μg of partially purified farnesyltransferase, 40 μg p21$^{H-ras}$, [$^3$H] FPP (250,000 dpm); and varying amounts of unlabeled FPP to give the indicated final concentration of [$^3$H]FPP.
Figure 2B:
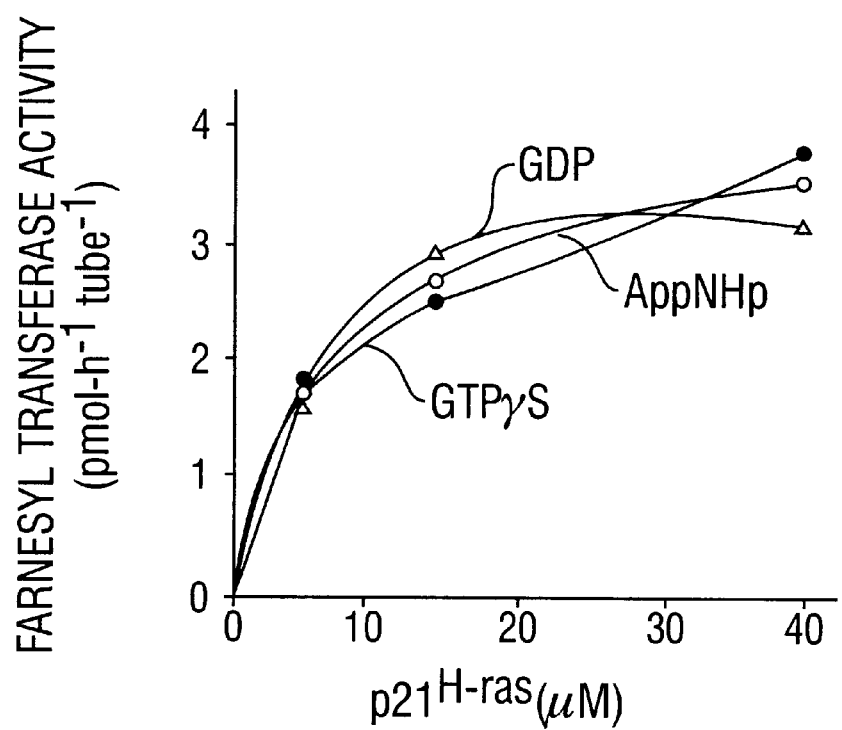
FIG. 2B Substrate Saturation Curves for Farnesyltransferase. Each standard reaction mixture contained 3.2 μg partially purified farnesyltransferase, 10 pmol [$^3$H]FPP, and the indicated concentration of p21$^{H-ras}$ that had been incubated with 50 μM of the indicated nucleotide for 45 min at 30° C. and then passed through a G-50 Sephadex® gel filtration column at room temperature in buffer containing 10 mM Tris-chloride (pH 7.7), 1 mM EDTA, 1 mM DTT, and 3 mM $MgCl_2$. Assays were carried out in duplicate for 1 hour at 37° C., and TCA-precipitable radioactivity was measured as described in the Example.

As an initial attempt to identify a farnesyl protein transferase enzyme, rat brain cytosol was fractionated with ammonium sulfate and the active fraction subjected to ion exchange chromatography on a Mono Q column followed by gel filtration on Sephacryl® S-200. FIG. 1A shows that the active fraction from this column incorporated radioactivity from [$^3$H]farnesol into trichloroacetic acid precipitable p21$^{H\text{-}ras}$ in a time-dependent fashion at 37° C. The incorporated radioactivity could be visualized as a band of the expected molecular weight of ~21 kDa on SDS polyacrylamide gels (FIG. 1B). The concentration of [$^3$H]farnesyl pyrophosphate that gave half-maximal reaction velocity was approximately 0.5 $\mu$M (FIG. 2A). The half-maximal concentration for p21$^{Hras}$ was approximately 5 $\mu$M, and there was no difference when the p21$^{H\text{-}ras}$ was equilibrated with a nonhydrolyzable GTP or ATP analogue or with GDP (FIG. 2B).

Figure 3:
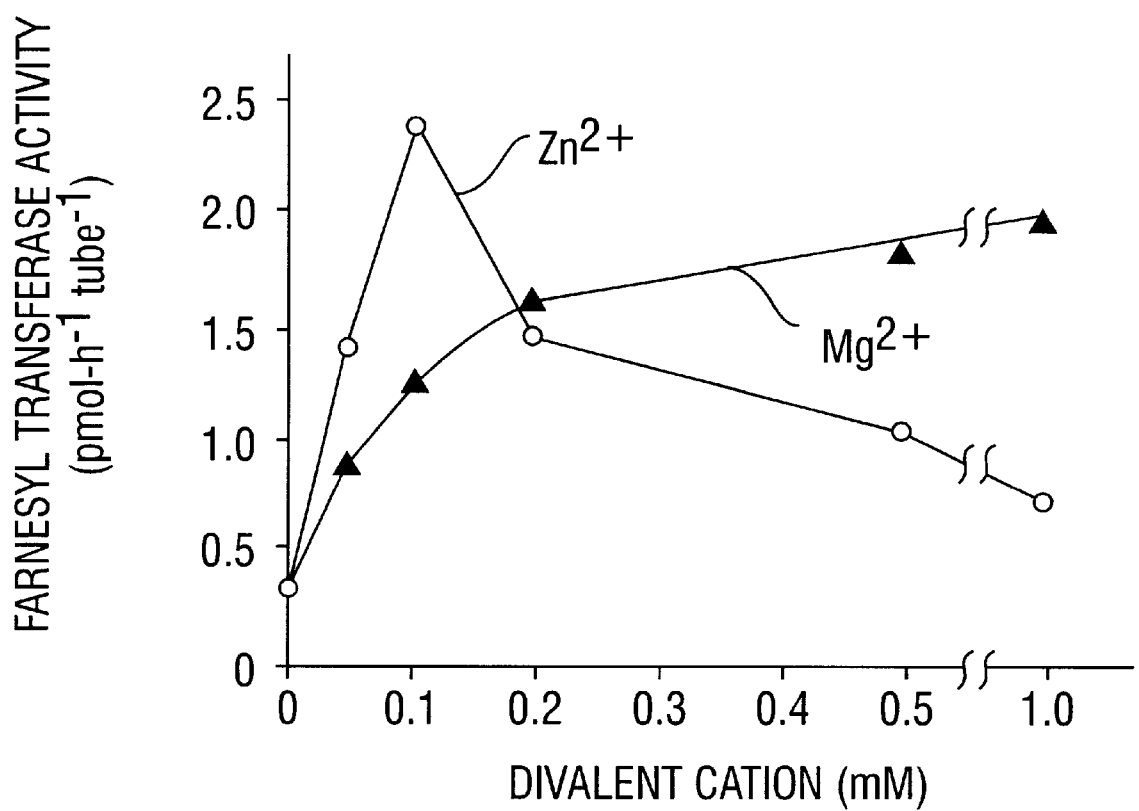
FIG. 3. Divalent Cation Requirement for Farnesyltransferase. Each standard reaction mixture contained 10 pmol [$^3$H]FPP, 2.5 μg of partially purified farnesyltransferase, 40 μM p21$^{H-ras}$, 0.15 mM EDTA, and the indicated concentrations of either $ZnCl_2$ (●) or $MgCl_2$ (▲). Incubations were carried out in duplicate for 1 hour at 37° C., and TCA-precipitable radioactivity was measured as described in the Examples.

With p21$^{H\text{-}ras}$ as a substrate, the transferase reaction was inhibited by 0.15 mM EDTA, and this inhibition was reversed by 0.1 to 1.0 mM concentrations of zinc or magnesium chloride (FIG. 3). At higher concentrations of zinc chloride, inhibition was observed.

Figure 4A:
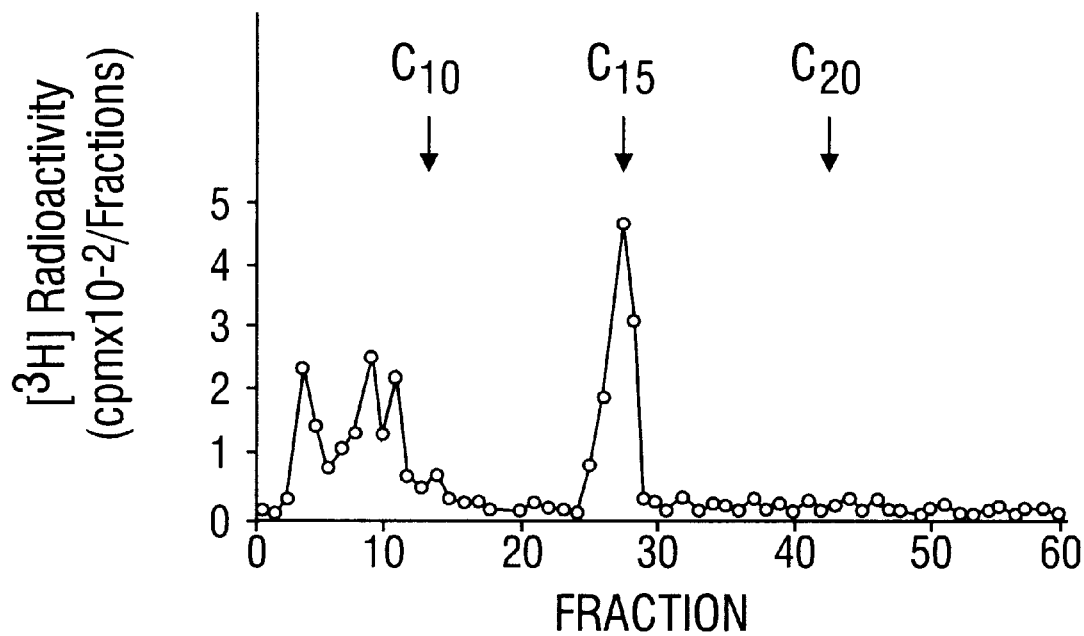
FIG. 4A. Identification of [$^3$H]FPP-derived Radioactive Material Transferred to p21$^{H-ras}$. An aliquot from a standard reaction mixture was subjected to cleavage with methyl iodide as described in the Examples. After cleavage, the extracted material was dried under nitrogen, resuspended in 0.4 ml of 50% (v/v) acetonitrile containing 25 mM phosphoric acid and 6 nmoles of each isoprenoid standard as indicated. The mixture was subjected to reverse phase HPLC (C18, Phenomex®) as described by Casey, et al. (1989) except that an additional 10-min wash with 100% acetonitrile/phosphoric acid was used. The isoprenoid standards were identified by absorbance at 205 nm: $C_{10}$, all-trans geraniol; $C_{15}$, all-trans farnesol; $C_{20}$, all-trans geranylgeraniol.
Figure 4B:
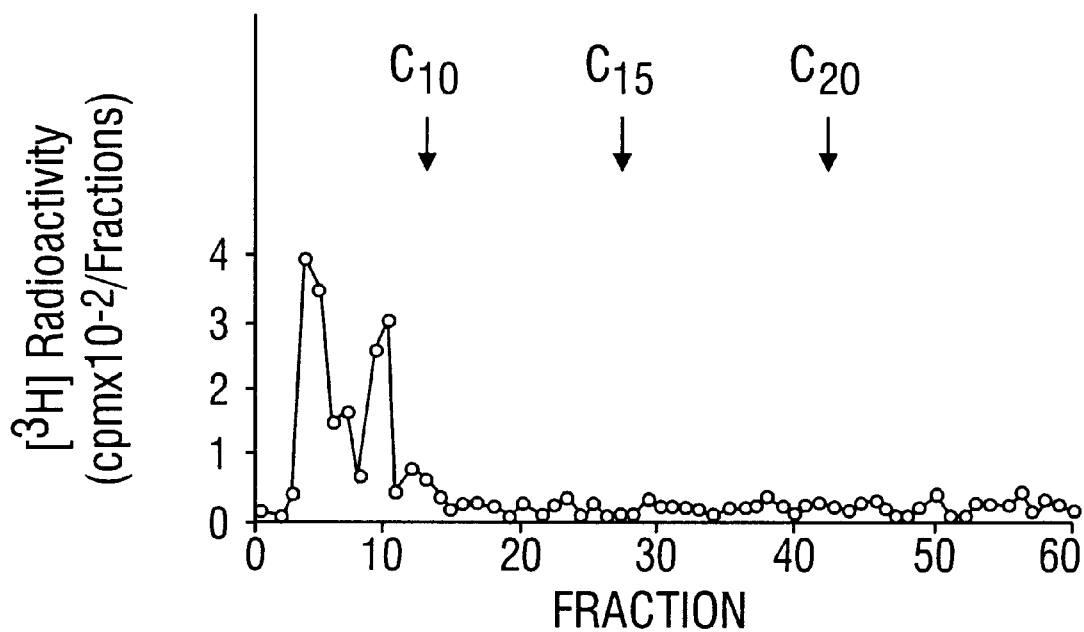
FIG. 4B. Identification of [$^3$H]FPP-derived Radioactive Material Transferred to p21$^{H\text{-}ras}$. Another aliquot was treated identically as described in FIG. 4A, except methyl iodide was omitted.

To confirm that the transferred material was [$^3$H]farnesol, the washed trichloracetic acid-precipitated material was digested with trypsin, the radioactivity released with methyl iodide, and the products subjected to reverse-phase HPLC. The methyl iodide-released material co-migrated with an authentic standard of all-trans farnesol (C$_{15}$) (FIG. 4A). Some radioactivity emerged from the column prior to the geraniol standard (C$_{10}$), but this was the same in the presence and absence of methyl iodide treatment. This early-eluting material was believed to represent some tryptic peptides whose radioactivity was not released by methyl iodide.

Figure 5:
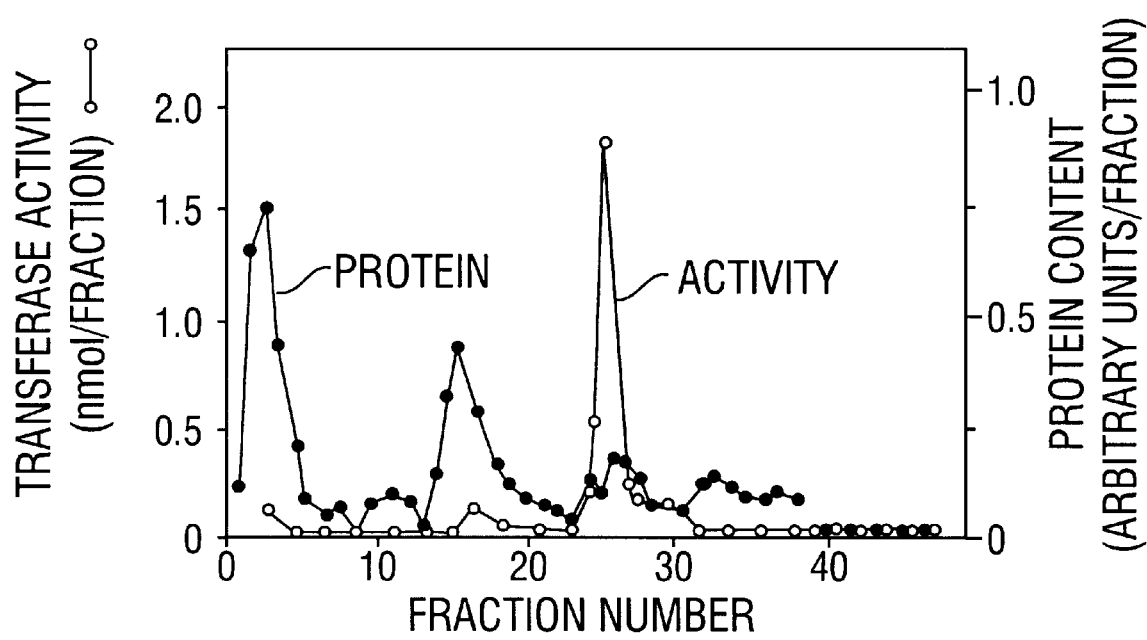
FIG. 5. Chromatography of Farnesyltransferase on a Mono Q Column. The 30–50% ammonium sulfate fraction from rat brain (200 mg) was applied to a Mono Q column (10×1-cm) equilibrated in 50 mM Tris-chloride (pH 7.5) containing 1 mM DTT, 20 μM $ZnCl_2$, and 0.05 M NaCl. The column was washed with 24 ml of the same buffer containing 0.05 M NaCl, followed by a 24-ml linear gradient from 0.05 to 0.25 M NaCl, followed by a second wash with 24 ml of the same buffer containing 0.25 M NaCl. The enzyme was then eluted with a 112-ml linear gradient of the same buffer containing 0.25–1.0 M NaCl at a flow rate of 1 ml/min. Fractions of 4 ml were collected. An aliquot of each fraction (2 μl) was assayed for farnesyltransferase activity by the standard method (○). The protein content of each fraction (●) was estimated from the absorbance at 280 nm.

FIG. 5 shows the elution profile of farnesyltransferase activity from a Mono Q column. The activity appeared as a single sharp peak that eluted at approximately 0.35 M sodium chloride.

The peak fractions from the Mono Q column were pooled and subjected to affinity chromatography on a column that contained a covalently-bound peptide corresponding to the carboxyl-terminal 6-amino acids of p21$^{K\text{-}rasB}$. All of the farnesyltransferase activity was adsorbed to the column, and about 50% of the applied activity was recovered when the column was eluted with a Tris-succinate buffer at pH 5.0.

Table II summarizes the results of a typical purification procedure that started with 50 rat brains. After ammonium sulfate precipitation, mono Q chromatography, and affinity chromatography, the farnesyltransferase was purified approximately 61,000-fold with a yield of 52%. The final specific activity was about 600,000 units/mg.

Figure 6A:
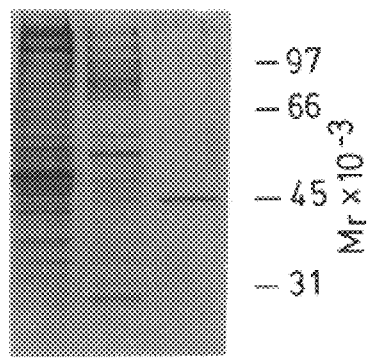
FIG. 6A. SDS Polyacrylamide Gel Electrophoresis of Farnesyltransferase at Various Stages of Purification. 10 μg of the 30–50% ammonium sulfate fraction (lane 1), 3 μg of the Mono Q fraction (lane 2), and approximately 90 ng of the peptide affinity-column fraction (lane 3) were subjected to SDS-10% polyacrylamide gel electrophoresis, and the protein bands were detected with a silver stain. The farnesyltransferase activity in each sample loaded onto the gel was approximately 0.1, 0.8, and 54 units/lane for lanes 1, 2, and 3, respectively. The molecular weights for marker protein standards are indicated. Conditions of electrophoresis: 10% mini gel run at 30 mA for 1 hour.
Figure 6B:
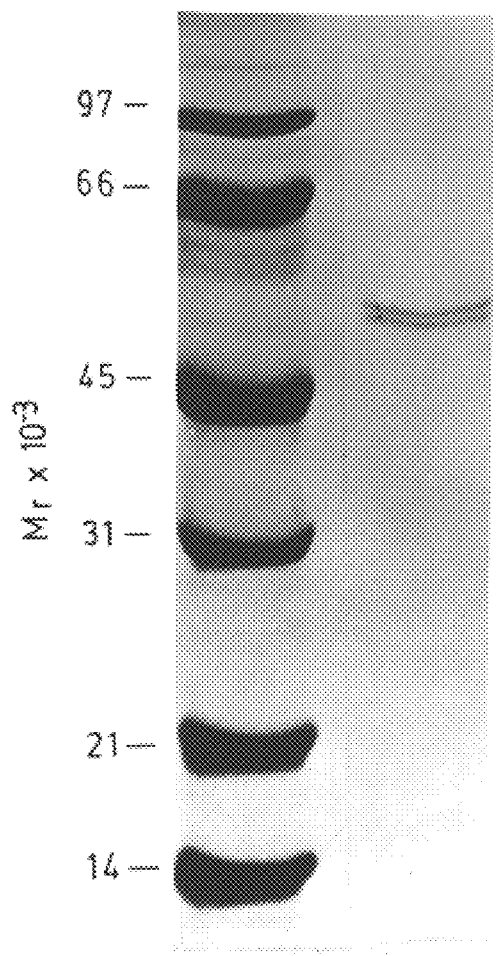
FIG. 6B. SDS Polyacrylamide Gel Electrophoresis of Purified Farnesyltransferase. 0.7 μg of the peptide affinity-purified-column fraction (right lane) was subjected to SDS-10% polyacrylamide gel electrophoresis, and the protein bands were detected with a Coomassie Blue Stain. The molecular weights for marker protein standards (left lane) are indicated.

FIG. 6A shows the SDS gel electrophoretic profile of the proteins at each stage of this purification as visualized by silver staining. The peptide affinity column yielded a single protein band with an apparent subunit molecular weight of 50,000. When the purified enzyme was subjected to SDS gel electrophoresis under more sensitive conditions, the 50-kDa protein could be resolved into two closely spaced bands that were visualized in approximately equimolar amounts (FIG. 6B).

Figure 7A:
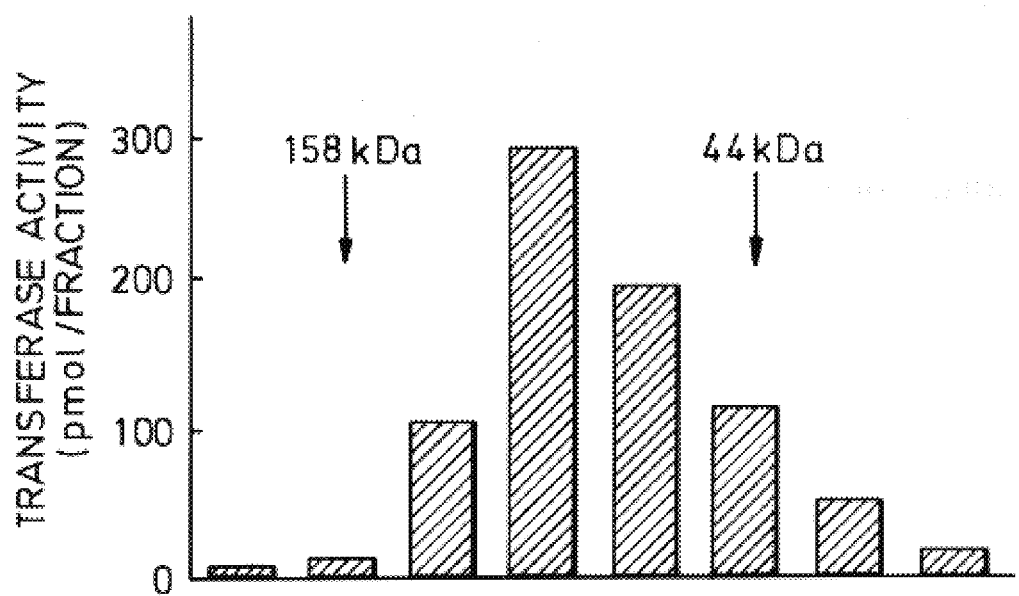
FIG. 7A. Gel Filtration of Farnesyltransferase. Affinity-purified farnesyltransferase (~1 μg protein) was subjected to gel filtration on a Superose-12 column (25×0.5-cm) in 50 mM Tris-chloride (pH 7.5) containing 0.2 M NaCl, 1 mM DTT, and 0.2% octyl-β-D-glucopyranoside at a flow rate of 0.2 ml/min. Fractions of 0.5 ml were collected. A 6-μl aliquot of each fraction was assayed for farnesyltransferase activity by the standard method except that each reaction mixture contained 0.2% octyl-β-D-glucopyranoside. The column was calibrated with thyroglobulin (670 kDa), γ-globulin (158 kDa), ovalbumin (44 kDa), myoglobin (17 kDa), and vitamin B12 (1.35 kDa). Arrows indicate the elution position of the 158-kDa and 44-kDa markers.
Figure 7B:
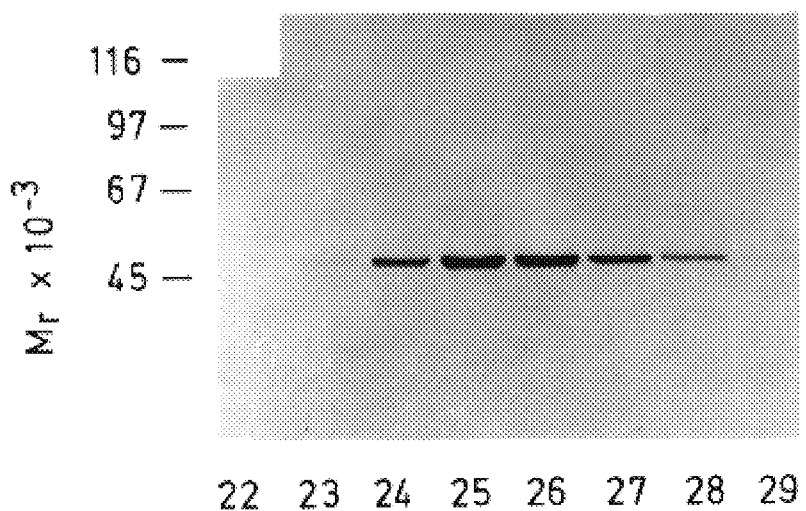
FIG. 7B. Gel Filtration of Farnesyltransferase. Conditions are described in FIG. 7A. A 0.42-ml aliquot of each fraction was concentrated to 40 μl with a Centricon 30 Concentrator (Amicon), and 25 μl of this material was then subjected to electrophoresis on an 10% SDS polyacrylamide gel. The gel was stained with silver nitrate and calibrated with marker proteins (far-right lane).
Figure 8:
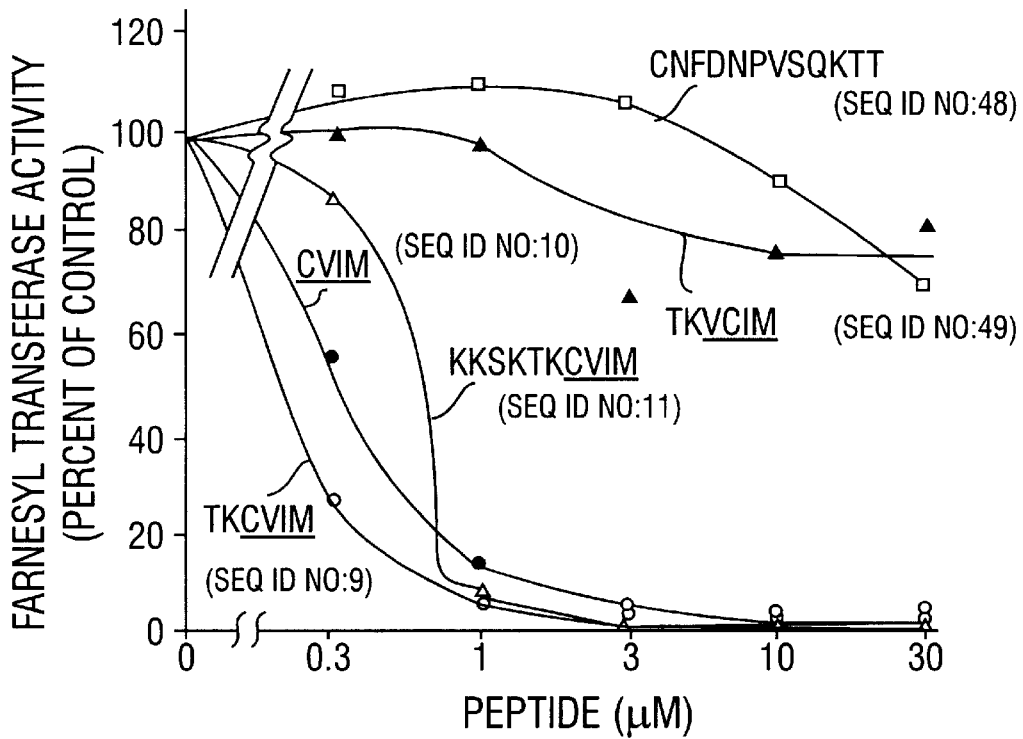
FIG. 8. Inhibition of Farnesyltransferase Activity by Peptides. Each standard reaction mixture contained 10 pmol [$^3$H]FPP, 1.8 μg of partially purified farnesyltransferase, 40 μM p21$^{H\text{-}ras}$, and the indicated concentration of competitor peptide added in 3 μl of 10 mM DTT. After incubation for 1 h at 37° C., TCA-precipitable radioactivity was measured as described in Experimental Procedures. Each value is the mean of triplicate incubations (no peptide) or a single incubation (+ peptide). A blank value of 0.11 pmol/h was determined in a parallel incubation containing 20 mM EDTA. This blank was subtracted from each value before calculating "% of control" values. The "100% of control" value after subtraction of the blank was 3.78 pmol of [$^3$H]FPP p21$^{H\text{-}ras}$ formed per h. Peptides Δ, ○ and ● correspond to the COOH-terminal 10, 6, and 4 amino acids of wild-type human p21$^{H\text{-}ras}$ protein (SEQ ID NOs:10, 9 and 11), respectively. Peptides ≡ (CNFDNPVSQKTT; SEQ ID NO:48) and ▲ (TKVCIN; SEQ ID NO:49) are control peptides.

To confirm that the 50-kDa band was the farnesyltransferase enzyme, the affinity column purified material was subjected to gel filtration. FIG. 7A and FIG. 7B shows that the farnesyltransferase activity and the 50-kDa band co-eluted from this column at a position corresponding to an apparent molecular weight of 70–100 kDa as determined from the behavior of markers of known molecular weight.

TABLE II

PURIFICATION OF FARNESYL: PROTEIN TRANSFERASE FROM RAT BRAIN

| Fraction | Protein mg | Specific Activity units/mg | Total Activity units | Purification -fold | Recovery % |
|---|---|---|---|---|---|
| 30–50% Ammonium Sulfate | 712 | 9.7[a] | 6906 | 1 | 100 |
| Mono Q | 30 | 275 | 8250 | 28 | 119 |
| Affinity Column | ~0.006[b] | 600,000 | 3600 | 61,855 | 52 |

The purification procedure was started with 50 rat brains.
[a]One unit of enzyme activity is the amount of enzyme that transfers 1 pmol of [$^3$H]farnesol from [$^3$H]FPP into acid-precipitable p21$^{H\text{-}ras}$ per h under the standard conditions.
[b]Protein concentration was estimated by coomassie blue staining of a SDS polyacrylamide gel using various amounts (0.5 to 2 μg) of bovine serum albumin as a refernce standard.

The adherence of the farnesyltransferase to the peptide affinity column suggested that the enzyme was capable of recognizing short peptide sequences. To test for the specificity of this peptide recognition, the ability of various peptides to compete with p21$^{H\text{-}ras}$ for the farnesyltransferase activity was measured. The peptide that was used for affinity chromatography corresponded to the carboxyl terminal six amino acids of P$_{21}$$^{K\text{-}rasB}$ (TKCVIM; SEQ ID NO:9). As expected, this peptide competitively inhibited farnesylation of P$_{21}$$^{H\text{-}ras}$ (open circles in FIG. 8). The terminal 4-amino acids in this sequence (CVIM; SEQ ID NO:10) (closed circles) were sufficient for competition. These two short peptides were no less effective than a peptide that contained the final 10-amino acids of the sequence (KKSKTKCVIM; SEQ ID NO:11) (open triangles). The simple transposition of the cysteine from the fourth to the third position from the COOH-terminus of the hexapeptide (TKVCIM; SEQ ID NO:9) (closed triangles) severely reduced inhibitory activity. An irrelevant peptide (closed squares) also did not inhibit.

Figure 9:
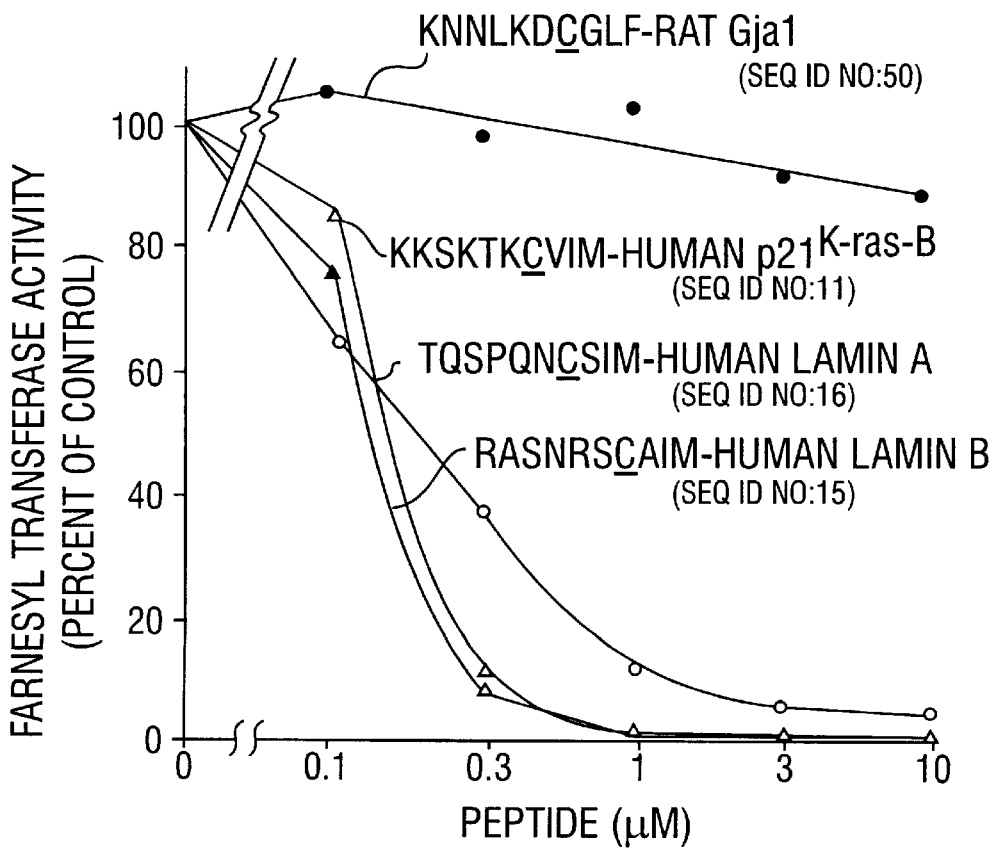
FIG. 9. Inhibition of Farnesyltransferase Activity by Peptides. Incubations were carried out exactly as described in the legend to FIG. 8. The "100% of control value" was 2.92 pmol of [$^3$H]farnesyl p21$^{H\text{-}ras}$ formed per hour. The blank value was 0.20 pmol/h. Each peptide consisted of the COOH-terminal 10 residues of the indicated protein. Peptide KNNLKDCGLF is SEQ ID NO:50; KKSKTKCVIM is SEQ ID NO:11; TQSPQNCSIM is SEQ ID NO:16; and RASNRSCAIM is SEQ ID NO:15.

FIG. 9 compares the inhibitory activities of four peptides of 10-amino acids each, all of which contain a cysteine at the fourth position from the COOH-terminus. The peptides corresponding to the COOH-terminus of human p21$^{K\text{-}rasB}$ and human lamin A and lamin B all inhibited farnesylation. All of these peptides are known to be prenylated in vivo (Casey et al., 1989; Farnsworth et al. 1989). On the other hand, the peptide corresponding to the sequence of rat Giα1, a 40 kDa G protein that does not appear to be farnesylated in vivo, did not compete for the farnesyltransferase reaction.

In data not shown it was found that the 4-amino acid peptide corresponding to the COOH-terminus of p21$^{H\text{-}ras}$ (CVLS; SEQ ID NO:19), p21$^{N\text{-}ras}$ (CVVM; SEQ ID NO:18), and p21$^{H\text{-}rasA}$ (CIIM; SEQ ID NO:17) all competed for the farnesylation reaction.

EXAMPLE II

Further Characterization of Farnesyltransferase

In the present Example, a series of tetrapeptides were tested for their ability to bind to the rat brain p21$^{H\text{-}ras}$ farnesyltransferase as estimated by their ability to compete with p21$^{H\text{-}ras}$ in a farnesyl transfer assay. Peptides with the highest affinity had the structure Cys-A1-A2-X, where A1 and A2 are aliphatic amino acids and X is a C-terminal methionine, serine, or phenylalanine. Charged residues reduced affinity slightly at the A1 position and much more drastically at the A2 and X positions. Effective inhibitors included tetrapeptides corresponding to the COOH-termini of all animal cell proteins known to be farnesylated. In contrast, the tetrapeptide CAIL (SEQ ID NO:65), which corresponds to the COOH-terminus of the only known examples of geranylgeranylated proteins (neural G protein γ subunits) did not compete in the farnesyl transfer assay, suggesting that the two isoprenes are transferred by different enzymes. A biotinylated hexapeptide corresponding to the COOH-terminus of p21$^{K\text{-}rasB}$ was farnesylated, suggesting that at least some of the peptides serve as substrates for the transferase. The data are consistent with a model in which a hydrophobic pocket in the farnesyltransferase recognizes tetrapeptides through interactions with the cysteine and the last two amino acids.

1. Materials and Methods

A. Peptides

Peptides were prepared by established procedures of solid-phase synthesis (Stewart et al., 1984) Tetrapeptides were synthesized on the Milligen 9050 Synthesizer using Fmoc chemistry. After deprotection of the last residue, a portion of the resin was used to make the N-acetyl-modified version of CVIM. This was done off-line in a solution of acetic anhydride and dimethylformamide at pH 8 (adjusted with diisopropylethylamine). The acetylated and unacetylated peptides were cleaved with 50 ml of trifluoroacetic acid:phenol (95:5) plus approximately 1 ml of ethanedithiol added as a scavenger. The N-octyl-modified version of CVIM was synthesized on an Applied Biosystems Model 430 Synthesizer using tBoc chemistry. The octyl group was added in an amino acid cycle using octanoic acid. The peptide was cleaved from the resin at 0° C. with a 10:1:1 ratio of HF (mls):resin (g):anisole (ml). The peptides were purified by high pressure liquid chromatography (HPLC) on a Beckman C18 reverse phase column (21.1 cm×15 cm), eluted with a water-acetonitrile gradient containing 0.1% (v/v) trifluouroacetic acid. Identity was confirmed for all peptides by fast atom bombardment (FAB) mass spectrometry. Just prior to use, each peptide was dissolved at a concentration of 0.8 mM in 10 mM dithiothreitol (DTT), and all dilutions were made in 10 mM DTT.

Biotinylated KTSCVIM (SEQ ID NO:53) was synthesized on an Applied Biosystems 430A Synthesizer. The biotin group was added after removal of the N-terminal protecting group before cleavage of the peptide from the resin. Specifically, a 4-fold molar excess of biotin 4-nitrophenyl ester was added to the 0.5 g resin in 75 ml dimethylformanide at pH 8 and reacted for 5 hours at room temperature. Cleavage, identification, and purification were carried out as described above.

To synthesize S-acetoamido CVIM (SEQ ID NO:10), purified CVIM was dissolved at a final concentration of 1 mM in 0.1 ml of 0.5 M Tris-chloride (pH 8.0) containing 15 mM DTT. The tube was flushed with nitrogen for 2 min, sealed, and incubated for 2.5 hours at 37° C. to reduce the cysteine residue, after which iodoacetamide was added to achieve a final concentration of 35 mM. After incubation for 15 min at 37° C., the reaction was stopped by addition of 10 mMDTT. Complete alkylation of CVIM was confirmed by FAB spectrometry and HPLC. The molecular weight of the product corresponded to the expected molecular mass of S-acetoamido CVIM.

B. Assay for Farnesyltransferase

The standard assay involved measuring the amount of [$^3$H]farnesyl transferred from all-trans [$^3$H]FPP to recombinant human p21$^{H\text{-}ras}$ as described in Example I. Each reaction mixture contained the following concentrations of components in a final volume of 25 μl: 50 mM Tris-chloride (pH 7.5), 50 μM ZnCl$_2$, 30 mM KCl, 1 mM DTT, 30 or 40 μM p21$^{H\text{-}ras}$, 15 pmol [$^3$H]FPP (12–23,000 dpm/pmol), 4 to 7.5 μg of partially purified farnesyltransferase (Mono Q fraction, see Example I), and the indicated concentration of competitor peptide added in 3 μl of 10 mM DTT. After incubation for 30–60 min at 37° C., the amount of [$^3$H] farnesyl present in trichloroacetic acid-precipitable p21$^{H\text{-}ras}$ was measured by a filter assay as described in Example I. A blank value (<0.6% of input [$^3$H]FPP) was determined in parallel incubations containing no enzyme. This blank value was subtracted before calculating "% of control" values.

C. Transfer of [$^3$H]Farnesyl from [$^3$]FPP to Biotinylated KTSCVIM Peptide

This assay takes advantage of the fact that peptides containing the Cys-AAX (SEQ ID NO:12) motif of ras proteins can serve as substrates for prenylation by farnesyltransferase. A heptapeptide containing the terminal four amino acids of p21$^{K\text{-}rasB}$ was chosen as a model substrate since it has a 20 to 40-fold higher affinity for the enzyme than does the COOH-terminal peptide corresponding to p21$^{H\text{-}ras}$. A biotinylated peptide is used as substrate so that the reaction product, [$^3$H]farnesylated peptide, can be trapped on a solid support such as streptavidinagarose. The bound [$^3$H]farnesylated peptide can then be washed, separated from unincorporated [$^3$H]FPP, and subjected to scintillation counting.

The biotin-modified KTSCVIM (SEQ ID NO:53) is synthesized on an Applied Biosystems 430A Synthesizer using established procedures of solid phase peptide synthesis. The biotin group is added after deprotection of lysine and before cleavage of the peptide from the resin. The identity and purity of the biotinylated peptide is confirmed by quantitative amino acid analysis and fast atom bombardment (FAB) mass spectrometry.

An aliquot of biotinylated KTSCVIM (SEQ ID NO:53; 0.4 mg) is dissolved in 0.6 ml of 10 mM sodium acetate (pH 3) buffer containing 1 mM DTT and 50% ethanol to give a final concentration of 0.67 mg/ml or 601 μM. This solution can be stored at 4° C. for at least 1 month. Immediately prior to use, the peptide solution is diluted with 1 mM DTT to achieve a peptide concentration of 18 μM. The standard reaction mixture contains the following components in a final volume of 25 μl: 50 mM Tris-chloride (pH 7.5), 50 μM ZnCl$_2$, 20 mM KCl, 1 mM DTT, 0.2% (v/v) octyl-β-glucopryranoside, 10–15 pmol of [$^3$H]FPP (15–50,000 dpm/pmol), 3.6 μM biotinylated KTSCVIM (SEQ ID NO:53), and 2–4 units of enzyme. After incubation at 37° C. for 30–60 min in 0.5-ml siliconized microfuge tubes, the reaction is stopped by addition of 200 μl of 20 mM Tris-chloride (pH 7.5) buffer containing 2 mg/ml bovine serum albumin, 2% SDS, and 150 mM NaCl. A 25-μl aliquot of well mixed streptavidin-agarose (Bethesda Research Laboratories, Cat. No. 5942SA) is then added, and the mixture is gently shaken for 30 min at room temperature to allow maximal binding of the [$^3$H]farnesylated peptide to the beads.

The beads are then collected by spinning the mixture for 1 min in a microfuge (12,500 rpm). The supernatant is removed, and the beads are washed three times with 0.5 ml of 20 mM Tris-chloride (pH 7.5) buffer containing 2 mg/ml bovine serum albumin, 4% SDS, and 150 mM NaCl. The pellet is resuspended in 50 μl of the same buffer and transferred to a scintillation vial using a 200-μl pipettor in which the tip end has been cut off at an angle. The beads remaining in the tube are collected by rinsing the tube with 25 μl of the above buffer and adding it plus the pipettor to the vial. A blank value, which consists of the radioactivity adhering to the beads in parallel incubations containing no enzyme, should be less than 0.5% of the input [$^3$H]FPP.

2. Results

To screen peptides for their affinity for the farnesyltransferase, studies were conducted wherein the ability of the peptides to compete with p21$^{H\text{-}ras}$ for acceptance of [$^3$H]farnesyl from [$^3$H]FPP as catalyzed by a partially purified rat brain farnesyltransferase was tested. As a reference point for the peptides, the tetrapeptide CVIM (SEQ ID NO:10) corresponding to the COOH-terminal sequence of p21$^{K\text{-}rasB}$ was employed. A series of typical studies in which alanine (FIG. 10A), lysine (FIG. 10B), or leucine (FIG. 10C) was systematically substituted at each of the three positions following cysteine in CVIM (SEQ ID NO:10), are shown. In each study the results were compared with those obtained with CVIM. Alanine and lysine were tolerated only at the A1 position. Insertion of these amino acids at the A2 or X positions decreased the affinity for the enzyme by more than 30-fold as estimated by the concentration required for 50% inhibition. Leucine was tolerated at the A2 position, but it decreased the affinity when inserted at the X position.

Figure 11:
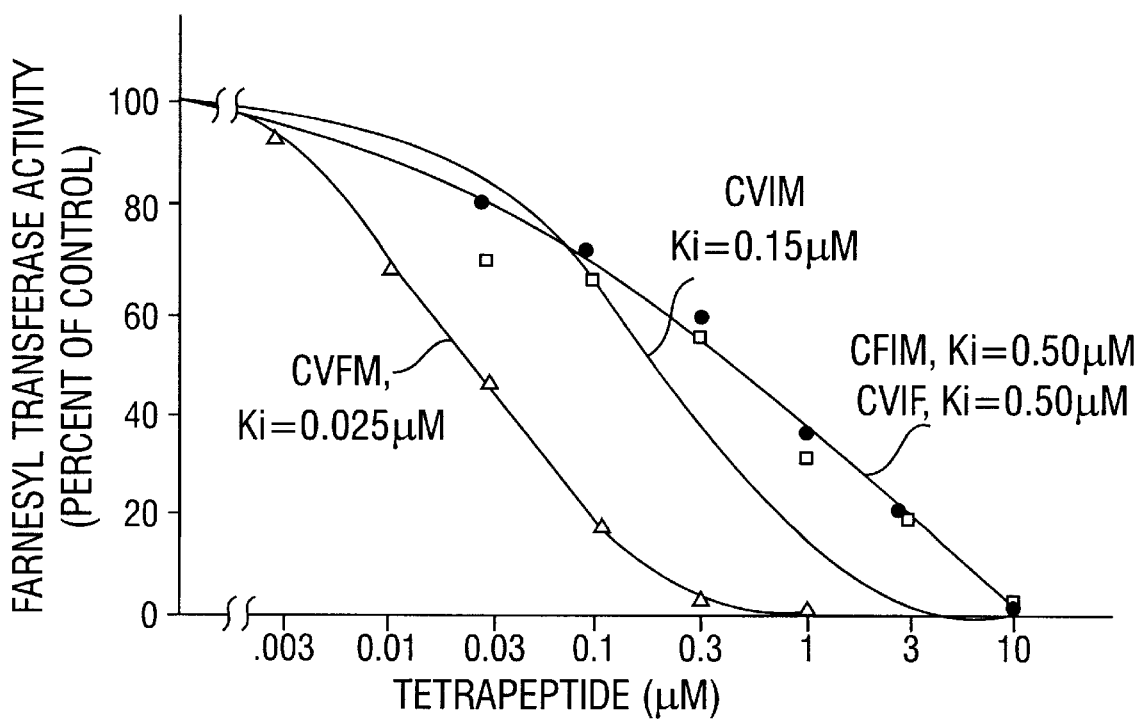
FIG. 11. Inhibition of Farnesyltransferase Activity By Phenylalanine-Containing Analogues of CVIM (SEQ ID NO:10). Enzyme activity was measured in the presence of the indicated concentration of competitor tetrapeptide as described in the legend to FIG. 10A. Represented are CFIM (SEQ ID NO:33); CVFM (SEQ ID NO:34); and CVIF (SEQ ID NO:35).

The substitution of phenylalanine for isoleucine at the A2 position increased the affinity for the enzyme by 6-fold, with half-maximal inhibition occurring at 25 nM (FIG. 11). No such effect was observed when phenylalanine was inserted at either of the other two positions.

In addition to performing assays with p21$^{H\text{-}ras}$ as a substrate, assays were also performed in which the substrate was a biotinylated heptapeptide, KTSCVIM, which contains the COOH-terminal four amino acids of p21$^{H\text{-}rasB}$ (Barbacid, 1987). The biotin was attached to the NH$_2$- terminus by coupling to the resin-attached peptide. The [³H]farnesylated product was isolated by allowing it to bind to beads coated with streptavidin as described in section c above.

Figure 12A:
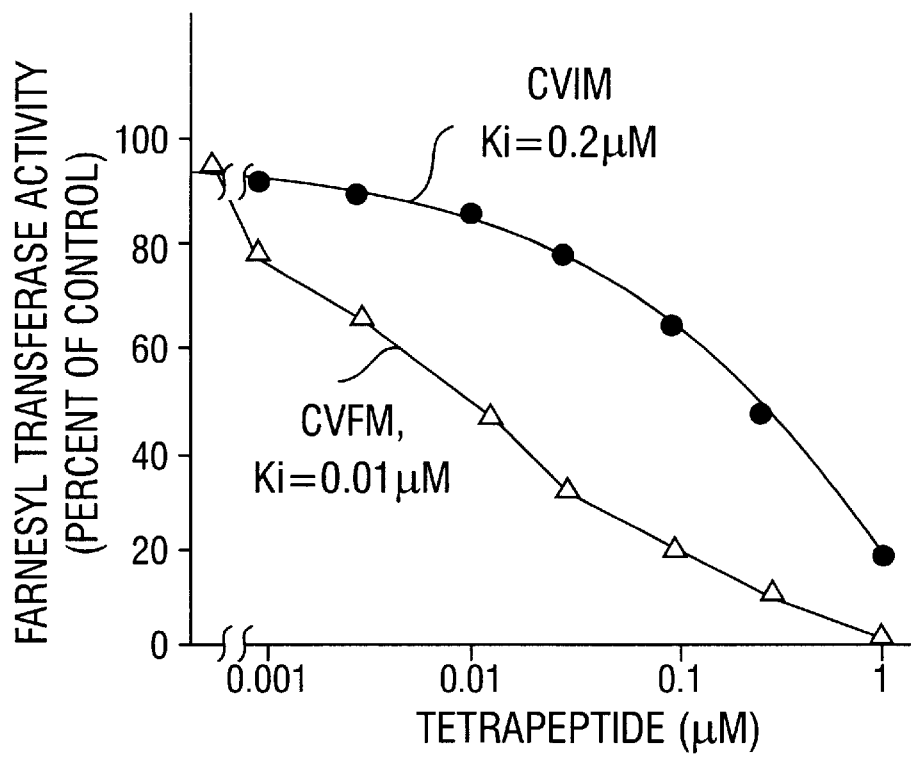
FIG. 12A. Inhibition of Farnesylation of p21$^{H\text{-}ras}$ By CVFM (SEQ ID NO:34). Each reaction mixture contained 15 pmol [$^3$H]FPP, 4.5 or 6 ng of purified farnesyltransferase, 40 μM p21$^{H\text{-}ras}$, and the indicated concentration of competitor tetrapeptide. After incubation for 30 min at 37° C., the amount of [$^3$H]farnesyl transferred to p21$^{H\text{-}ras}$ was measured by the standard filter assay. Values shown are the average of two studies. The "100% of control" values were 16 and 19 nmol min⁻¹ mg protein⁻¹. Represented are CVFM (SEQ ID NO:34) and CVIM (SEQ ID NO:10).
Figure 12B:
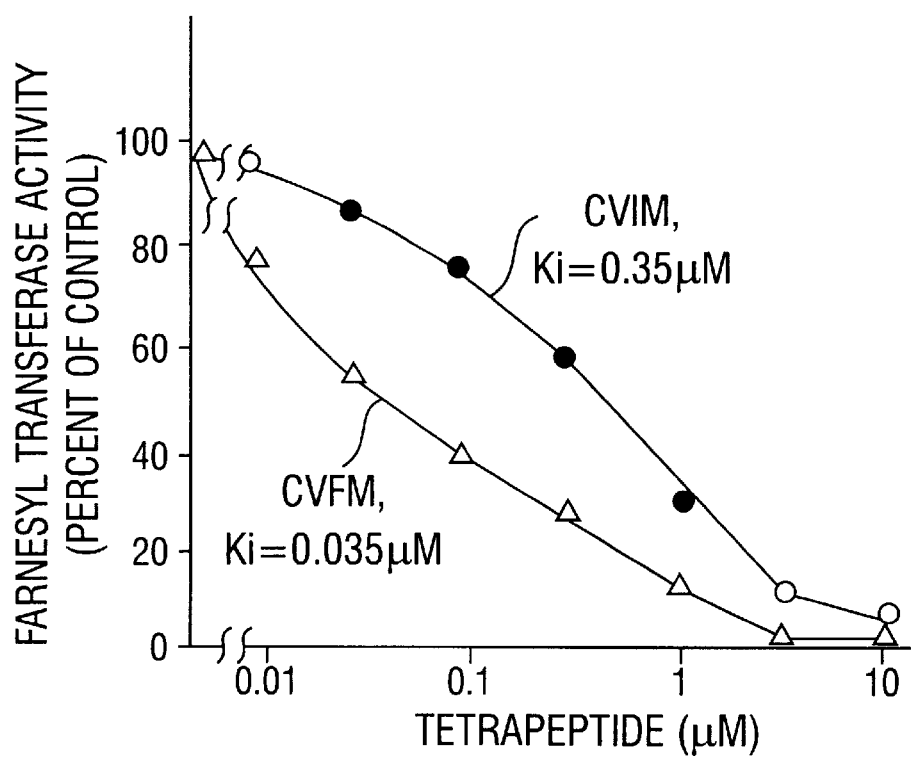
FIG. 12B. Inhibition of Farnesylation Biotinylated KTSCVIM (SEQ ID NO:53) By CVFM (SEQ ID NO:34). Each reaction contained 15 pmol [³H]FPP, 4.5 or 6 ng of purified farnesyltransferase, 3.4 μM biotinylated KTSCVIM (SEQ ID NO:53), and the indicated concentration of competitor tetrapeptide. After incubation for 30 min at 37° C., the [³H]farnesyl-labeled peptide was trapped on streptavidin-agarose, washed, separated from the unincorporated [³H]FPP, and subjected to scintillation counting. Values shown are the mean of 3 studies. The "100% of control" values were 10, 17, and 21 nmol min⁻¹mg protein⁻¹. Represented are CVFM (SEQ ID NO:34) and CVIM (SEQ ID NO:10).

FIG. 12A and FIG. 12B shows that the peptide CVFM (SEQ ID NO:34) was more potent than CVIM (SEQ ID NO:10) when either p21$^{H\text{-}ras}$ or the biotinylated heptapeptide was used as acceptor (FIG. 12A and FIG. 12B, respectively). In contrast to the other studies, which were conducted with a partially purified enzyme, the studies of FIG. 12A and FIG. 12B were carried out with a homogeneous preparation of affinity-purified farnesyltransferase.

Figure 13A:
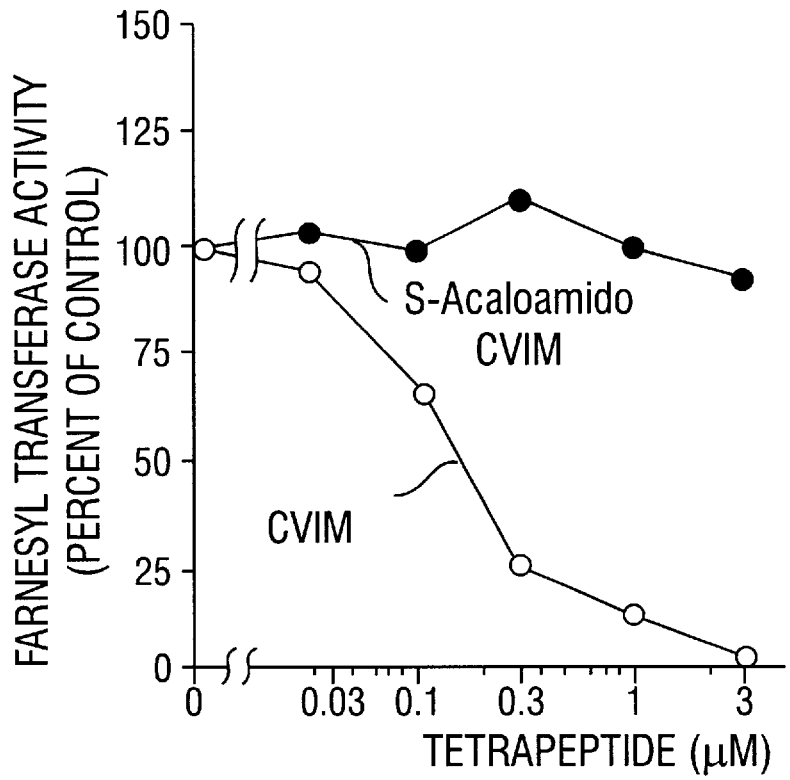
FIG. 13A. Inhibition of Farnesyltransferase By Modified Tetrapeptides. Enzyme activity was measured in the presence of varying concentrations of the indicated tetrapeptide as described in the legend to FIG. 10A. The "100% of control" value was 9.3 pmol min⁻¹ mg protein⁻¹.
Figure 13B:
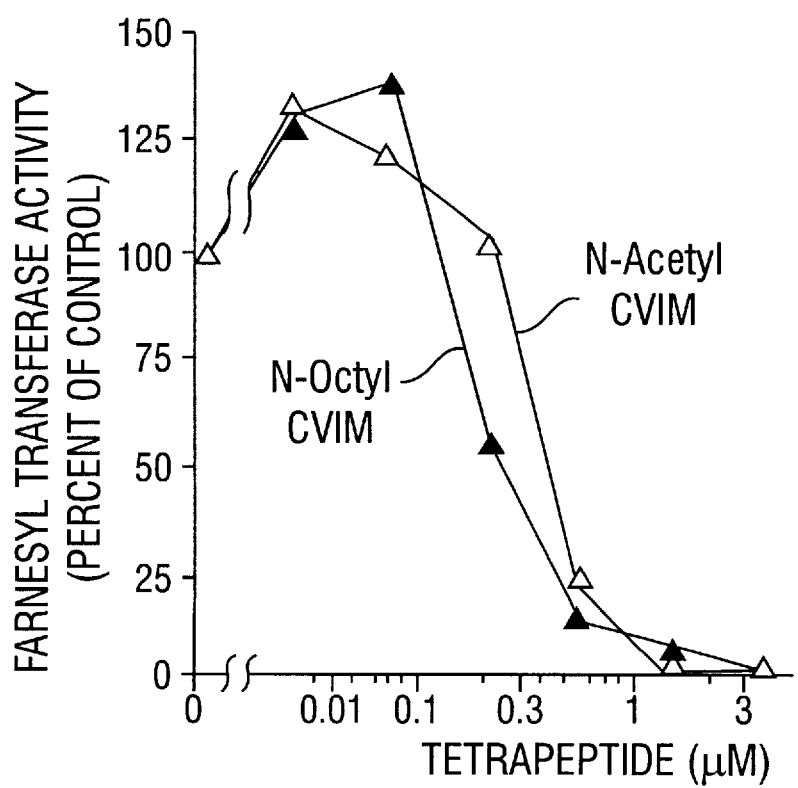
FIG. 13B. Inhibition of Farnesyltransferase By Modified Tetrapeptides. Enzyme activity was measured in the presence of varying concentrations of the indicated tetrapeptide as described in the legend to FIG. 10A. The "100% of control" value was 9.2 pmol min⁻¹ mg protein⁻¹.

The free sulfhydryl group for the cysteine is likely required for tetrapeptide inhibition, as indicted by the finding that derivitization with iodoacetamide abolished inhibitory activity (FIG. 13A). A blocked NH$_2$-terminus is not required, as indicated by similar inhibitory activity of N-acetyl CVIM and N-octyl CVIM (FIG. 13B) as compared to that of CVIM (FIG. 13A).

Figure 14:
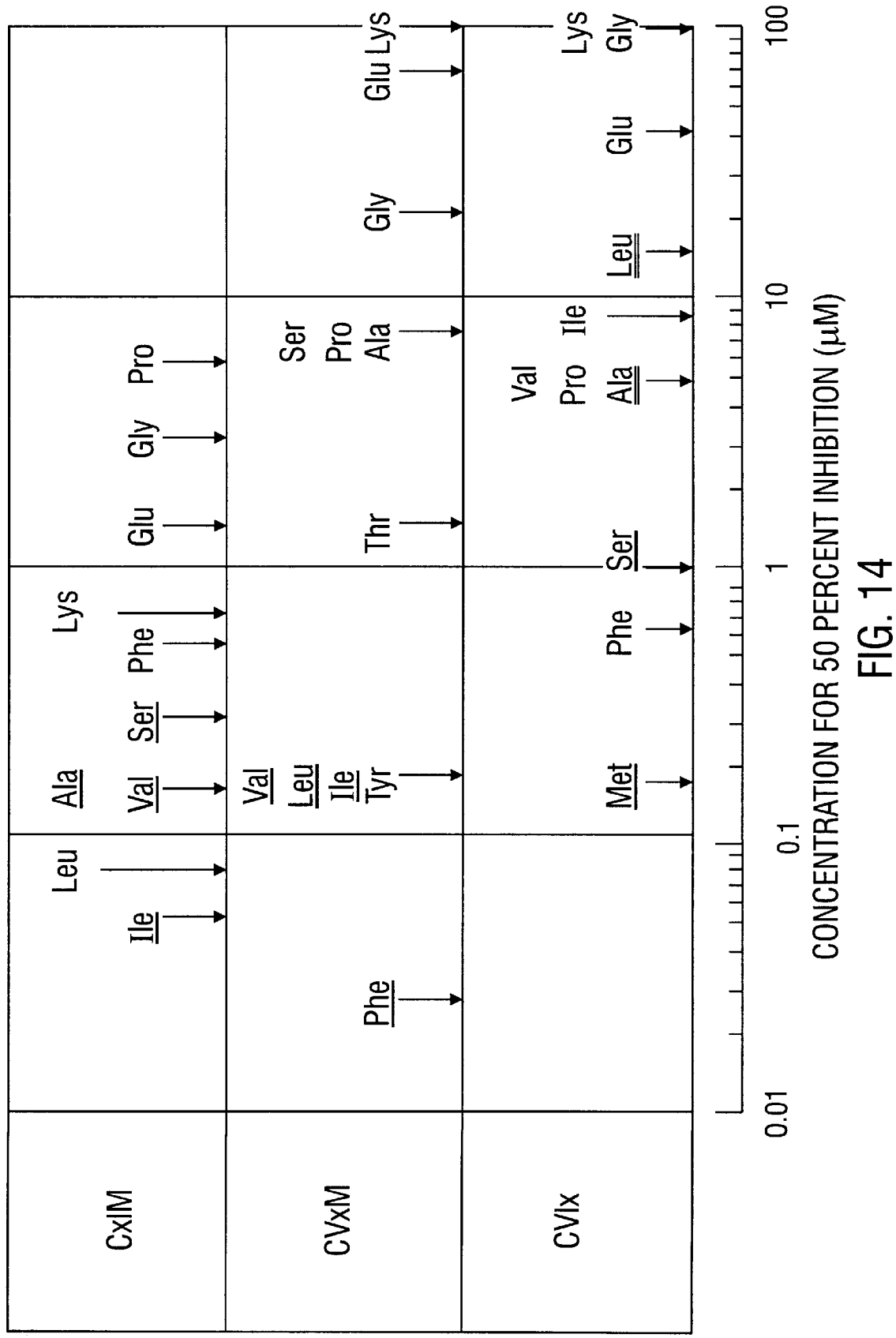
FIG. 14. Inhibition of Farnesyltransferase By Tetrapeptides With Single Amino Acid Substitutions in CVIM (SEQ ID NO:10). Enzyme activity was measured in the presence of the indicated competitor tetrapeptide as described in the legend to FIG. 10A and FIG. 11. Each tetrapeptide was tested at seven different concentrations ranging from 0.01 to 100 μM. The concentration of tetrapeptide giving 50% inhibition was calculated from the inhibition curve. The single and double underlines denote tetrapeptides corresponding to the COOH-terminal sequence of mammalian and fungal proteins, respectively, that are candidates for farnesylation (see Table III). CXIM is SEQ ID NO:54; CVXN is SEQ ID NO:55 and CVIX is SEQ ID NO:56.

FIG. 14 summarizes the results of all competition assays in which substitutions in the CVIM sequence were made. The results are presented in terms of the peptide concentration required for 50% inhibition. Table III summarizes the results of other studies in which tetrapeptides corresponding to the COOH-termini of 19 proteins were studied, many of which are known to be farnesylated. The implications of these studies are discussed below in Section 3.

Figure 15:
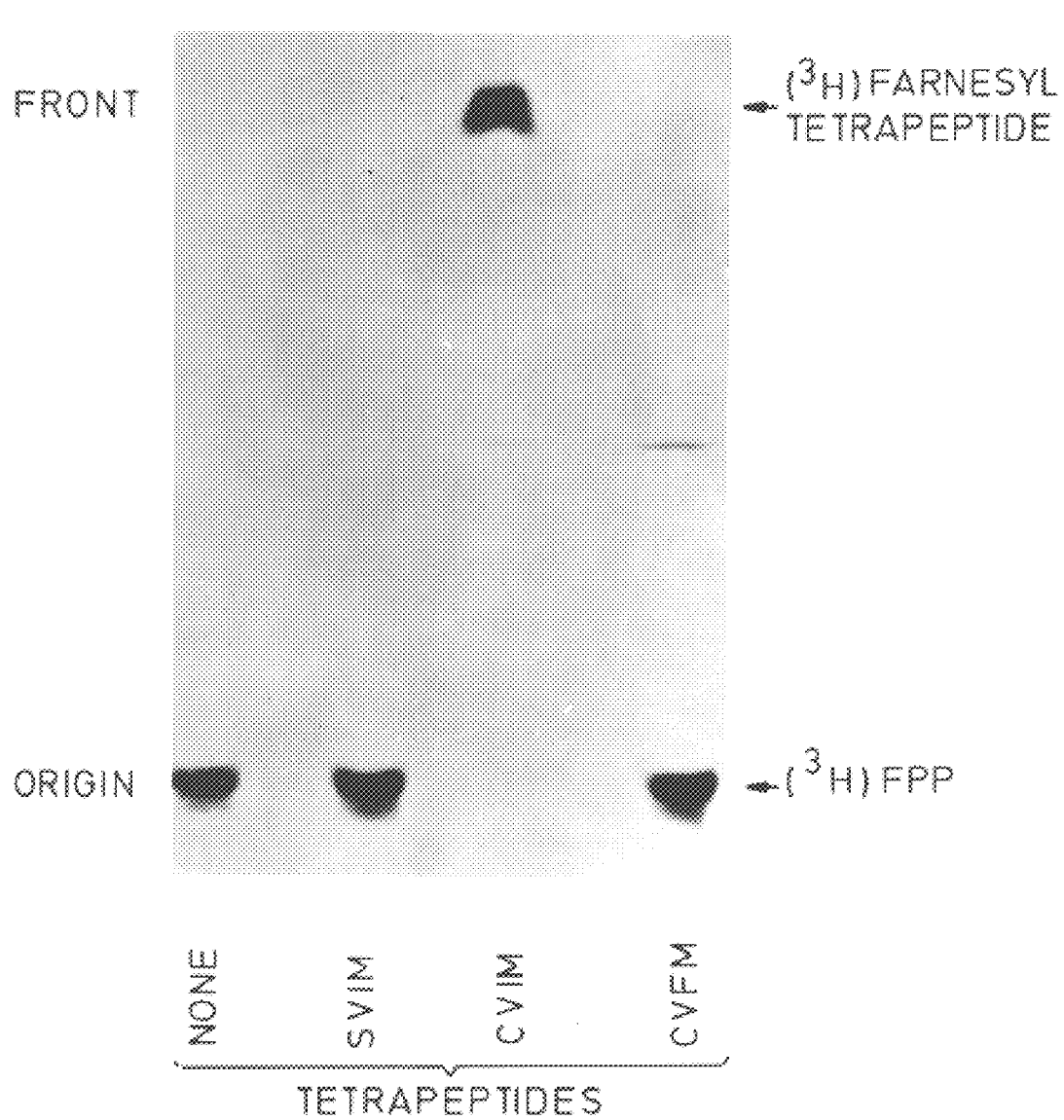
FIG. 15. Farnesylation of CVIM (SEQ ID NO:10) but not CVFM (SEQ ID NO:34) by Purified Farnesyltransferase. The standard assay mixture (25 μl) contained 17 pmol [³H]FPP (44,000 dpm/pmol), 5 ng of purified farnesyltransferase, 0.2% (w/v) octyl-β-D-glucoside, and 3.6 μM of the indicated tetrapeptide. After incubation for 15 min at 37° C., the entire reaction mixture was subjected to thin layer chromatography for 4 hours on Polygram SIL G sheet (Brinkmann Instruments) in a solvent system containing N-propanol/concentrated NH₄OH/water (6:3:1). The TLC sheet was then dried, sprayed with ENHANCE Spray (Dupont-New England Nuclear) and exposed to Kodak® X-OMAT AR Film XAR-5 for 25 hours at −70° C.

FIG. 15 shows that CVIM (SEQ ID NO:10 was farnesylated by purified farnesyltransferase while CVFM was not.

TABLE III

Inhibition of Rat Farnesyltransferase by
COOH-Terminal Tetrapeptides (SEQ ID NOs. in parentheses)
Corresponding to Known Proteins

| Protein | COOH-Terminal Species | Tetrapeptide | Concentration for 50% Inhibition μM |
|---|---|---|---|
| *p21$^{K\text{-}rasB}$ | Human, mouse | CVIM (10) | 0.15 |
| *p21$^{K\text{-}rasA}$ | Human | CIIM (17) | 0.15 |
| p21$^{N\text{-}ras}$ | Human | CVVM (18) | 0.15 |
| p21$^{N\text{-}ras}$ | Mouse | CVLM (20) | 0.15 |
| *Lamin B | Human, Xenopus laevis | CAIM (14) | 0.15 |
| Lamin A | Human, Xenopus laevis | CSIM (13) | 0.20 |
| Retinal cGMP phosphodiesterase, α subunit | Bovine | CCVQ (21) | 0.35 |
| *ras1 | S. cerevisciae | CIIC (22) | 0.35 |
| *ras2 | S. cerevisciae | CIIS (23) | 0.35 |
| *γ-Subunit of transducin | Bovine | CVIS (24) | 1.0 |
| p21$^{H\text{-}ras}$ | Chicken | CVIS (24) | 1.0 |
| p21$^{H\text{-}ras}$ | Human, rat | CVLS (19) | 3.0 |
| *a-Mating factor | S. cerevisciae | CVIA (25) | 5.0 |
| rap2b | Human | CVIL (26) | 11 |
| Dras | Dictostelium | CLIL (27) | 17 |
| rapla/krev1 | Human | CLLL (28) | 22 |
| *Mating factor | R. Toruloides | CTVA (29) | 30 |
| γ-Subunit of G protein | Bovine | CAIL (65) | 100 |
| HMG CoA reductase-1 | S. cerevisciae | CIKS (66) | >100 |

Figure 10A:
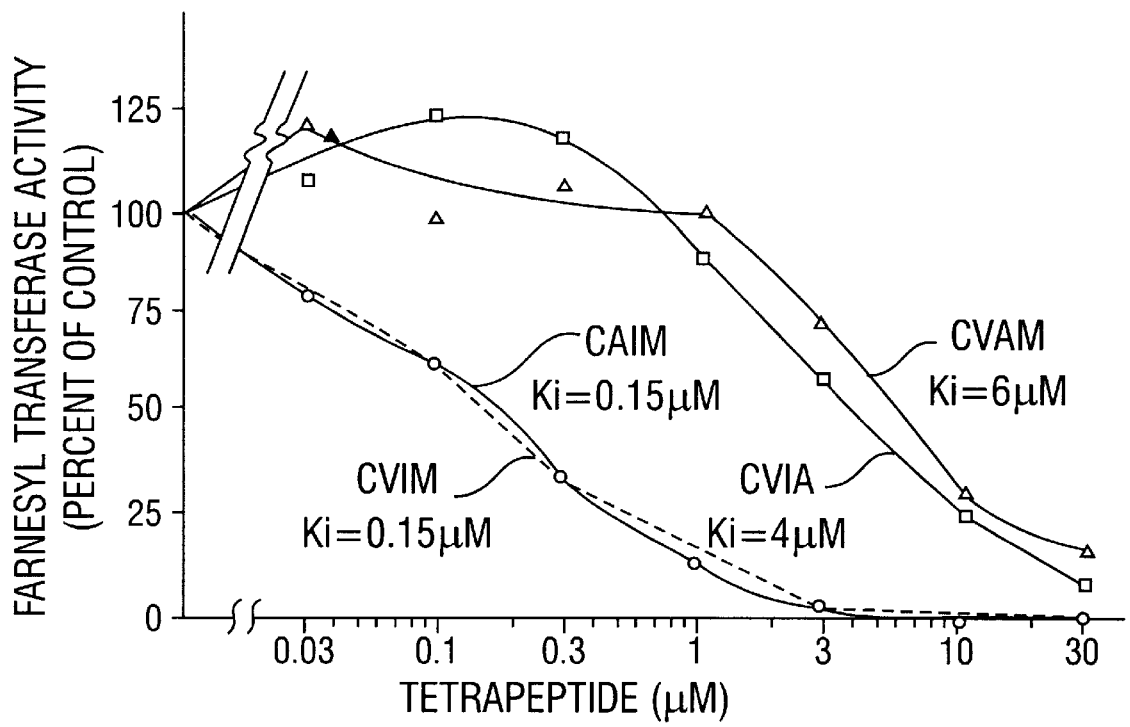
FIG. 10A. Inhibition of Farnesyltransferase By Tetrapeptide Analogues of CVIM (SEQ ID NO:10). The standard assay mixture contained 15 pmol [$^3$H]FPP, 4 to 7.5 μg partially purified farnesyltransferase, 30 or 40 μM p21$^{H\text{-}ras}$, and the indicated concentration of competitor tetrapeptide. After 30 or 60 min, the amount of [$^3$H]farnesyl attached to p21$^{H\text{-}ras}$ was measured by trichloracetic acid precipitation as described in the methods section of Example II. Each value is the average of duplicate or triplicate incubations (no peptide) or a single incubation (+peptide). Each tetrapeptide was tested in a separate study together with equivalent concentrations of CVIM (SEQ ID NO:10). The values for inhibition by CVIM ( . . . ) represent mean values from 21 studies in which the mean "100% of control" value was 13 pmol min$^{-}$mg protein$^{-1}$. $K_i$, concentration of tetrapeptide giving 50% inhibition. Represented are CAIM (SEQ ID NO:14), CVIA (SEQ ID NO:25) and CVAM (SEQ ID NO:30).
Figure 10B:
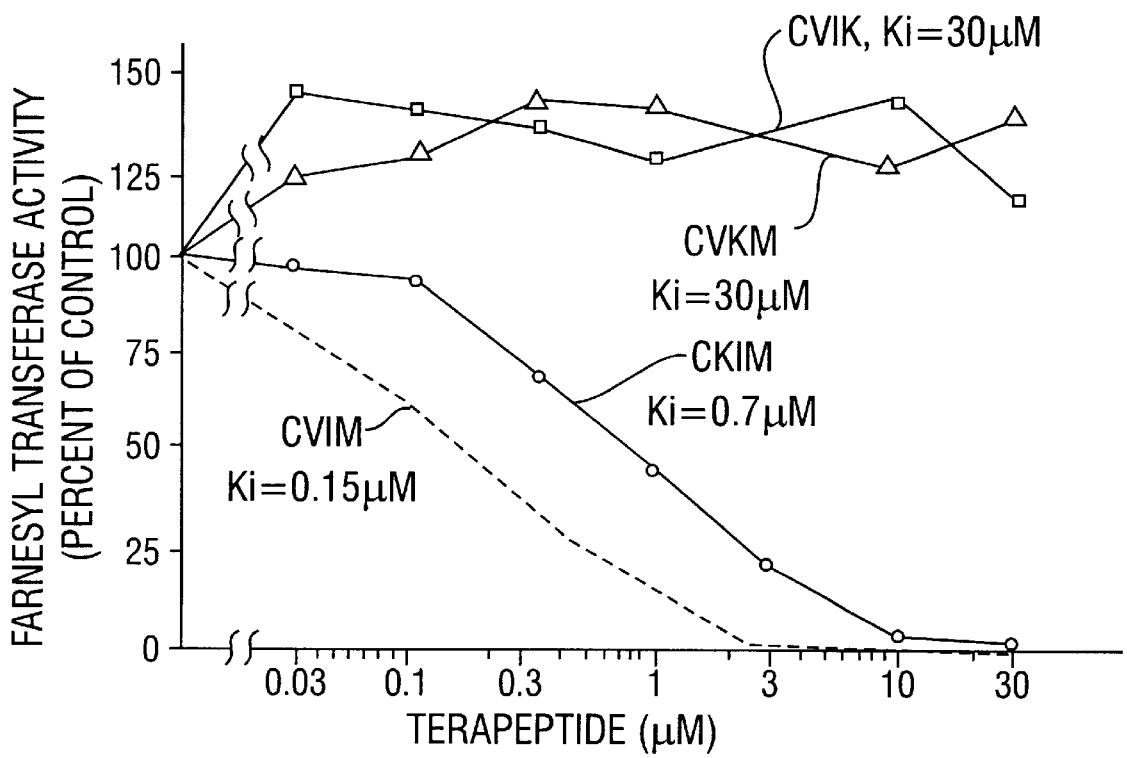
FIG. 10B. Inhibition of Farnesyltransferase By Tetrapeptide Analogues of CVIM (SEQ ID NO:10). Conditions were as described in FIG. 10A. Represented are CKIM (SEQ ID NO:31), CVKM (SEQ ID NO:51) and CVIK (SEQ ID NO:52).
Figure 10C:
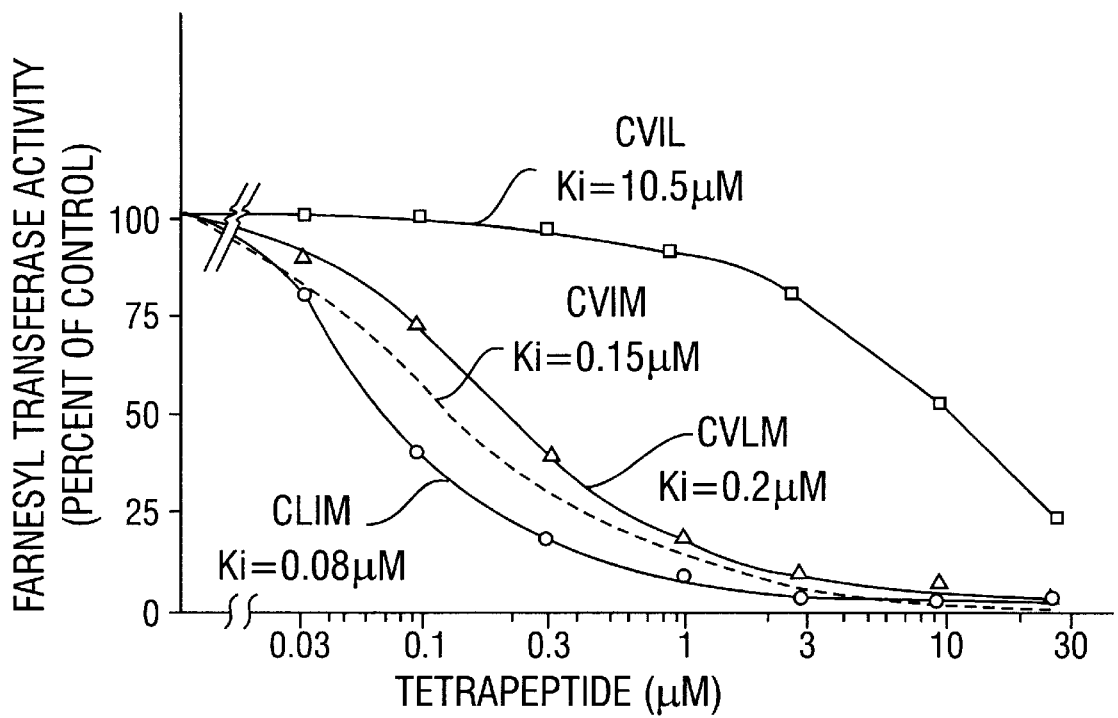
FIG. 10C. Inhibition of Farnesyltransferase By Tetrapeptide Analogues of CVIM (SEQ ID NO:10). Conditions were as described in FIG. 10A. Represented are CLIM (SEQ ID NO:32), CVLM (SEQ ID NO:20) and CVIL (SEQ ID NO:26).

Enzyme activity was measured in the presence of the indicated tetrapeptide as described in FIG. 10A. The tetrapeptides, represented by SEQ ID NOs: 10, 13, 14, 17–29, 65 (CAIL) & 66 (CIKS), respectively, were tested at seven different concentrations ranging from 0.03 to 100 μM. The concentration giving 50% inhibition was calculated from the inhibition curve.
*Shown to be farnesylated in vivo.

3. Discussion

The current data extend the observations on the p21$^{ras}$ farnesyltransferase set forth in Example I, and further indicate that the recognition site for this enzyme is restricted to four amino acids of the Cys-A1-A2-X type. As a reference sequence for these studies, the peptide CVIM was used. This peptide inhibited the farnesyltransferase by 50% at a concentration of 0.15 μM. Substitution of various amino acids into this framework yielded peptides that gave 50% inhibitions at a spectrum of concentrations ranging from 0.025 μM (CVFM; SEQ ID NO:34) to greater than 50 M (FIG. 14).

In general, the highest inhibitory activities were achieved when the A1 and A2 positions were occupied with nonpolar aliphatic or aromatic amino acids. This stringency was more severe at the A2 than at the A1 position. Thus, peptides containing lysine or glutamic acid at the A1 position gave 50% inhibition at 0.7 and 1.5 μM, respectively. When these two residues were inserted at the A2 position, the affinity for the enzyme declined by more than 50-fold. Glycine and proline lowered inhibitory activity moderately at the A1 position (50% inhibition at 4 and 8 μM) and somewhat more severely at the A2 position (8 and 20 μM).

The X position showed the highest stringency. In the context of CVIX (SEQ ID NO:56), methionine was the preferred residue but phenylalanine and serine were tolerated with only modest losses in activity (0.5 and 1 M, respectively). Aliphatic resides and proline were disruptive at this position, with 50% inhibitions in the range of 5–11 μM. Glutamic acid, lysine, and glycine were not tolerated at all; 50% inhibition required concentrations above 40 μM.

A study of tetrapeptides corresponding to the COOH-termini of known proteins (Table III) gave results that were generally in keeping with those obtained with the substituted CVIM (SEQ ID NO:10) peptides. They provided the additional information that glutamine and cysteine are well tolerated at the X position (CCVQ and CIIC; SEQ ID NOs:21 and 22). All of the proteins that are known to be farnesylated in intact cells (indicated by the asterisks in Table III) followed the rules outlined above, and all inhibited farnesylation at relatively low concentrations (5 μM or below) with the exception of the CTVA (SEQ ID NO:29) sequence, R. toruloides (Akada et al., 1989). This peptide inhibited the rat brain farnesyltransferase by 50% only at the high concentrations of 30 μM. It is likely that the farnesyltransferase in this fungal species has a different specificity than that of the rat brain.

The peptide CAIL (SEQ ID NO:65), which corresponds to the COOH-terminus of the γ-subunit of bovine brain G proteins (Gautam et al., 1989; Robishaw et al., 1989), did not compete efficiently with p21$^{H\text{-}ras}$ for farnesylation (Table III). A 50% inhibition at the highest concentration tested (100 μM) was observed. The inhibitory activity was lower than that of CVIL (SEQ ID NO:26; 12 μM) or CAIM (SEQ ID NO:14; 0.15 μM). Thus, the combination of alanine at the A1 position and leucine at the X position is more detrimental than either single substitution. This finding is particularly relevant since the gamma subunit of G proteins from human brain (Yamane et al., 1990) and rat PC12 cells (Mumby et al., 1990) have been shown to contain a geranylgeranyl rather than a farnesyl. These findings suggest the existence of a separate geranylgeranyltransferase-1 that favors CAIL (SEQ ID NO:65) and perhaps other related sequences.

The studies with the biotinyated heptapeptide (FIG. 12B) confirm that at least some of the short peptides act as substrates for the enzyme. The saturation curves relating reaction velocity to the concentration of either p21$^{H\text{-}ras}$ or the biotinylated heptapeptide are complex and sigmoidal. The inhibition curves with the various peptides differ from classic competitive inhibition curves. Finally, as mentioned in Example I, the maximal velocity of the purified enzyme is relatively low. These findings suggest that the binding of the peptides to the enzyme is not a simple equilibrium reaction. Rather, there may be a slow binding that requires conformational change.

The observation that the A1 position shows a relaxed amino acid specificity suggests that the residue at this position may not contact the farnesyltransferase directly. Rather, the contacts may involve only the cysteine and the residues at the A2 and X positions. A working model for the active site of the farnesyltransferase places the peptide substrate in an extended conformation with a largely hydrophobic pocket of the enzyme interacting with the X group of the CAAX-containing substrate.

EXAMPLE III

Recombinant Cloning of the Rat Farnesyl: Protein Transferase α and β Subunit cDNAs This example demonstrates the recombinant cloning of cDNAs corresponding to both the α and β subunit of rat farnesyltransferase. The method employed by the inventors involved the application of the peptide sequence information, as detailed above, to prepare specific primers for PCR-based sequencing, which sequences were then used for the construction of probes with which to screen cDNA libraries. The cloning of each of these cDNAs by the inventors' laboratory has recently been reported (Chen et al., 1991).

1. Methods

A. General Methods

General molecular biological techniques were employed in connection with the cloning reactions described below, as set forth in Sambrook et al., (1989). cDNA clones were subcloned into bacteriophage M13 or plasmid pUC vectors and sequenced by the dideoxy chain termination method (Sanger et al., 1977) using the M13 universal sequencing primer or gene specific internal primers. Sequencing reactions are preferably performed using a modified bacteriophage T7 DNA polymerase (Tabor et al., 1987) with $^{35}$S-labeled nucleotides, or Taq polymerase with fluorescently labeled nucleotides on an Applied Biosystems Model 370A DNA Sequencer.

For the isolation of total cellular RNA from rat tissues, the inventors preferred to employ the guanidinium thiocyanate/CsCl centrifugation procedure (Glisin et al., 1974). Whereas for the isolation of RNA from cell lines, the guanidinium HCl method was found to be preferable (Chirgwin et al., 1979). The isolation of poly A$^+$ RNA by oligo(dT)-cellulose chromatography was achieved by the methods described in Sambrook et al. (1989) and Aviv et al. (1972). Northern blot hybridization using single-stranded $^{32}$P-labeled probes was carried out as described by Lehrman et al. (1987). A cDNA probe for rat glyceraldehyde-3-phosphate dehydrogenase was obtained from Karl Normington, (University of Texas Southwestern Medical Center at Dallas).

Polyclonal antisera, specific for either the α or β subunit of farnesyltransferase, were prepared by immunizing rabbits with synthetic peptides derived from each specific subunit. Antibody Y533 was raised against a synthetic peptide with the sequence LQSKHSRESDIPASV (SEQ ID NO:67), derived from the predicted amino acid sequence of a cDNA clone of the α subunit. Antibody X287 was raised using the synthetic peptide IQATTHFLQKPVPGFEE (SEQ ID NO:68), derived from a tryptic digest of the β subunit. Each peptide was coupled to Keyhole Limpet hemocyanin using maleimidobenzoic acid N-hydrosuccinimide ester (Signa Chemical Co.) (Harlow & Lane 1988). For each antibody, three New Zealand White rabbits were immunized with 600 μg of coupled peptide in Freund's complete adjuvant. Immunoblot analysis was performed as described in (Seabra et al., 1991; Chen et al., 1991).

Rat PC12 pheochromocytoma cells, rat KNRK cells (CRL 1569), and human embryonic kidney 293 cells were obtained, respectively, from Thomas Südhof (University of Texas Southwestern Medical Center at Dallas), the American Type Culture Collection, and Arnold J. Berk (University of California, Los Angeles).

B. PCR and Probe Synthesis

Figure 16B:
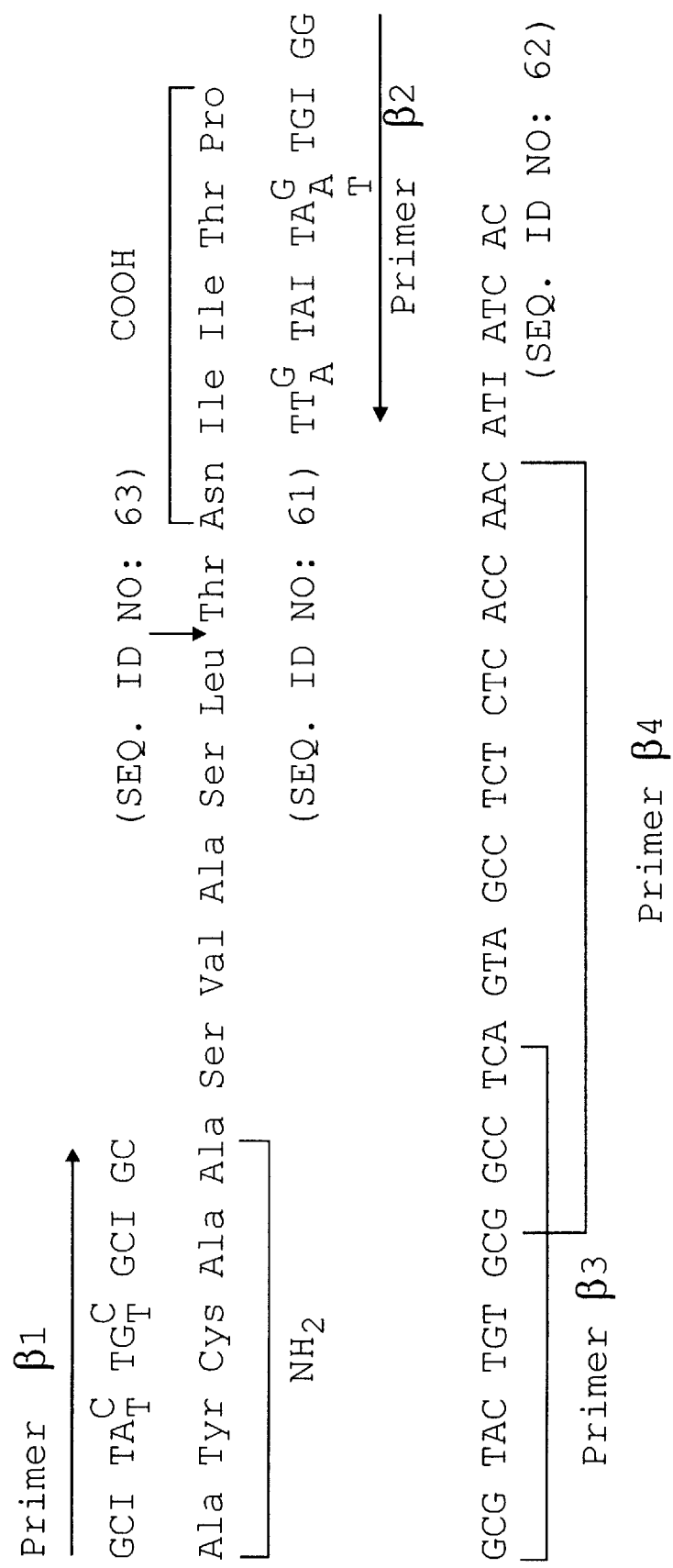
FIG. 16B. cDNA Probes Generated from a Knowledge of the Amino Acid sequences of Peptides Derived from Rat Farnesyltransferase α and β Subunits. Primer β1 (SEQ ID NO:60) and primer β2 (SEQ ID NO:61) were used in PCR with rat genomic DNA to generate the nucleotide sequence encoding the amino acid sequence of the peptide shown (SEQ ID NO:63), as described in Example III.

To derive a sequence for constructing an appropriate probe, rat genomic DNA may be used as a template for PCR as described by Saiki et al. (1988) and Lee et al. (1988). The approach used by the inventors was to sequence a portion of the α or β subunit genes through the use of appropriate PCR primers, based on a consideration of the peptide sequences (shown in Table I). Thus, PCR was used to obtain the rat genomic DNA sequences that encoded tryptic peptides derived from either the purified a or P subunits of rat farnesyltransferase (FIG. 16A, FIG. 16B and FIG. 16C). For the both the α and β sequences, the PCR primers were synthesized based on the NH$_2$- and COOH-terminal sequences of the peptides shown in FIG. 16A and FIG. 16B and included the degenerate inosine codons indicated. PCR primers were end-labeled with [γ-$^{32}$P]ATP. Each of the amplified DNA fragments were eluted from 12% acrylamide gels and sequenced by the method of Maxam and Gilbert (Maxam et al., 1980). Translation of the nucleotide sequences between the two primers yielded peptides with amino acid sequences identical to those of the peptides shown (FIG. 16A and FIG. 16B).

Using the DNA sequences of the PCR products, the inventors then synthesized an oligonucleotide probe that would hybridize with the region corresponding to the peptide, for use in the direct screening of the library. For the α subunit, a 38-mer probe with the nucleotide sequence: 5'-ATIGAGTTAAACGCAGCCAACTATACGGTCTGGCACTT-3', (a specific example in accordance with residues 6–54 of SEQ ID NO:64), was synthesized. Whereas for the β subunit, two primers, designated primer β3 and primer β4 were synthesized with the respective nucleotide sequences: 5'-GCGTACTGTGCGGCCTC-3' (residues 1–17 of SEQ ID NO:62) and 5'-GGCCTCAGTAGCCTCTCTCACCAAC-3' (residues 12–36 of SEQ ID NO:62).

The primers for the β subunit were used for 3'-end amplification of cDNA as described by Frohman et al. (1988). Poly(A)$^+$ RNA from rat KNRK cells was reverse transcribed using a (dT)$_{17}$-adaptor, 5'-GACTCGAGTCGACATCGA(T)$_{17}$-3' (SEQ ID NO:69). The 50 μl reaction mixture, containing 4 μg poly(A)$^+$ RNA, 2.5 μg (dT)$_{17}$-adaptor, and 100 units of Moloney murine leukemia virus reverse transcriptase (Bethesda Research Laboratories), was incubated at 37° C. for 1 hour. Reverse transcribed cDNA was diluted 50-fold with 10 mM Tris-HCl at pH 8.0, 1 mM EDTA, and subjected to specific PCR amplification as follows. 10 μl of diluted cDNA, 25 pmol of adaptor primer (5'-GACTCGAGTCGACATCG-3'; residues 1–17 of SEQ ID NO:69), and 25 pmol of primer 3 were boiled, after which PCR was carried out for 40 cycles (95° C., 40 sec; 58° C., 1 min; 72° C., 3 min) with TaqI polymerase. Amplified PCR products were subjected to electrophoresis on an agarose gel, transferred to a nylon membrane, and probed with $^{32}$P-labeled primer 4. The hybridizing DNA fragment was eluted, extracted with phenol/chloroform, and used as a template for a second PCR reaction. The reaction using 25 pmol each of adaptor primer and primer 4 was carried out with the same amplification protocol as described above. The reamplified DNA fragment was gel-purified, cleaved with RsaI or TaqI, and subcloned into an M13 vector for DNA sequencing and for subsequent generation of the single-stranded M13 probe that is referred to as Probe B. The DNA sequence of the PCR-derived clone was also used to generate a 50-mer oligonucleotide probe that is designated Probe A. Probes A and B were then used to screen cDNA libraries in order to obtain a full-length β subunit cDNA (see β subunit cloning section, below).

C. cDNA Libraries and Cloning

Rat PC12 cell poly(A$^+$) RNA and oligo (dT)-primed KNRK cell double-stranded cDNA libraries were constructed in bacteriophage λgt10, using a cDNA synthesis kit from Invitrogen. These cells were preferred because the inventors believed them to be rich in farnesyltransferase mRNA. Although numerous convenient methods are known for the construction of cDNA libraries, the inventors utilized the above kit from Invitrogen as they thought it to be a particularly convenient method. The cDNA itself was prepared using both oligo(dT)- and random hexamer-primed cDNA, then ligated to a suitable linker, with the EcoR1/Not1 linker being preferred in this case. cDNAs larger than 1 kb were isolated by size fractionation using a 1% agarose gel and ligated into EcoR1-cleaved λgt10 DNA (Stratagene), in order to complete the construction of the cDNA-containing vectors for library preparation. After in vitro packaging of the recombinant lambda phage with a DNA packaging extract (Stratagene), phage were plated out on host strain *E. coli* C600 hfl$^-$ cells.

α subunit cloning. Approximately 1×10$^6$ plaques of the rat brain library were screened. Duplicate filters were hybridized in 6×SSC (1×SSC=150 mM NaCl/15 mM Na citrate, at pH 7.0) with 1×10$^6$ cpm/ml of $^{32}$P-labeled probe (see above). One positive clone, λRB-17, with an insert of 1.4 kb was identified and plaque purified. Phage DNA from a plate lysate was subcloned into bacteriophage M13 and pBluescript vectors for DNA restriction mapping and sequencing (Sanger et al., 1980).

As the clone first obtained was not a full-length clone, 5'-end amplification was employed to produce the complete sequence, as described in Ref 34. Firstly, an M13 probe corresponding to the 5' end of λRB-17 was used to screen the KNRK cell library. Replicate filters were hybridized in 50% (v/v) formamide containing 1×10$^6$ cpm/ml of the probe. Positive clones were analyzed by PCR, and the clone with the longest insert (λKNRK-3) was purified and subcloned for analysis. A 5' Rapid Amplification of cDNA End procedure (5' RACE) (34) was used to extend the 5' end of λKNRK-3. An M13 probe derived from the amplification product (RACE-5') was then used to screen a rat testis library (purchased from Clontech), yielding λRTH, which extended to nucleotide position 53.

To obtain the extreme 5' end of the cDNA, a primer-extension λgt10 library was constructed from rat testis poly(A)$^+$RNA. First stand synthesis was primed with an oligonucleotide corresponding to a sequence near the 5'-end of RACE-5' using Maloney murine leukemia virus reverse transcriptase. After incubation at 37° C. for 1 h, the reaction was heated at 70° C. for 5 min. Five units of Thermostable rTth Transcriptase (Perkin-Elmer) was then added, and the reaction continued at 70° C. for 30 min. After second strand synthesis, the cDNAs were ligated to an EcoRI/NotI linker. Excess linkers were removed by Centricon 100 Microconcentrator (Amicon). Approximately 5×10$^5$ plaques were screened with a $^{32}$P-labeled probe corresponding to nucleotides 54–104, which was obtained from the sequence of λRTH. Twenty-five positive clones were identified. Phage DNA was prepared from plate lysates, and the insert from one of the longest clones, λPE-7, was subcloned for sequencing (Sanger et al., 1980).

β subunit cloning. Approximately 5×10$^5$ plaques were transferred to replicate filters. One filter was hybridized in 10% (v/v) formamide with 1×10$^6$ cpm/ml of a $^{32}$P-labeled 50-mer oligonucleotide probe (Probe A; described above). The other filter was hybridized in 50% formamide with 1×10$^6$ cpm/ml of a single-stranded M13 probe (Probe B; described above). One positive clone (λdT-7) with an insert of ~2.3 kb was identified with both probes and plaque purified. Phage DNA isolated from the plate lysate of λdT-7 was subcloned into M13 and pUC vectors for sequencing and restriction mapping.

To obtain the extreme 5' end of the cDNA, an M13 probe corresponding to the 5' end of λdT-7 was used to screen a rat brain "5'-stretch" cDNA library (purchased from Clontech). Replicate filters were hybridized in 50% formamide containing 1×10$^6$ cpm/ml of the probe. Of the 5×10$^5$ plaques screened, six positive clones were plaque purified and eluted in 0.2 ml buffer containing 100 mM NaCl, 8 mM MgSO$_4$, 50 mM Tris-HCl at pH 7.5, and 0.01% (w/v) gelatin. A primer corresponding to the right arm or left arm of λgt10 sequences flanking the unique EcoR1 cloning site was used in combination with a primer derived from the 5' end of the rat protein farnesyltransferase cDNA (λdT-7) for a PCR reaction. PCR products were analyzed on an agarose gel, and the clone containing the longest extension, λRB-23, was subcloned for further analysis.

D. Expression Vectors

Expression vectors for the α subunit of rat farnesyltransferase were constructed in pCMV5, a plasmid that contains the promoter-enhancer region of the major immediate early gene of human cytomegalovirus (Andersson et al., 1989). A PvuII fragment containing 20 base pairs of the 5' untranslated region and the entire coding region was excised from clone λRTH-B and ligated into SmaI-digested pCMV5 in both orientations. Plasmid λRTH-B is identical to λRTH except for the presence of an intron in the 5'-untranslated region at nucleotide position 39, upstream of the PvuII site at position 37–42. The resulting plasmids designated pFT-α (correct orientation) and pFT-αrev (reverse orientation), were characterized by restriction mapping.

Expression vectors for the β-subunit of rat farnesyltransferase were also constructed in pCMV5 (Andersson et al., 1989). An EcoR1 fragment containing the entire 5' untranslated region and the coding region of farnesyltransferase β subunit cDNA was excised from clone λRB-23 and ligated into EcoR1-digested pCMV5 in both orientations. The resulting plasmids, designated pFT-β1 (correct orientation) and pFT-β1rev (reverse orientation), were characterized by restriction mapping.

E. DNA Transfection

Human embryonic kidney 293 cells were grown in monolayer at 37° C. in medium A (Dulbecco's modified Eagle medium supplemented with 10% (v/v) fetal calf serum, 100 units/ml of penicillin, and 100 μg/ml streptomycin). On day 0, 6×10$^5$ cells/100-mm dish were seeded in medium A. On day 1, each dish of cells was transfected with 3 μg of the indicated plasmid plus 1 μg of pVA (a plasmid encoding adenovirus VA RNA$_I$; Akusjärvi et al., 1987) by the calcium phosphate method (Sambrook et al., 1989). On day 2, the cells received fresh medium A. On day 4, the cells from two dishes were harvested, pooled, and disrupted by repeated aspiration at 4° C. through a 25-gauge needle in 0.4 ml buffer containing 50 mM Tris-HCl at pH 7.5, 50 M ZnCl$_2$, 3 mM MgCl$_2$, 20 mM KCl, 1 mM dithiothreitol, and 0.4% (w/v) octyl-β-glucopyranoside. A cytosolic extract was obtained by centrifugation at 100,000×g for 1 h at 4° C., after which 0.16 to 5.4 μg of the supernatant fraction were assayed for farnesyltransferase activity by measuring the amount of [$^3$H]farnesyl transferred from ($^3$H)farnesyl pyrophosphate to p21$^{H-ras}$ protein as described above.

2. Results

A. α Subunit Cloning and Sequence Analysis

Degenerate oligonucleotide probes encoding the 5' and 3' ends of a tryptic peptide derived from the farnesyltransferase α subunit were used as primers in a PCR employing rat genomic DNA (FIG. 16A). The sequence of the amplified product was used as a probe to screen a random hexanucleotide-primed rat brain cDNA library cloned in λgt10. This procedure yielded λRB-17, which extended from a poly A tract up to nucleotide position 345 (this position refers to the final sequence of the mRNA, as in SEQ ID NO:2).

The 5'-end of the mRNA encoding the α subunit was found to contain a sequence extremely rich in GC basepairs (76% GC from nucleotides 71 to 205 and 90% GC from nucleotides 116 to 145). Multiple attempts to traverse this region by primer extension using reverse transcriptase gave products that terminated prematurely, or that encoded unspliced introns. Therefore, other strategies were employed in order to obtain the 5'-end of the mRNA (see above methods section for detailed protocols). A composite of the cDNA sequences thus obtained was used to generate the overall sequence of the mRNA (SEQ ID NO:2).

The mRNA was found to encode a protein of 377 amino acids (SEQ ID NO:1) with a calculated molecular weight of 44053. Although the cDNA sequence did not contain a terminator codon upstream of the first methionine codon, it is believed that this methionine represented the true initiator codon. This is supported by transfection studies, in which the recombinant protein produced was observed to have a molecular weight that was indistinguishable on immunoblots from that of the purified rat brain α subunit (see below and FIG. 20A). If the cDNA were incomplete, the initiator methionine must be upstream of the 5' end of the sequence obtained, and therefore the protein produced by the cDNA should be at least 2 kDa smaller than the authentic protein. Such a difference should have been detected in gel electrophoresis studies.

The most remarkable feature of the α subunit cDNA was determined to be a string of 9 consecutive proline residues near the NH$_2$-terminus (in SEQ ID NO:2), whose codons accounted for much of the extreme GC-richness of this region. The mRNA contained sequences corresponding to sequences of the peptides obtained following tryptic digestion of the purified α subunit. Discrepancies only occurred at positions that were assigned tentatively in sequencing trace amounts of protein (see Table I). Some slight homology has been noted between the rat α subunit amino acid sequence and yeast RAM2, the sequence of which is reported in He et al. (1991). The residues of the rat α subunit amino acid sequence (SEQ ID NO:1) which are identical to those of the yeast RAM2 sequence are boxed in FIG. 17.

Recently, Kohl et al. have reported the cloning of a partial cDNA clone corresponding to the bovine α subunit of farnesyltransferase (Kohl et al., 1991). The 329 amino acids encoded by this partial clone are 95% identical to the corresponding region in the α subunit of the rat farnesyltransferase. Comparison of the complete amino acid sequence of rat farnesyltransferase α subunit (377 amino acids) with that of the yeast RAM2 gene product (316 amino acids) disclosed by He et al. (1991) reveals that the two proteins are 39% identical in the COOH-terminal 211 residues, suggesting that RAM2 is the yeast counterpart of the α subunit of mammalian farnesyltransferase.

B. β Subunit Cloning and Analysis

A unique DNA sequence encoding a portion of the β subunit of the rat farnesyltransferase was obtained by the polymerase chain reaction (PCR) with rat genomic DNA and degenerate oligonucleotide primers (primers β1 and β2; SEQ ID NO:60 and 61, respectively) corresponding to potential sequences encoding a tryptic peptide obtained from the purified rat brain enzyme (FIG. 16B). Two unique oligonucleotides (primers β3 and β4, residues 1–17 and 12–36 of SEQ ID NO:62, respectively) were synthesized based on the sequence of the amplified product (FIG. 16C). These primers were then used in a 3'-end amplification strategy (Frohman et al., 1988) to obtain an amplified fragment from cDNA prepared from mRNA isolated from cultured rat kidney cells (KNRK cells). This fragment was used to generate probes that identified a bacteriophage containing a near full-length cDNA (λdT-7) from a cDNA library prepared from rat pheochromocytoma PC12 cells. Finally, a fragment from the 5'-end of λdT-7 was used to identify a clone containing a full-length farnesyltransferase β subunit cDNA (λRB-23) from a rat brain cDNA library (SEQ ID NO:4).

The cDNA for the rat brain farnesyltransferase β subunit contains 59 base pairs of 5'untranslated region followed by protein-coding region of 1314 base pairs and a 3'untranslated region of 1091 base pairs (SEQ ID NO:4). The cDNA encoded a protein of 437 amino acids (SEQ ID NO:3) and contained sequences corresponding to sequences of the peptides obtained following tryptic digestion of the purified rat brain farnesyltransferase β subunit. Although certain minor discrepancies in sequence between the protein and the cDNA were apparent, these occurred near the COOH-termini of the peptides and were attributed to ambiguities in sequencing the trace amounts of peptide that were available (see Table I).

The cDNA clones did not contain an inframe terminator codon upstream of the first methionine (amino acid residue 1 in SEQ ID NO:3). This is believed to be the initiator methionine as it lies in a good context for initiation according to Kozak's rules (Kozak, 1984) and because the cDNA encodes a protein of the same size as the β-subunit when transfected into animal cells (see below). Although λdT-7 was obtained from an oligo-dT primed cDNA library, the clone did not contain a poly A tract, nor did it contain a consensus polyadenylation sequence. However, RNA blot hybridization studies and expression studies (see below) suggested that the clone is essentially full-length.

The molecular weight of the β subunit of the rat brain farnesyltransferase was calculated to be 48,679. The amino acid composition did not show any particularly remarkable features and the calculated isoelectric point was 5.99. An analysis of the hydrophobicity plots did not reveal any extensive hydrophobic sequences.

A search of the GenBank and EMBL data banks revealed significant resemblance to two proteins, the DPR1-RAM1 protein of yeast *Saccharomyces cerevisiae* and a yeast open reading frame of unidentified function (ORF2). Extensive stretches of identity were evident between the β subunit protein sequence and the yeast DPR1-RAM1 gene product (FIG. 18). Sequence conservation was observed throughout the two proteins (overall identity: 37%), but was found to lessen at both ends, and the yeast protein was shorter by six amino acids. The residues of the rat β subunit amino acid sequence (SEQ ID NO:3) which are identical to those of the yeast DPR1-RAM1 sequence are boxed in FIG. 18.

In an article by Kohl et al. (1991), in a note added in proof, it is indicated that the β-subunit of bovine farnesyltransferase has been cloned and that it shares 96% homology to the rat β-subunit. However, no actual sequences corresponding to the β-subunit are disclosed by Kohl et al. (1991).

C. Northern Blotting Analyses

Figure 19A:
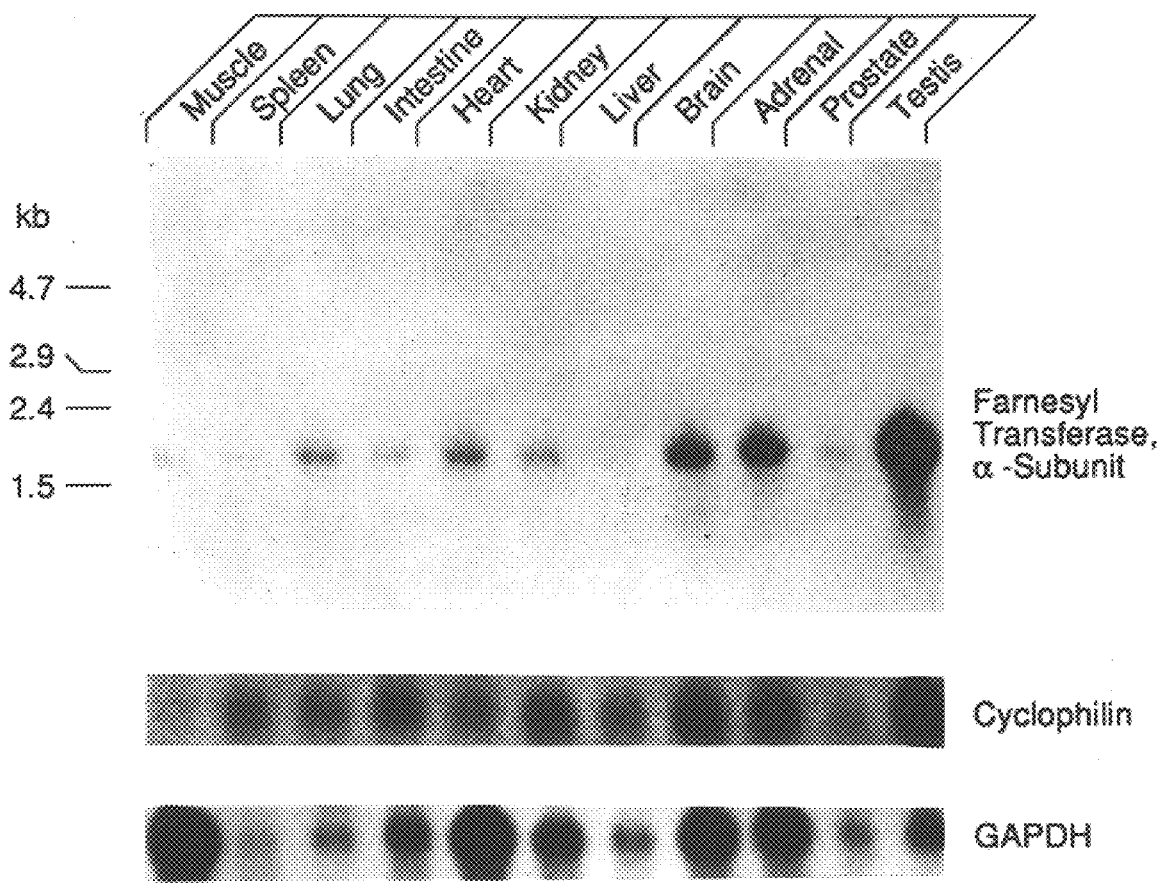
FIG. 19A. Distribution of Rat Farnesyltransferase α subunit mRNA in Tissues. Total RNA was isolated from the indicated rat tissues, and an aliquot (30 μg) was subjected to electrophoresis on a 1.5% agarose gel and blotted onto a nylon membrane for blot analysis. Hybridization was carried out at 42° C. for 20 hours with a mixture of two single-stranded uniformly ³²P-labeled cDNA probes, specific for either the α subunit (FIG. 19A) or β subunit (FIG. 19C) of rat farnesyltransferase. Each probe was ~500 nucleotides in length and was used at 2×10⁶ cpm/ml. The filters were washed in 0.2×SSC containing 0.2% (w/v) SDS at 68° C. for 1 hour, then exposed to Kodak® XAR-5 film for 2–4 days at −70° C. The positions of RNA standards run in adjacent lanes are indicated on the left. As a loading control, the same filter was reprobed initially with a ³²P-labeled 49-mer oligonucleotide corresponding to rat cyclophilin cDNA (2×10⁶ cpm/ml) and subsequently with a uniformly ³²P-labeled cDNA (~1.2 kb) for rat glyceraldehyde-3-phosphate dehydrogenase (GAPDH) (4×10⁶ cpm/ml). After each washing, the reprobed filter was exposed for 12 hours at −70° C.
Figure 19B:
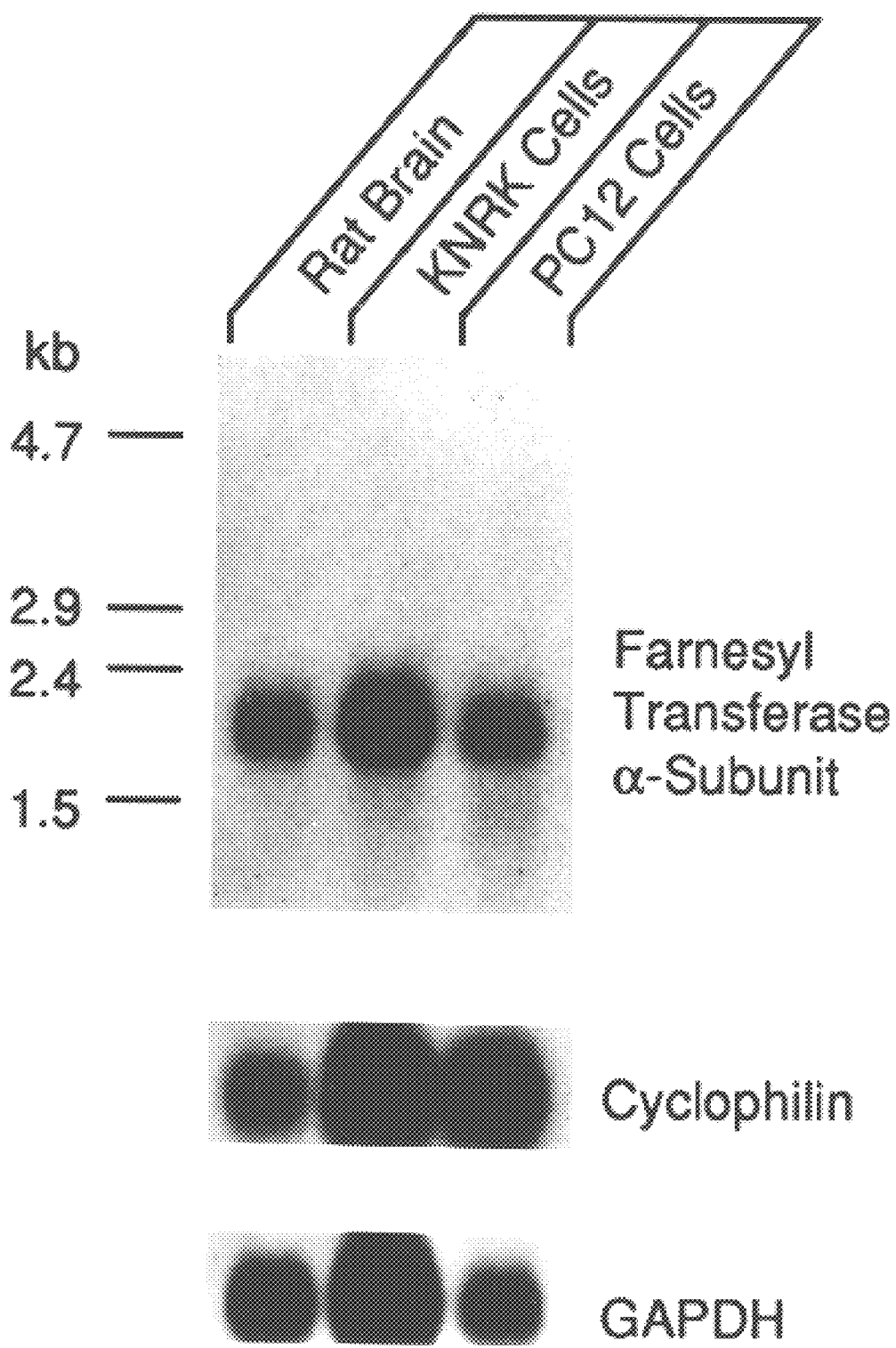
FIG. 19B. Distribution of Rat Farnesyltransferase α subunit mRNA in Cultured Cells. Expression of the α farnesyltransferase subunit mRNA in rat brain, KNRK cells, and PC12 pheochromocytoma cells. An aliquot of poly(A)⁺ RNA from each sample (10 μg) was subjected to blot analysis as described in FIG. 19A, and exposed for 12 h at −70° C. The same filter was subsequently reprobed with a ³²P-oligonucleotide derived from the rat cyclophilin cDNA sequence as described in FIG. 19A, and the filter was exposed to XAR-5 film for 12 h at −70° C.

Northern RNA blot analysis with $^{32}$P-labelled probes derived from the α subunit cDNA revealed a single mRNA of ~1.75 kb in multiple rat tissues, including lung, heart, kidney, brain, adrenal, and testis (FIG. 19A). The amount of mRNA in testis was several-fold higher than in any other tissue, an observation that was repeated on several occasions. An mRNA of the same size was also observed in two lines of cultured rat cells derived from kidney (KNRK cells) and adrenal medulla (PC12 cells) (FIG. 19B).

Figure 19C:
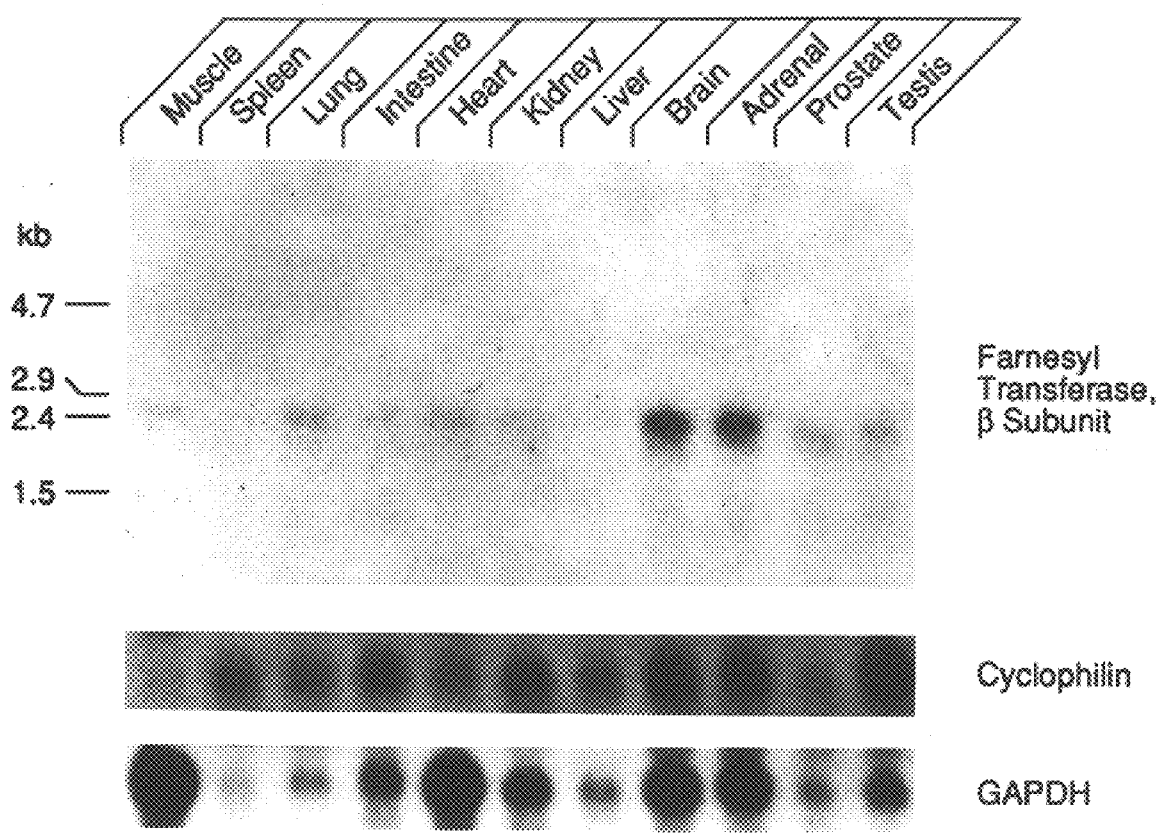
FIG. 19C. Distribution of Rat Farnesyltransferase β subunit mRNA in Tissues. Conditions and procedures were as described in FIG. 19A. Hybridization was carried out at 42° C. for 20 hours with a mixture of two single-stranded uniformly ³²P-labeled cDNA probes, specific for the β subunit of rat farnesyltransferase.

Northern RNA blot analysis with $^{32}$P-labelled probes derived from the β subunit cDNA revealed a hybridizing mRNA of ~2.5 kb in all rat tissues examined except liver and spleen (FIG. 19C). Adequate amounts of mRNA from these tissues were applied to the filter as confirmed by hybridization with control probes for cyclophilin and glyceraldehyde-3-phosphate dehydrogenase. The brain and adrenal gland appeared to have somewhat more mRNA for farnesyltransferase β-subunit than did the other tissues. More quantitative studies will be required to determine whether the variations shown in FIG. 19C are significant.

Figure 19D:
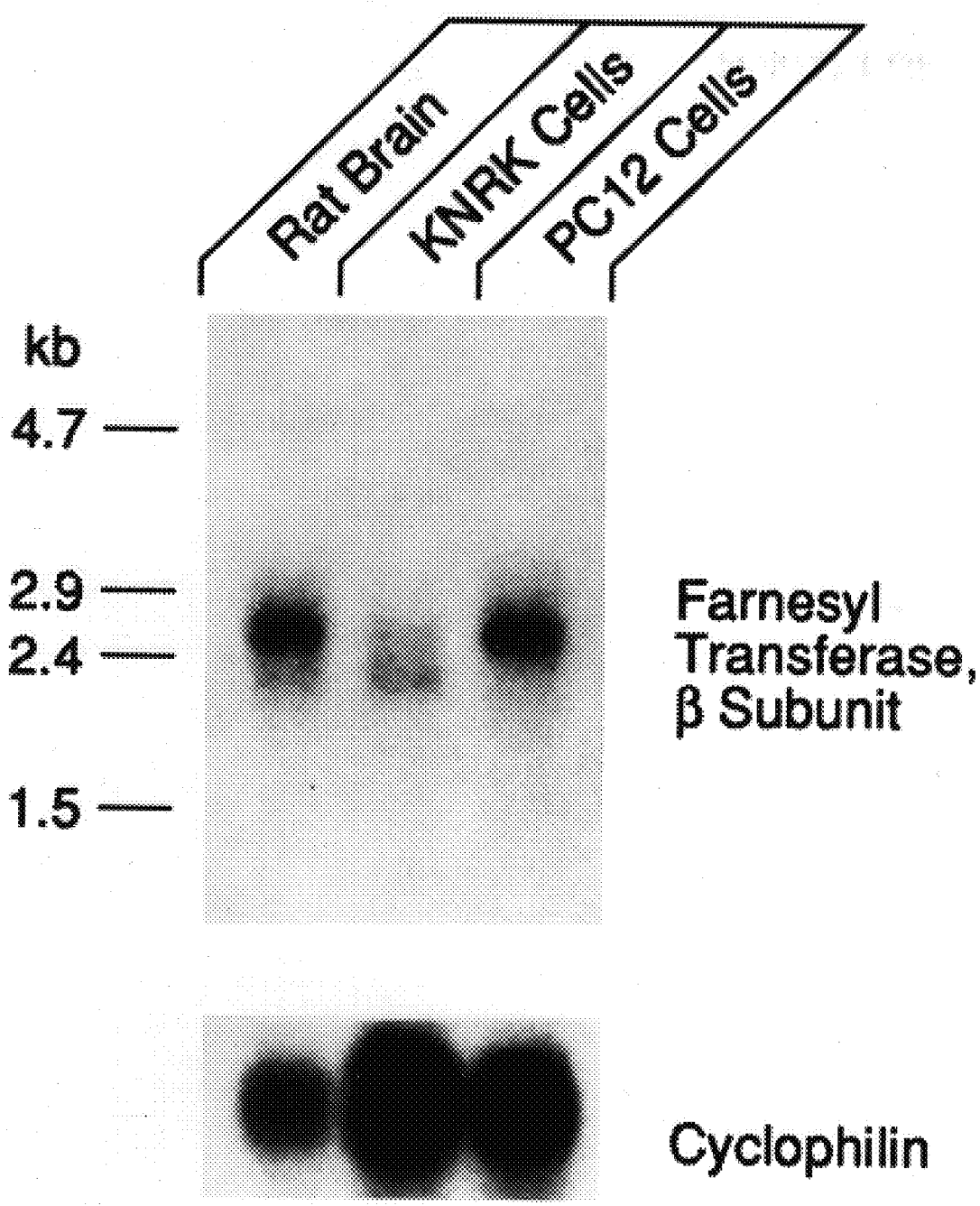
FIG. 19D. Distribution of Rat Farnesyltransferase β subunit mRNA in Cultured Cells. Expression of the β farnesyltransferase subunit mRNA in rat brain, KNRK cells, and PC12 pheochromocytoma cells. Procedures were as described in FIG. 19B.

The MRNA for the farnesyltransferase β-subunit was also found in the two cultured rat cell lines from which cDNA sequences had been obtained (FIG. 19D). PC12 cells had the 2.5-kb transcript, whereas the KNRK cells had two transcripts, one of which was smaller than the 2.5-kb mRNA (FIG. 19D). It was not determined whether the smaller transcript represented another gene product that crosshybridized with the β-subunit probe, or whether this MRNA represented alternative processing of an allelic transcript.

D. Co-Expression and Stability

The cDNA coding regions of both the α and β subunits were cloned into pCNV mammalian expression vectors in either the correct or the reverse orientation. The cDNAs were introduced into human kidney 293 cells by calcium phosphate-mediated transfection, and the proteins were detected by immunoblotting with specific antibodies against the α and β subunits. In both cases, the cDNA directed the expression of proteins with molecular weights that were indistinguishable on immunoblots from those of the purified rat brain farnesyltransferase α and β subunits (FIG. 20A and FIG. 20B).

Figure 20A:
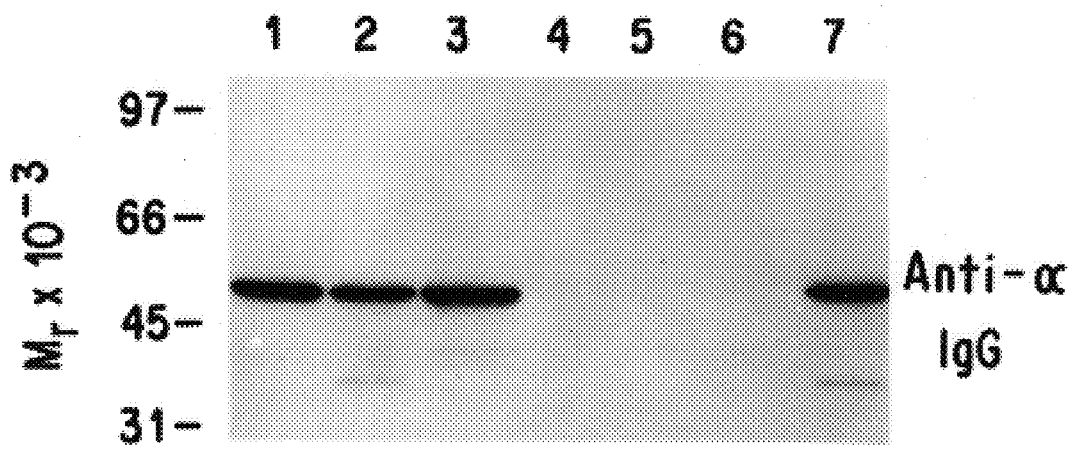
FIG. 20A. Immunoblot Analyses of α and β-subunits of Rat Protein Farnesyltransferase Expressed in Transfected 293 cells. Samples were subjected to SDS/PAGE on 10% gels and transferred to nitrocellulose. The filters were incubated with either 1 μg/ml of rabbit anti α subunit IgG-Y533 (A) or 5 μg/ml of rabbit anti β subunit IgG-X287 (B) followed by incubation with $^{125}$I-labeled goat anti-rabbit IgG (1×10$^6$ cpm/ml). Lanes 1 and 3, 20 μg of partially purified Mono Q fraction of rat brain farnesyltransferase. Lanes 2,4,5,6,7, 20 μg of cytosol from 293 cells transfected with the following plasmids: pFT-α plus pFT-β1 (lanes 2 and 7); pFT-α plus pFT-⊕1rev (lane 4); pFT-αrev plus pFT-β1 (lane 5); pFT-αrev plus pFT-⊕1rev (lane 6). The filters were exposed to Kodak® XAR-5 film for 48 h at −70° C. Molecular weight markers are indicated. Plasmids pFT-αrev and pFT-β1rev contain cDNAs inserted in the reverse (noncoding) orientation.
Figure 20B:
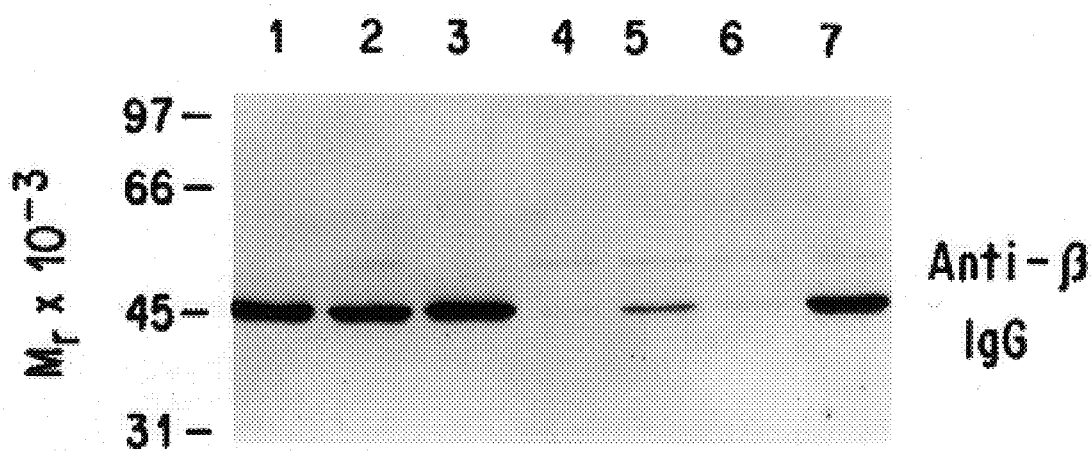
FIG. 20B. Immunoblot Analyses of α and β-subunits of Rat Protein Farnesyltransferase Expressed in Transfected 293 cells. Procedures were as described in FIG. 20A, except the filters were exposed to Kodak® XAR-5 film for 16 h at −70° C. Molecular weight markers are indicated. Plasmids pFT-αrev and pFT-β1rev contain cDNAs inserted in the reverse (noncoding) orientation.
Figure 21:
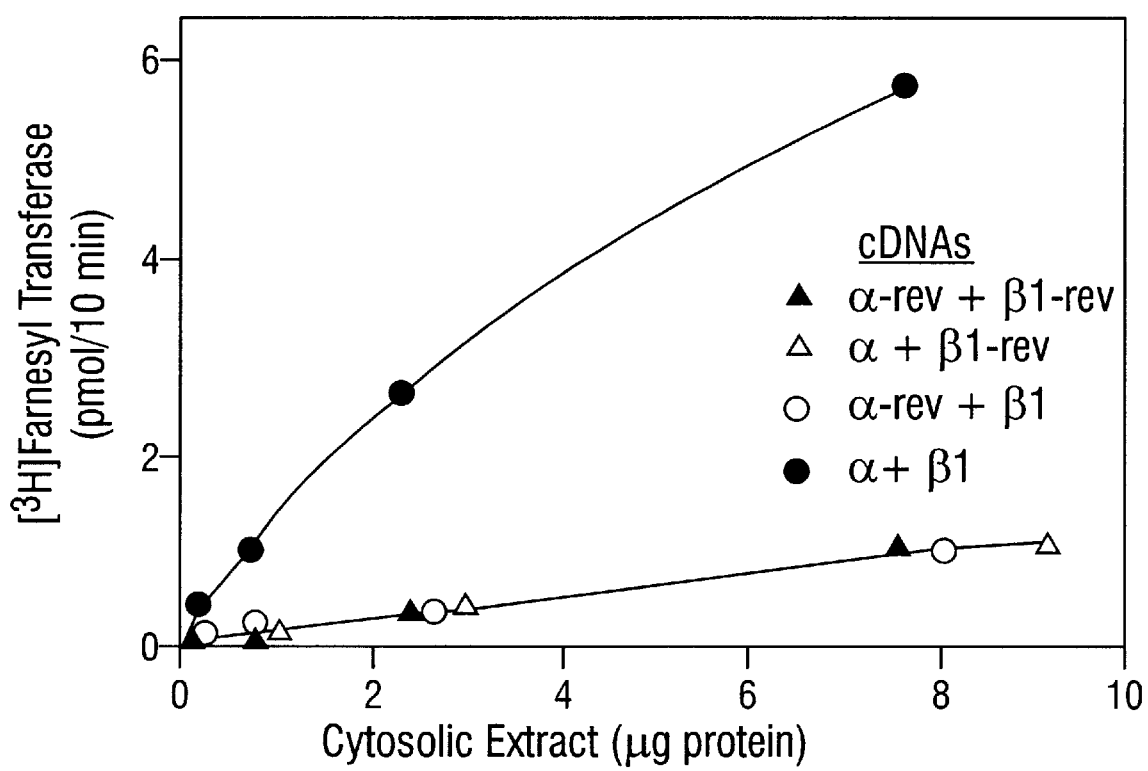
FIG. 21. Farnesyltransferase Activity of Cytosolic Extracts from 293 cells Transfected with cDNAs Encoding the α and β Subunits of Rat Protein Farnesyltransferase in the Correct or Reverse (rev) Orientations. Cells were transfected with 3 μg of the indicated plasmid plus 1 μg pVA. Each assay contained in a final volume of 25 μl the indicated amount of cytosolic extract, 50 mM Tris-chloride (pH 7.5), 50 μM ZnCl$_2$, 20 mM KCl, 3 mM MgCl$_2$, 1 mM dithiothreitol, 0.4% (v/v) octyl-β-glucopyranoside, 40 μM p21$^{H-ras}$, and 15 pmol of all-trans [$^3$H]farnesyl pyrophosphate (15,335 dpm/pmol). Assay tubes were incubated at 37° C. for 10 min, after which the amount of [$^3$H]farnesyl attached to p21$^{H-ras}$ was measured. Each value is the average of duplicate incubations.

The accumulation of detectable amounts of α subunit required simultaneous transfection with a properly oriented cDNA encoding the β-subunit (FIG. 20A). Similarly, the amount of detectable β-subunit was increased by transfection with the α subunit cDNA in the correct orientation (FIG. 20B). Transfection with the two cDNAs in the correct orientation was also required in order to produce significant amounts of p21$^{ras}$ farnesyltransferase activity as measured in cytosolic extracts (FIG. 21).

3. Discussion

The delineation of the amino acid sequence of the α subunit has not yet allowed its catalytic role to be precisely identified. Homology searches of protein databases failed to reveal significant resemblance of the α subunit to other proteins except for proteins that contain long stretches of prolines. These include such apparently unrelated proteins as the catalytic subunits of rat and human protein phosphatase 2B, mouse retinoblastoma-associated protein pp105, and *Dictyostelium discoideum* protein tyrosine kinase-1. The α subunit does not bear significant structural resemblance to known prenyltransferases such as mammalian farnesyl pyrophosphate synthetase or yeast hexaprenyl pyrophosphate synthetase.

Present evidence suggests that the α subunit may be shared with another prenyltransferase with a different β subunit that exhibits geranylgeranyltransferase-1 activity (Seabra et al., 1991). If the shared α subunit is stable only as a complex with one of several β subunits, this mechanism would assure that cells maintain only enough α subunits to satisfy all of the β subunits, thereby avoiding accumulation of excess α subunits, which might be toxic (Chen et al., 1991).

The above data reveal that the α and β subunits of the rat farnesyltransferase do not exhibit farnesyltransferase activity when expressed by themselves in transfected human 293 cells. However, co-expression of the two subunits results in the production of an active enzyme. Such expression data provides support for the previous conclusion that the farnesyltransferase is a heterodimer that requires both the α and β subunits for catalytic activity (Chen et al., 1991).

Furthermore, the transfection studies indicate that mammalian cells will not accumulate high levels of either subunit of the farnesyltransferase unless the other subunit is present. This is particularly true for the α subunit, whose accumulation was nearly completely dependent on co-expression of the β subunit. It is likely that the α subunit is rapidly degraded unless the β subunit is present. However, until pulse-chase labeling studies are performed, the possibility of control at the level of mRNA stability or translation cannot be ruled out.

The similarity between the rat β subunit and the previously reported sequence of the yeast DPR1-RAM1 gene product (Goodman et al., 1990) indicates that the latter is the yeast equivalent of the peptide-binding subunit of the mammalian farnesyltransferase. These findings confirm the previous suspicion that the yeast gene encodes one of the subunits of the farnesyltransferase and explains the failure of this protein to exhibit farnesyltransferase activity when expressed alone in *E. coli* (Goodman et al., 1988; Schafer et al., 1990).

Mutations at a second locus, designated RAM2, also disrupt farnesyltransferase activity in yeast (Goodman et al., 1990). The defect in the RAM2 cells is complemented by mating with the DPR1-RAM1 mutant. This finding suggests that the RAM2 gene product is the α subunit of the yeast farnesyltransferase. A more recent report of He et al. (1991) indicates that coexpression of the RAM1 and RAM2 genes in *E. coli* provided extracts that farnesylated synthetic a-factor substrate. However, when extracts from separate clones were mixed, only partial farnesyltransferase activity, on the order of about 3.5%, was recovered.

An inspection of the conserved sequences in the rat β subunit and the DPR1-RAM1 protein fails to reveal any obvious candidates for the peptide binding site. The rat protein (residues 35–41) does contain the sequence LXD- DXXE (SEQ ID NO:70), which resembles a sequence in four polyprenyl synthetases in which Ile, Leu or Val precedes the XDDXXD sequence (residues 2–7 of SEQ ID NO:70) that is believed to be a prenyl pyrophosphate binding site (Ashby and Edwards, 1990). This sequence is not found in the same position in the DPR1-RAM1 protein, and its significance in the β subunit is uncertain. Although the farnesyltransferase reaction requires two divalent cations ($Mg^{++}$ and $Zn^{++}$), the sequence of the β subunit does not reveal any obvious metal binding sites.

Recently, the inventors have explored the separate catalytic roles of $Zn^{2+}$ and $Mg^{2+}$ and the specificity of the prenyl pyrophosphate binding site of the rat brain protein farnesyltransferase, using a purified enzyme preparation. In summary, it was found that the binding of $p21^{H-ras}$ to the enzyme was abolished by dialysis against EDTA and restored by addition of $ZnCl_2$ as demonstrated by chemical crosslinking. The binding of the other substrate, all-trans farnesyl pyrophosphate, was independent of divalent cations, as demonstrated by gel filtration. Transfer of the enzyme-bound farnesyl group to the bound $p21^{H-ras}$ required $Mg^{2+}$. Geranylgeranyl pyrophosphate bound to the prenyl pyrophosphate binding site with an affinity equal to that of farnesyl pyrophosphate, but the geranylgeranyl group was not transferred efficiently to $P_{21}^{H-ras}$. It also was not transferred to a modified $p21^{H-ras}$ containing COOH-terminal leucine, a protein that was shown previously to be a good substrate for a rat brain geranylgeranyltransferase-1 (Seabra et al., 1991). The inventors conclude that the protein farnesyltransferase is a metalloenzyme that most likely contains $Zn^{2+}$ at the peptide-binding site. It thus resembles certain metallopeptidases, including carboxy-peptidase A and the angiotensin-converting enzyme. Strategies previously developed to screen for inhibitors of those enzymes will likely aid in the search for inhibitors of the protein farnesyltransferase.

Thus, these data establish several new points about the enzymology of the protein farnesyltransferase from rat brain: 1) the enzyme contains a tightly bound divalent cation, most likely $Zn^{2+}$, that can be removed by dialysis against EDTA; 2) $Zn^{2+}$ is essential for binding of the peptide substrate, and therefore it is probably attached to the β-subunit; 3) the enzyme binds FPP and GGPP with comparable affinities, but transfers only the farnesyl group and only to an acceptor whose CaaX sequence ends in methionine, serine, glutamine, or cysteine, but not leucine; 4) binding of prenyl pyrophosphates does not require any cation; and 5) transfer of the bound farnesyl group to the bound peptide acceptor requires $Mg^{2+}$.

Figure 22:
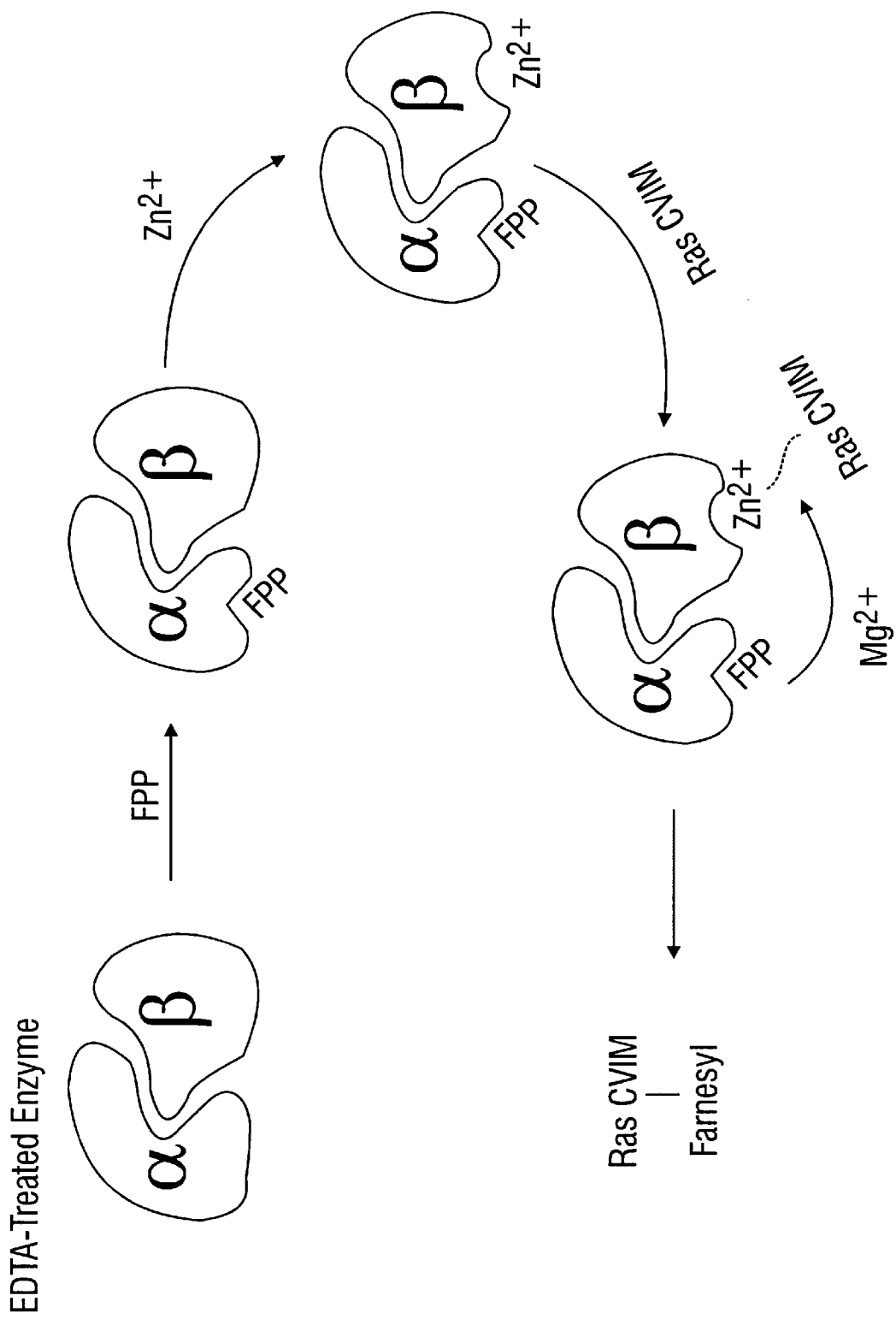
FIG. 22. Schematic Diagram of the Reaction Sequence for EDTA-treated Protein Farnesyltransferase.

The reaction sequence for the EDTA-treated protein farnesyltransferase is summarized graphically in FIG. 22. The EDTA-treated enzyme binds FPP without a requirement for prior $Zn^{2+}$ binding. Peptide binding requires $Zn^{2+}$, but is independent of FPP binding. After both substrates are bound, the transfer reaction occurs in a $Mg^{2+}$-dependent fashion. In the cell the enzyme is expected to be constitutively complexed with $Zn^{2+}$. Under these conditions the mechanism is a simple random-ordered, two-substrate reaction in which the FPP and peptide acceptor can bind to the enzyme in any order.

The requirement for $Zn^{2+}$ in peptide binding is reminiscent of the requirement for $Zn^{2+}$ in certain metallopeptidases, such as carboxypeptidase A (Lipscomb, 1974). In this case the $Zn^{2+}$ coordinates with the carbonyl and amino groups in the peptide bond that will be broken. In the farnesyltransferase the $Zn^{2+}$ is likely to coordinate with the cysteine sulfhydryl group on the acceptor peptide. If this postulated mechanism is correct, inhibitors that mimic peptides that coordinate with $Zn^{2+}$ might be effective inhibitors of the farnesyltransferase. This strategy would be very similar to the strategy followed in the design of inhibitors of the angiotensin-converting enzyme, a zinc metalloenzyme that is mechanistically similar to carboxypeptidase A (Petrillo and Ondetti, 1982).

The ability of GGPP to compete with FPP for the prenyl pyrophosphate binding site on the protein farnesyltransferase creates potential regulatory problems for the cell. If the intracellular concentrations of FPP and GGPP are similar, then the farnesyltransferase might be competitively inhibited at all times. It seems likely that the concentration of GGPP in the cell is lower than that of FPP. FPP is an intermediate in the synthesis of cholesterol, which is the bulk product of the pathway (Goldstein and Brown, 1990). GGPP, on the other hand, is not known to be converted into any other metabolites in animal cells, and indeed its existence in animal cells was not appreciated prior to the discovery of geranylgeranyl-modified proteins (Farnsworth et al., 1990; Rilling et al., 1990). Thus, it seems likely that cells avoid GGPP competition by maintaining the FPP concentration at a higher level than the GGPP concentration.

If the α subunit is involved in prenyl phrophosphate binding and if the α subunit of the farnesyltransferase is identical to that of the leucine-recognizing geranylgeranyltransferase, then the α subunit must behave differently when it is part of the geranylgeranly-transferase. It seems unlikely that the geranylgeranyl-transferase would be inhibited by FPP because this would render the enzyme functionally inactive in the cell. Resolution of this issue will require the purification of the leucine-recognizing geranylgeranyltransferase-1 and the determination as to whether its α subunit is identical to, or merely similar to, the α subunit of the farnesyltransferase.

The binding of prenyl pyrophosphates to the farnesyltransferase appears to be independent of divalent cations. In this regard the farnesyltransferase resembles the prenyltransferase that catalyzes the condensation of isopentenyl pyrophosphate with allylic pyrophosphates to form FPP (King and Rilling, 1977). The two enzymes also resemble each other in the requirement for a divalent cation ($Ng^{2+}$ or $Mn^{2+}$) in the transfer reaction. In studies not shown, it was found that $Mn^{2+}$ will substitute for $Mg^{2+}$ in the protein farnesyltransferase reaction. The two enzymes differ in that the FPP synthetase is a homodimer and it shows no requirement for $Zn^{2+}$ (Rilling, 1985).

Turning to the issue of the yeast counterpart prenyltransferases, very recently two additional putative β subunits of yeast prenyltransferases have been identified, BET2 (Rossi et al., 1991) and CAL1 (Ohya et al., 1991). Both sequences resemble the DPR1/RAM1 gene product and the β subunit of the rat brain farnesyltransferase. A mutation in the BET2 gene prevents the membrane attachment of two small GTP binding proteins (YPT1 and SEC4) that direct vesicular traffic in the yeast secretory pathway (Rossi et al., 1991). These proteins terminate in the sequence CC, which has recently been shown to be geranylgeranylated in animal cells (Khosravi-Far et al., 1991). The second putative β-subunit, encoded by the CAL1 gene, is necessary for yeast to control the cell cycle when deprived of calcium. Based on a genetic argument, it has been suggested that the targets for this prenyltransferase are two proteins that end in a Cys-X-X-Leu (SEQ ID NO:71) sequence and are believed to be geranylgeranylated (Ohya et al., 1991).

Considered together, the yeast and animal studies suggest the existence of a family of closely related β subunits that mediate peptide binding to a variety of prenyltransferases. Whether all of these enzymes have the same α subunit, or whether a family of such subunits also exists, remains to be determined.

EXAMPLE IV

Recombinant Cloning of the Human Farnesyl: Protein Transferase α and β Subunit cDNAs The inventors have now succeeded in cloning cDNAs encoding both the α and β subunits of the human farnesyltransferase. This was carried out using molecular cloning techniques with the aid of the information gained from the rat farnesyltransferase gene disclosed herein.

1. α Subunit Cloning and Sequence Analysis

Approximately $1\times10^6$ plaques from a human retinal λgt10 cDNA library (obtained from Jeremy Nathans, Johns Hopkins University Medical School, Baltimore, Md.) were screened using 32P-labeled probes corresponding to the 5' end of the cDNA for the rat farnesyltransferase α subunit, as disclosed herein and in Chen et al., (1991a). Filters were hybridized at 42° C. in hybridization buffer with 50% (v/v) formamide containing $1\times10^6$ cpm/ml of a single-stranded M13 probe and washed in IXSSC (150 mM sodium chloride and 15 mM sodium citrate, pH7) and 0.5% (w/v) SDS at 55° C.

On screening the human retinal cDNA library with $^{32}$P-labeled probes derived from the rat α subunit cDNA, several positive clones were identified. These were initially characterized by polymerase chain reaction (PCR) using primers corresponding to the right and left arms of λgt10. Positive clones containing the largest inserts were plaque purified, phage DNA prepared, and the cDNA inserts subcloned into the Bluescript (Stratagene) SKII vector for restriction mapping and DNA sequencing (Sanger et al., 1980) using specific oligonucleotides.

Figures 23, 23A, 23B, 23C, 23D:
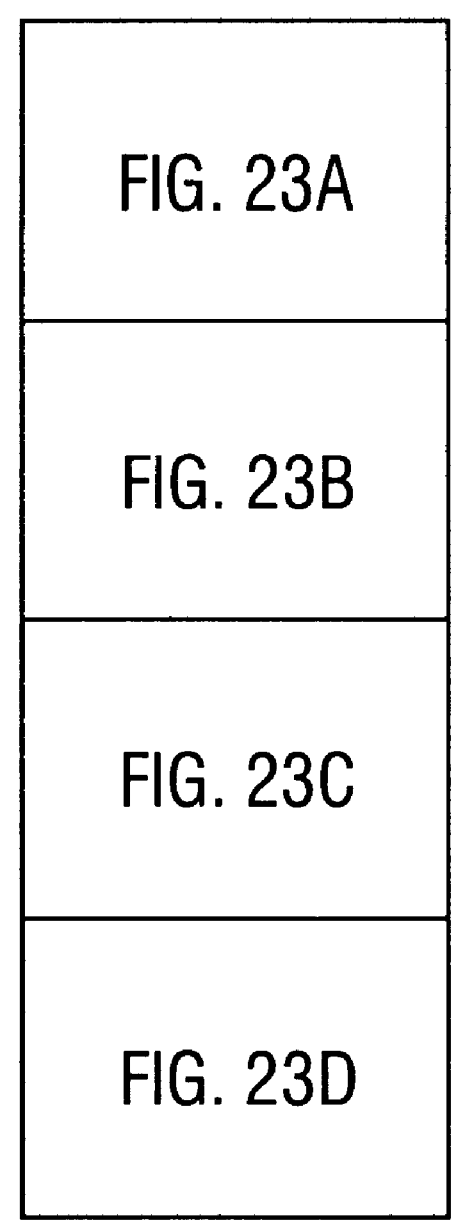

The nucleotide sequence of the human farnesyltransferase α subunit, as encoded by the cloned cDNA, is represented by SEQ ID NO:6. This coding region is followed by a 3'-untranslated region of 524 nucleotides that ends in a poly(A) tail. The cloned cDNA encodes a human α subunit protein of 379 amino acids, represented by SEQ ID NO:5, which is two amino acids longer than the deduced rat sequence (FIG. 23). Overall, the human farnesyltransferase α subunit is 93% identical to the rat α subunit at the protein level (FIG. 23). In the coding region, the nucleotide sequence of the human cDNA is 79% identical to that of the rat.

When introduced together into the human kidney 293 cell line by transfection, the human farnesyltransferase α subunit cDNA and the rat farnesyltransferase β subunit cDNA produced an active enzyme, as was the case when the cDNAs encoding both of the rat subunits were co-transfected into 293 cells (disclosed herein).

2. β Subunit Cloning and Sequence Analysis

PCR was used to produce a probe specific for the human farnesyltransferase β subunit. Human prostate poly (A)+ RNA was subjected to first strand synthesis (Chen et al. 1991a; 1991b), and then used as a template in a PCR reaction with a primer pair developed from the rat farnesyltransferase β subunit, as disclosed herein and in Chen et al., (1991b). The 300 bp amplified product was sequenced and shown to correspond to the human farnesyltransferase β subunit.

On screening $1.5\times10^6$ plaques from the human retinal λgt10 cDNA library with the $^{32}$P-labeled probe corresponding to the PCR-product, 9 positive clones were identified. Positive clones containing the largest inserts were plaque purified, phage DNA prepared, and the cDNA inserts subcloned into M13 and pUC18 vector for restriction mapping and DNA sequencing (Sanger et al., 1980) using the M13 universal sequencing primer.

Figure 24:
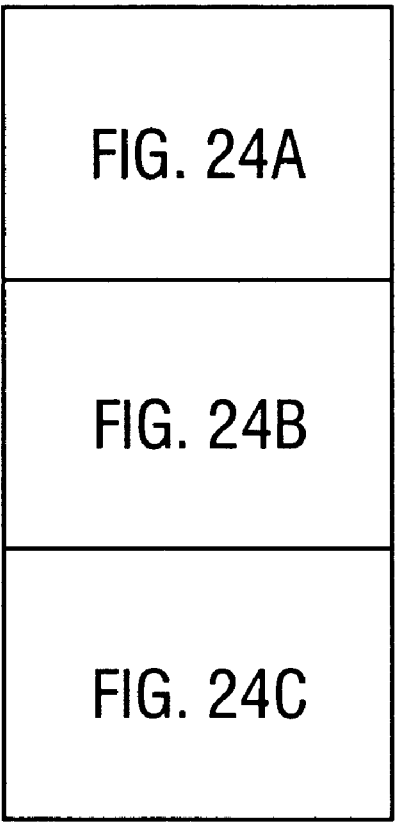
FIG. 24. Nucleotide (SEQ ID NO:8) and Deduced Amino Acid Sequence (SEQ ID NO:7) of a Partial cDNA Encoding the Human Farnesyltransferase β Subunit, and Comparison with the Amino Acid Sequence of the Rat β Subunit. Nucleotides are numbered on the right. Amino acids are numbered on the left with the number in parentheses indicating the corresponding residue in the rat protein. The translated 387 amino acid sequence (SEQ ID NO:7) of the partial human farnesyltransferase β subunit cDNA is shown beneath the nucleotide sequence. Amino acids that differ from the rat protein are boxed and the differences are shown below the human sequence.

The nucleotide sequence of the human farnesyltransferase β subunit, as encoded by the partial cDNA clone obtained, is represented by SEQ ID NO:8. This partial cDNA clone encodes a human β subunit protein of 487 amino acids (SEQ ID NO:7), 50 amino acids shorter than the deduced rat sequence (FIG. 24). Overall, the human farnesyltransferase β subunit is 96% identical to the rat farnesyltransferase β subunit at the protein level (FIG. 24). In the coding region, the nucleotide sequence of the human cDNA (SEQ ID NO:8) is 87% identical to the rat sequence (SEQ ID NO:4).

3. Discussion

In a disease or disorder where the function of CAAX farnesyltransferase and the related prenyltransferase, CAAX geranylgeranyltransferase-1, is potentially important, an abnormality of either the α or β subunit of CAAX farnesyltransferase or CAAX geranylgeranyltransferase might either cause or exacerbate the condition. It would appear that mutations in either the α subunit or the β subunit of farnesyltransferase would have pleiotropic effects because of the number of different proteins and systems that are affected by prenylation. Pleiotropy would be expected to be particularly evident in mutations that affect the farnesyltransferase α subunit since this protein is the a subunit for both the CAAX farnesyltransferase and CAAX geranylgeranyltransferase.

Different mutations in critical regions of the α or β subunits of farnesyltransferase may have a differential effect on individual GTP-binding proteins. For $p21^{ras}$ proteins, farnesylation assists attachment of $p21^{ras}$ to the inner surface of the plasma membrane. It is believed that farnesylation increases the efficiency with which oncogenic ras proteins stimulate cell growth. It is possible that amplification or activating mutations of either the α or β subunits of the farnesyltransferase enzyme may affect tumor cell growth and progression indirectly by increasing the attachment efficiency of $p21^{ras}$ proteins.

EXAMPLE V

Specificity of Prenylation for K-rasB, H-Ras and Chimeric H-Ras Proteins

1. Methods

A. Materials

All-trans-[$^3$H]farnesyl pyrophosphate and all-trans-[$^3$] geranylgeranyl pyrophosphate were purchased from NEN Research Products and American Radiolabeled Chemicals, respectively; pRSET and pTrcHis bacterial expression vectors from Invitrogen; and BL21(DE3) bacteria from Novagen. Various plasmids were obtained from the following: pTrcHis-Rap1B, Doug Andres (University of Kentucky Medical School); rat CAAX geranylgeranyltransferase β-subunit (Zhang et al., 1994), Pat Casey (Duke University Medical School); and pZIP-KRas4B (Casey et al., 1989), Channing Der (University of North Carolina School of Medicine). BZA-2B (James et al., 1993) was provided by James C. Marsters, Jr. and Mark Reynolds of Genentech, Inc., 460 Point San Bruno Blvd., South San Fransisco, Calif. 94080.

B. Bacterial Expression Constructs

All Ras proteins and Rap1B were expressed as fusion proteins in which six histidine residues were placed at the $NH_2$-terminus.

The coding region of human H-Ras was amplified from pRcCMV-H-Ras (James et al., 1994) by PCR and subcloned into the XhoI site of pRSETA (which contains the coding sequence for His$_6$) to yield pRSET-H-Ras.

The human K-RasB coding region was amplified from pZIP-KRas4B by PCR and subcloned into the HindIII and NcoI sites of pRSETB, yielding pRSET-K-Ras4B.

Plasmids encoding chimeric H-Ras proteins were constructed by amplifying a 357-bp fragment of pRcCMV-H-Ras between codon 71 and the stop codon of H-Ras. The 3' PCR primers encoded the desired COOH-terminal amino acids (FIG. 25) followed by a stop codon and a NotI restriction site. Each PCR product was digested with BstXI plus NotI, and the resulting 247-bp fragments were ligated into the corresponding region of pRcCMV-H-Ras. These fragments were introduced into pRSET-H-Ras using a similar domain swap strategy to yield pRSET-H-RasCVIM, pRSET-H-Ras(K$_n$)CVLS, and pRSET-H-Ras (K$_n$) CVIM.

The coding region of Rap1B (Pizon et al., 1988) was amplified by PCR from human lymphocyte B cell cDNA and subcloned into the BamHI site of pTrcHis.

The structures of all plasmids were confirmed by restriction mapping and DNA sequencing of the PCR-amplified fragments. General laboratory techniques are described in Sambrook et al., 1989.

C. Purification of Prenyltransferase Substrates

Plasmids encoding the desired His$_6$-tagged proteins were transformed into BL21(DE3) bacteria. Cultures were grown and the proteins were purified by Ni$^{2+}$-Sepharose® affinity chromatography as previously described (Cremers et al., 1994). Peak fractions were pooled and dialyzed for 16 h in 6 L of buffer containing 20 mM Tris-HCl (pH 7.5), 3 mM MgCl$_2$, 1 mM sodium EDTA, 0.1 M NaCl, 5 mM DTT, and 0.1 mM GDP. The dialyzed proteins were concentrated to 5–20 mg/ml with a Centriprep 10 concentrator (Amicon) and stored in multiple aliquots at –80° C.

D. Production of Recombinant Baculoviruses

A recombinant baculovirus that expresses the β-subunit of rat CAAX geranylgeranyltransferase (Zhang et al., 1994) was constructed. The α-subunit was obtained by subcloning the α-subunit of rat CAAX farnesyltransferase (Example III, Chen et al., 1991a) into the EcoRI and XbaI sites of the baculoviral transfer plasmid pVL1392 (Invitrogen) to yield pVL1392-FTα (James et al., 1993). A 197-bp fragment from this plasmid was amplified by PCR with a 3' primer located beyond the EagI restriction site at codon 40 and a 5' primer designed so that the product would encode a BglII restriction site followed by the amino acid sequence Met-Ala-(His)$_6$ fused to codon 2 of the farnesyltransferase α-subunit. This PCR product was digested with BglII and EagI and subcloned into the corresponding region of pVL1392-FTα to yield pVL1392-(His)$_6$-FTα. The segment amplified by PCR was sequenced on both strands, and this plasmid was then used to construct a recombinant baculovirus according to standard procedures (O'Reilly et al., 1992).

E. CAAX Geranylgeranyltransferase Purification

A 500-ml culture of *Spodoptera frugiperda* (Sf9) cells was coinfected with recombinant baculoviruses that express the geranylgeranyltransferase-1 β-subunit and the His$_6$-farnesyltransferase α-subunit (described above). The cells were harvested 48 h after infection by centrifugation and washed once in 50 mM Tris-HCl (pH 7.5) and 0.1 M NaCl. The cell pellet was resuspended in 30 ml of buffer containing 50 mM Tris HCl (pH 7.5), 0.5 M NaCl, 2 mM MgCl$_2$, 20 μM ZnCl$_2$, 5 mM imidazole, 1 mM β-mercaptoethanol, 3 U/ml DNAse I, 0.5 mM phenylmethylsulfonyl fluoride, and 5 μg/ml each of aprotinin, leupeptin, and pepstatin, and the cells were lysed by 2 passes through a French press. The lysate was centrifuged at 4° C. for 10 min at 10,000 g, and the resulting supernatant was centrifuged for 30 min at 10$^5$ g. His$_6$-tagged geranylgeranyltransferase-1 was purified from the 10$^5$ g supernatant by Ni$^{2+}$-Sepharose® affinity chromatography as described for Rab proteins (Cremers et al., 1994). Peak fractions were pooled and dialyzed for 16 h in 6 L of buffer containing 50 mM Tris HCl (pH 7.5), 0.1 M NaCl, 1 mM DTT, and 20 μM ZnCl$_2$. The dialyzed enzyme was concentrated to ~1 mg/ml with a Centriprep 10 concentrator and stored in multiple aliquots at –80° C.

P. Prenyltransferase Assays

The standard assay used was based upon that described herein above (in Examples I and II), with the following modifications. CAAX geranylgeranyltransferase assays were performed in 12×75 glass tubes in a final volume of 50 μl. Each reaction contained 50 mM sodium Hepes (pH 7.2), 5 mM MgCl$_2$, 1 mM DTT, 0.3 mM Nonidet P-40, 0.5 μM [$^3$H]GGPP (33,000 dpm/pmol), 100 ng of purified recombinant His$_6$-tagged geranylgeranyltransferase-1, and various concentrations of the desired recombinant His$_6$-tagged protein substrate. Each protein substrate was diluted to 5 times the desired final concentration with 50 mM sodium Hepes (pH 7.2) and added to the reaction in a volume of 10 μl. Following a 30-min incubation at 37° C., the amount of [$^3$H]geranylgeranyl transferred to each substrate was measured by precipitation with ethanol/HCl (Pompliano et al., 1992) with minor modification as previously described (Seabra et al., 1993).

CAAX farnesyltransferase assays were performed with purified recombinant rat as previously described (James et al., 1993). Each reaction, in a final volume of 50 μl, contained 50 mM sodium Hepes (pH 7.2), 5 mM MgCl$_2$, 20 mM KCl, 1 mM DTT, 0.2% (w/v) octyl-β-D-glucoside, 0.5 or 0.6 μM [$^3$H]FPP (14,093 to 16,876 dpm/pmol), 20 ng of recombinant farnesyltransferase, and various concentrations of the desired His$_6$-tagged protein substrate. After incubation for 30 min at 37° C., the amount of [$^3$H]farnesyl transferred to each substrate was measured by ethanol/HCl precipitation as described above.

2. Results

FIG. 25 shows the COOH-terminal sequences of H-Ras, K-rasB, and the three chimeric versions that were used in the present study. The chimeras were designed to contain the protein sequence of H-Ras into which was substituted different COOH-terminal sequences form K-rasB. The polylysine sequence of K-rasB "KKKKKKSKTK" (SEQ ID NO:77) was partially incorporated to obtain a chimeric H-Ras protein with a COOH-terminal sequence of "KKKKKKSKSCKCVLS", H-Ras($_n$)CVLS (SEQ ID NO:75). The K-rasB tetrapeptide sequence CVIM (SEQ ID NO:10) was incorporated to obtain a chimeric H-Ras protein with a COOH-terminal sequence of "DESGPGCMSCKCVIM", H-RasCVIM (SEQ ID NO:75). Finally both the polylysine sequence (SEQ ID NO:77) and the tetrapeptide (SEQ ID NO:10) was incorporated to obtain a chimeric H-Ras protein with a COOH-terminal sequence KKKKKKSKTKCVIM, H-Ras(K$_n$)CVIM (SEQ ID NO:73). FIG. 25 also shows the COOH-terminal sequence of Rap1B (SEQ ID NO:76), which terminates in leucine, and is a classic substrate for geranylgeranyltransferase-1 (Kawata et al., 1990).

Figure 26A:
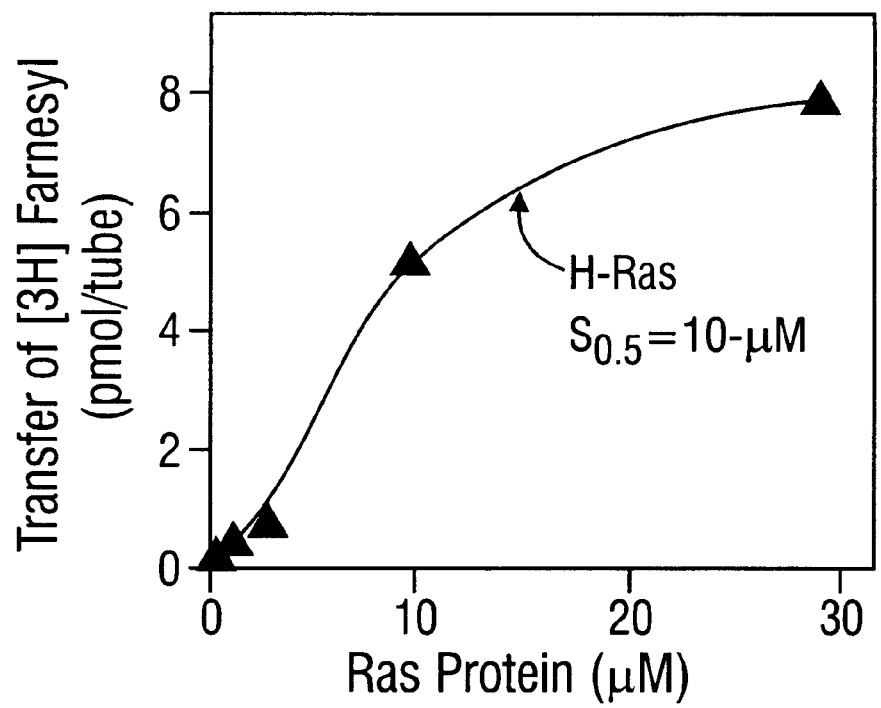
FIG. 26A. Saturation curves for various Ras proteins Farnesylated by recombinant CAAX farnesyltransferase. Each reaction contained 20 ng of recombinant farnesyltransferase, 0.6 μM [$^3$H]FPP (farnesyl pyrophosphate) (14,093 dpm/pmol), and the indicated concentration of H-Ras (▲). After incubation for 30 min at 37° C., the amount of [$^3$H]farnesyl transferred to each protein was determined as described in Example V. A blank value, determined in parallel reactions containing no protein substrate, was subtracted from each value (0.04 pmol). Each value is the average of duplicate determinations.
Figure 26B:
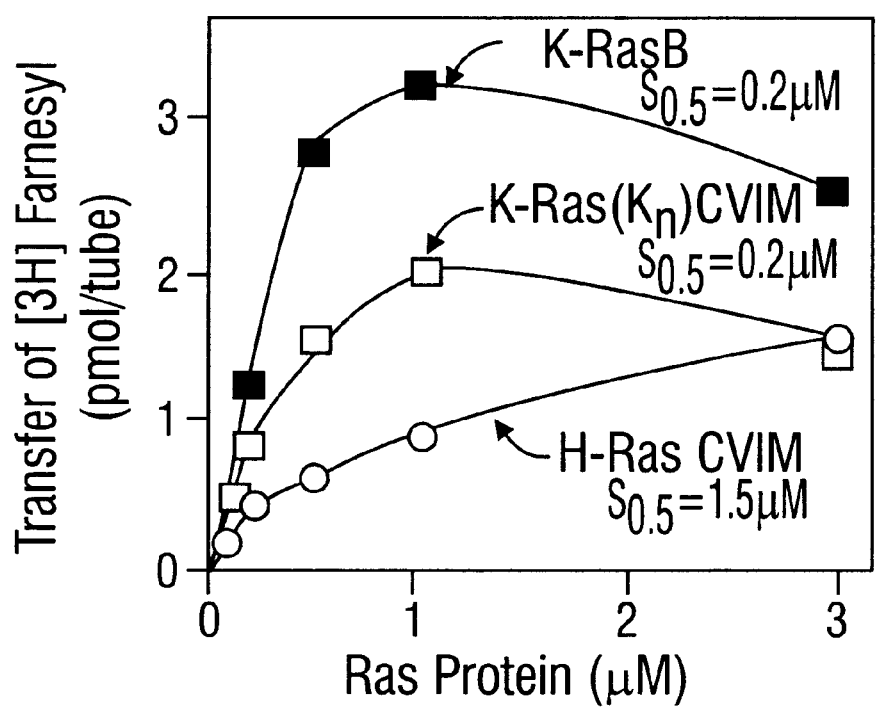
FIG. 26B. Saturation curves for various Ras proteins Farnesylated by recombinant CAAX farnesyltransferase. Conditions were as described in FIG. 26A. Each reaction contained 20 ng of recombinant farnesyltransferase, 0.6 μM [$^3$H]FPP (farnesyl pyrophosphate) (14,093 dpm/pmol), and the indicated concentration of K-rasB (■), or the indicated chimeric H-Ras (≡, ○, Δ.
Figure 26C:
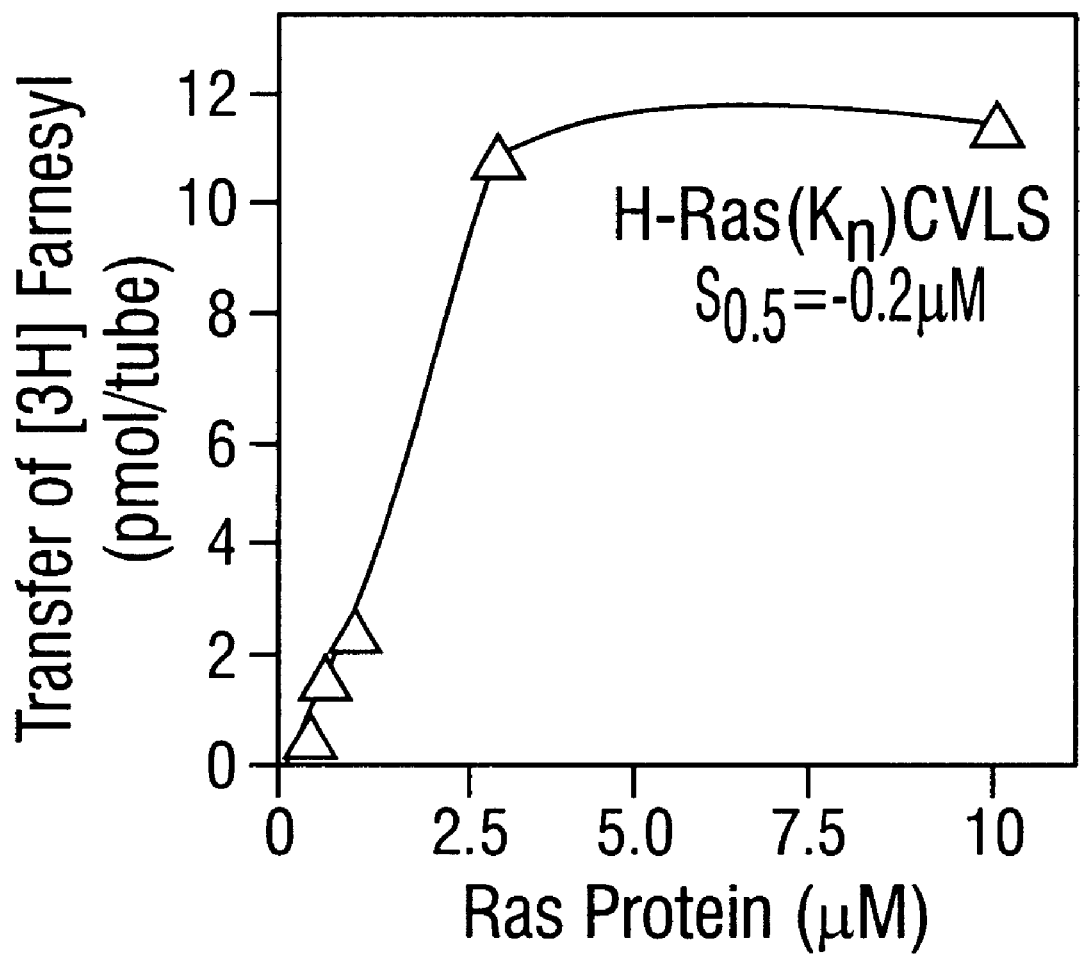
FIG. 26C. Saturation curves for various Ras proteins Farnesylated by recombinant CAAX farnesyltransferase. Conditions were as described in FIG. 26A. Each reaction contained 20 ng of recombinant farnesyltransferase, 0.6 μM [$^3$H]FPP (farnesyl pyrophosphate) (14,093 dpm/pmol), and the indicated concentration of H-Ras(Kn)CVLS.

A. Saturation Curves for Ras Proteins Farnesylated by Farnesyl:Protein Transferase FIG. 26A, FIG. 26B and FIG. 26C show saturation curves for the CAAX farnesyltransferase reaction as a function of Ras concentration using recombinant rat farnesyltransferase purified from Sf9 insect cells. As previously noted (Example I, Reiss et al., 1990; Pompliano et al., 1993), these saturation curves were not simple rectangular hyperbolae. To compare the relative affinities for the different Ras proteins, the $S_{0.5}$ value was calculated, which is defined as the substrate concentration that gives approximately 50% of the maximum velocity obtained in the study. The saturation curve for H-Ras was sigmoidal, and the $S_{0.5}$ was ~10 μM (A). The maximum velocity for K-rasB was lower than that for H-Ras (FIG. 26B), and there was evidence of substrate inhibition at higher concentrations. The calculated $S_{0.5}$ was 0.2 μM, which was 50-fold lower than the $S_{0.5}$ for H-Ras. Replacement of the COOH-terminal sequence of H-Ras CVLS (SEQ ID NO:19) with the COOH-terminal sequence of K-rasB CVIM (SEQ ID NO:10) to obtain H-RasCVIM (SEQ ID NO:74), lowered the $S_{0.5}$ value by approximately 6-fold (1.5 μM). Insertion of the polylysine sequence of K-rasB into H-Ras, H-Ras(Kn)CVLS (SEQ ID NO:75), also lowered the $S_{0.5}$ by 5-fold (FIG. 26C). Insertion of both the polylysine sequence and CVIM into H-Ras, H-Ras(Kn)CVIM (SEQ ID NO:73), lowered the $S_{0.5}$ by a further 10-fold, which now approximated the $S_{0.5}$ value for K-rasB (0.2 μM) (FIG. 26B). These data indicate that the apparent high affinity of farnesyltransferase for K-rasB is attributable both to the polylysine sequence (SEQ ID NO:77) and to the COOH-terminal CVIM (SEQ ID NO:10).

B. BSA-2B Mediated Inhibition of Farnesylation of Ras Proteins

Figures 27A, 27B:
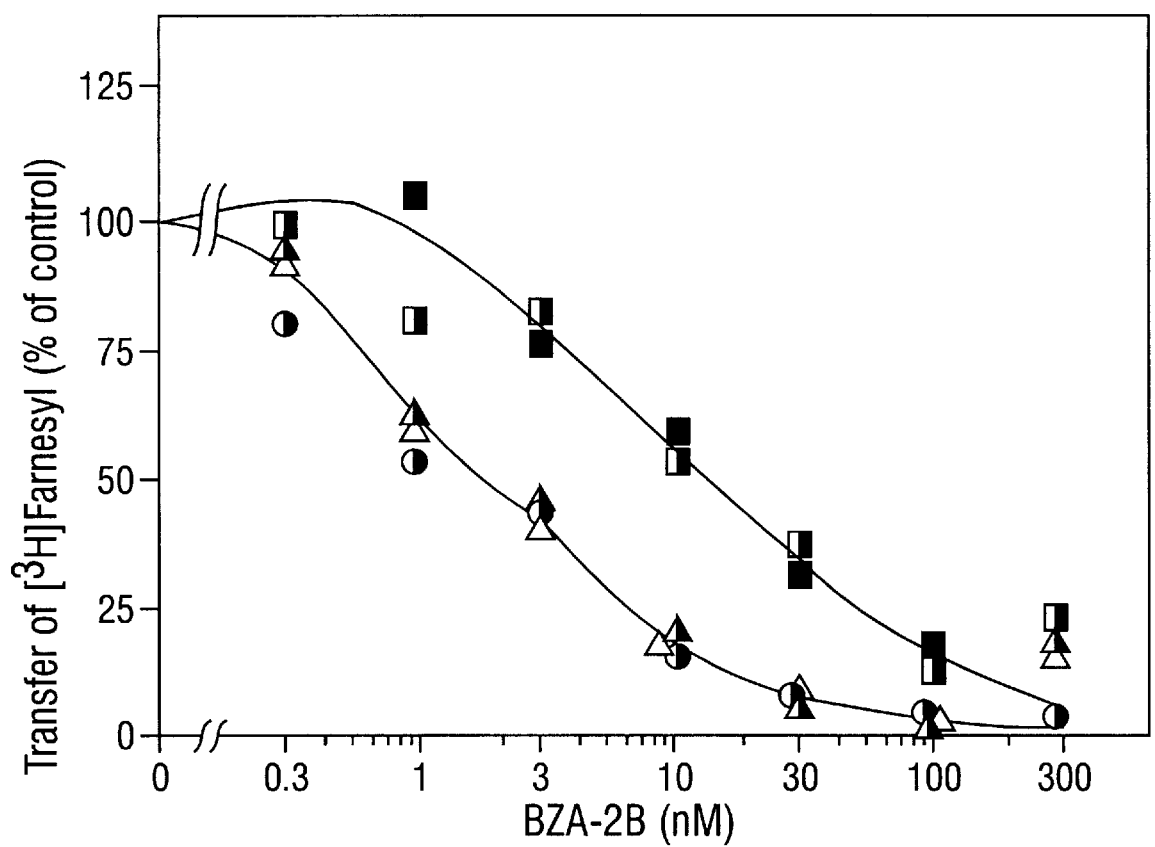
FIG. 27A. BZA-2B mediated inhibition of farnesylation of various Ras proteins. Each reaction contained 20 ng of recombinant farnesyltransferase, 0.6 μM [$^3$H]FPP (16,876 dpm/pmol), the indicated concentration of BZA-2B, and one of the following native or chimeric Ras proteins: 20 μM H-Ras, 0.5 μM K-rasB, 2 μM H-RasCVIM, 3 μM H-Ras(K$_n$)CVLS, or 0.5 μM H-Ras(K$_n$)CVIM. BZA-2B was dissolved in dimethylsulfoxide and added to the reactions as described previously (James et al., 1993). After a 30-min incubation at 37° C., the amount of [$^3$H]farnesyl transferred to each protein was determined as described in Example V. Each value represents a single incubation, except for the values taken as 100%, which are the average of triplicate determinations. The "100% of control" values were 9.9 (Δ), 4.1 (■), 2.9 (○), 11.8 (▲), and 4.5 (≡) pmol/tube. A blank value, determined in parallel reactions containing no protein substrate, was subtracted from each value (0.03 pmol).
FIG. 27B. BZA-2B mediated inhibition of farnesylation of various Ras proteins. The approximate concentration of BZA-2B required to inhibit 50% of the farnesylation of each substrate was determined from the appropriate curve in FIG. 27A.

The ability of BZA-2B to inhibit farnesylation of the various Ras proteins was compared (FIG. 27A and FIG. 27B). A concentration of each Ras protein that was approximately 2-fold above the $S_{0.5}$ value was used. Under these conditions, an 8-fold higher concentration of BZA-2B was required for 50% inhibition of farnesylation of K-rasB as opposed to H-Ras (13 nM vs. 1.6 nM, FIG. 27B). Resistance to inhibition was not conferred when either the COOH-terminal CVIM or the polylysine sequence was inserted separately into H-Ras (SEQ ID NO:74 or SEQ ID NO:75, respectively). However, when the two sequences were inserted together (SEQ ID NO:73), the $I_{0.5}$ value increased to that seen with K-rasB. These data indicate that the farnesylation of K-rasB is relatively resistant to inhibition by BZA-2B and that this resistance is attributable to a combination of the effects of the polylysine sequence (SEQ ID NO:77) and the CVIM (SEQ ID NO:10). This resistance is not restricted to the benzodiazepine class of inhibitors. When compared to farnesylation of H-Ras, K-rasB showed a 10 to 20-fold higher resistance to inhibition by CVFM (SEQ ID NO:34), a tetrapeptide inhibitor of farnesyltransferase (James et al., 1993).

Figures 28A, 28B:
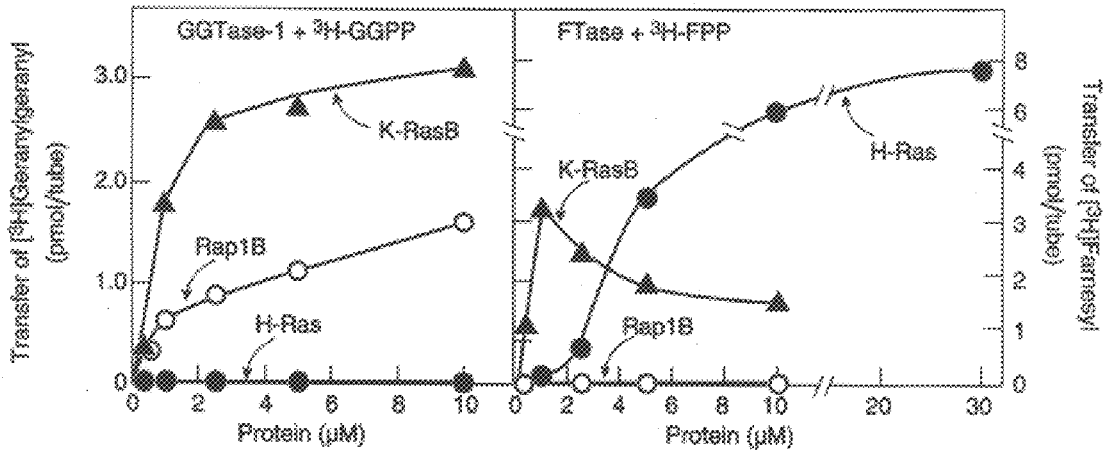
FIG. 28A. Prenylation of K-RaB (▲), H-Ras (●), and Rap1B (○) by recombinant geranylgeranyltransferase-1. Each reaction contained 100 ng of recombinant geranylgeranyltransferase-1, 0.5 μM [$^3$H]GGPP (geranylgeranyl pyrophosphate) (33,000 dpm/pmol), and the indicated concentration of K-rasB (▲), H-Ras (●), or Rap1B (○). After incubation for 30 min at 37° C., the amount of $^3$H-prenyl group transferred to each protein was determined as described in Example V. A blank value, determined in parallel reactions containing no protein substrate, was subtracted from each value (0.04 pmol). Each value is the average of duplicate determinations.
FIG. 28B. Prenylation of K-rasB (▲), H-Ras (●), and Rap1B (○) by recombinant CAAX farnesyltransferase. Each reaction contained 20 ng of recombinant farnesyltransferase, 0.5 μM [³H]FPP (16,244 dpm/pmol), and the indicated concentration of K-rasB (▲), H-Ras (●), or Rap1B (○). After incubation for 30 min at 37° C., the amount of ³H-prenyl group transferred to each protein was determined as described in Example V. A blank value, determined in parallel reactions containing no protein substrate, was subtracted from each value (0.04 pmol). Each value is the average of duplicate determinations.

C. Prenylation of K-rasB, H-Ras and Rap1B by Geranylgeranyltransferase-1 and CAAX Farnesyl Transferase Whether K-rasB is a substrate for recombinant rat geranylgeranyltransferase-1, purified from Sf9 insect cells, was determined. The activity of this enzyme with the activity of recombinant rat farnesyltransferase was compared (FIG. 28A and FIG. 28B). Surprisingly, geranylgeranyltransferase-1 was able to transfer [³H] geranylgeranyl from [³H]GGPP to K-rasB (FIG. 28A). The affinity for K-rasB was about the same as the affinity for Rap1B, an authentic leucine-terminated substrate for geranylgeranyltransferase-1, and the maximum velocity appeared to be higher for K-rasB than for Rap1B. Geranylgeranyltransferase-1 did not transfer geranylgeranyl groups to H-Ras (FIG. 28A).

Figure 28C:
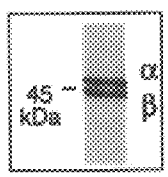
FIG. 28C. ~5 μg of recombinant geranylgeranyltransferase-1 was subjected to electrophoresis on an 8% SDS-polyacrylamide mini-gel and visualized by staining with Coomassie Blue. The α- and β-subunits of each enzyme are denoted on the right. The position of the 45-kDa molecular mass standard is indicated on the left.
Figure 28D:
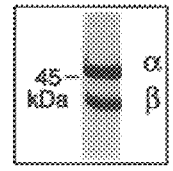
FIG. 28D. ~5 μg of recombinant farnesyltransferase was subjected to electrophoresis on an 8% SDS-polyacrylamide mini-gel and visualized by staining with Coomassie Blue. The α- and β-subunits of each enzyme are denoted on the right. The position of the 45-kDa molecular mass standard is indicated on the left.
Figure 29:
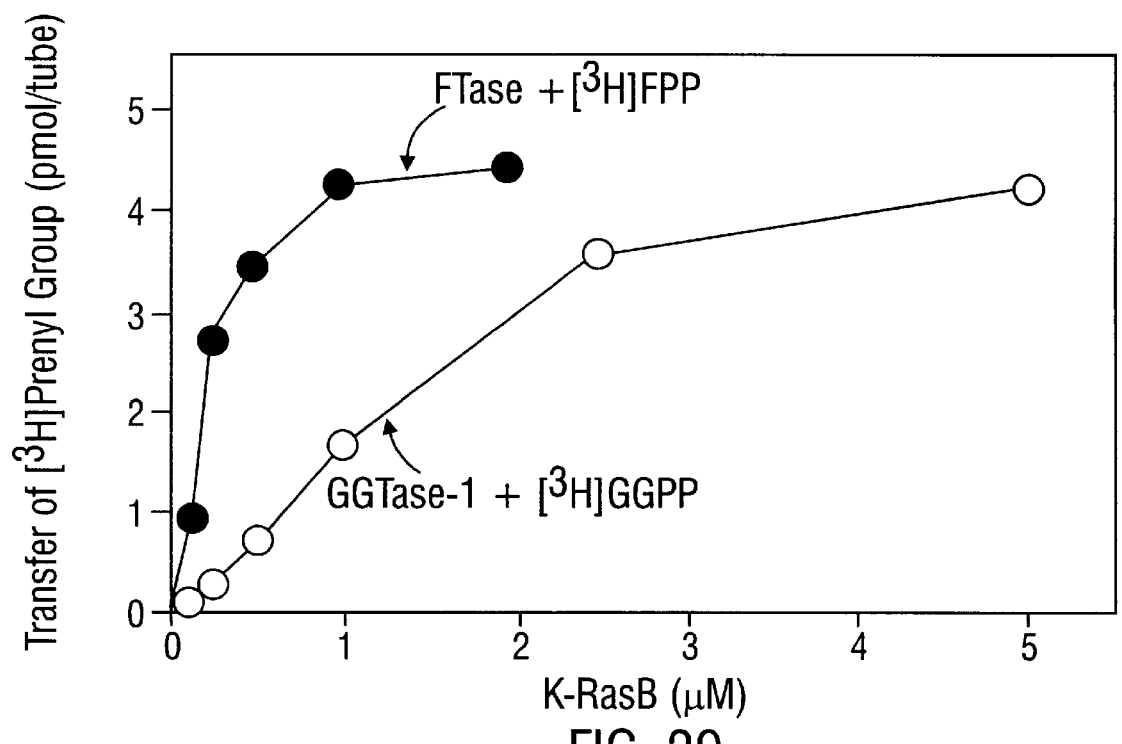
FIG. 29. Saturation curves for K-rasB prenylated by recombinant CAAX farnesyltransferase (●) or geranylgeranyltransferase-1 (○). Assays were performed at 37° C. for 30 min as described in Example V in the presence of either 20 ng recombinant farnesyltransferase and 0.5 μM [³H]FPP (15,234 dpm/pmol) (●) or 100 ng recombinant geranylgeranyltransferase-1 and 0.5 μM [³H]GGPP (33,000 dpm/pmol) (○) and the indicated concentrations of K-RasB. Blank values determined in parallel reactions in the absence of K-RasB (0.03 pmol for each enzyme) were subtracted from each value. Each value is the average of duplicate determinations.
Figure 30:
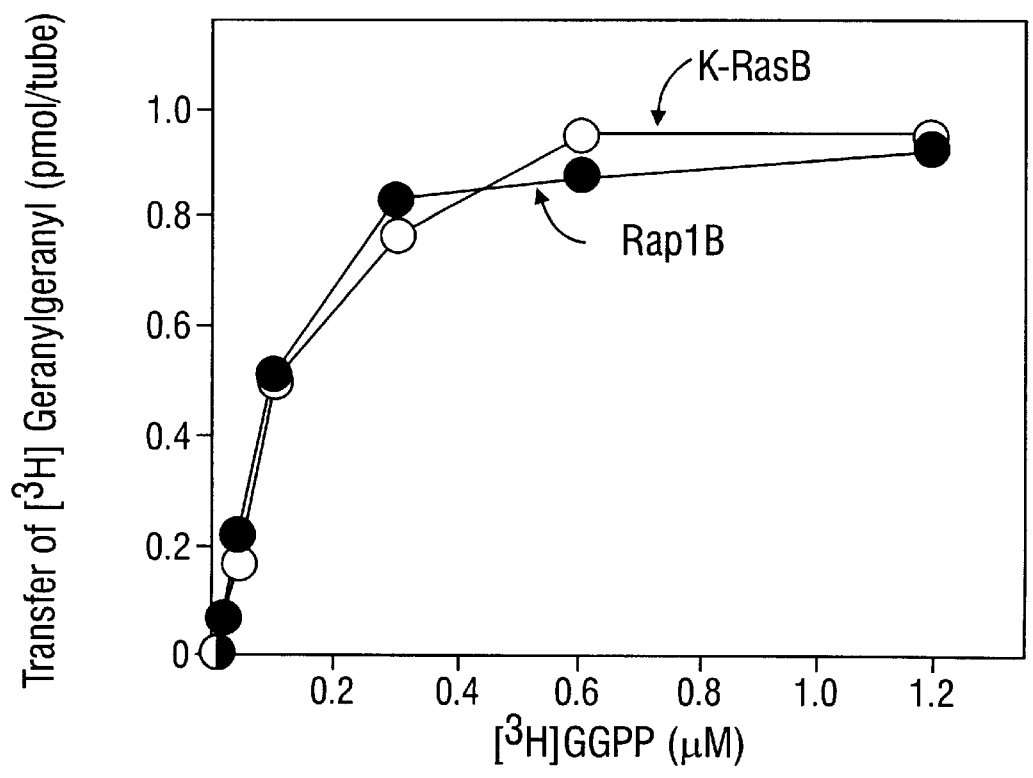
FIG. 30. Saturation curves for [³H]GGPP in a geranylgeranyltransferase-1 assay with Rap1B (●) or K-rasB (○) as protein substrate. Assays were performed at 37° C. for 30 min as described in Example V in the presence of 100 ng recombinant geranylgeranyltransferase-1, either 1 μM K-RasB (○) or 3 μM Rap1B (●), and the indicated concentration of [³H]GGPP (33,000 dpm/pmol). Blank values ranging from 0.005 to 0.025 pmol were determined at each [³H]GGPP concentration in the absence of protein substrate and subtracted from the appropriate value. Each value is the average of duplicate determinations.

For comparative purposes, FIG. 28B shows the farnesylation of the Ras proteins by farnesyltransferase in the same study as that shown in FIG. 28A. As shown in FIG. 26B, the enzyme farnesylated K-rasB with high affinity, and it also farnesylated H-Ras. The enzyme did not transfer farnesyl to Rap1B. FIG. 28C and FIG. 28D illustrate the α- and β-subunits of recombinant geranylgeranyltransferase-1 and farnesyltransferase, respectively, by Coomassie Blue staining. FIG. 29 compares the farnesylation and geranylgeranylation of K-rasB by farnesyltransferase and geranylgeranyltransferase-1 respectively. The $S_{0.5}$ values for the farnesyltransferase and geranylgeranyltransferase~1 were ~0.3 μM and 1.5 μM, respectively. The affinity of geranylgeranyltransferase-1 for [³H]GGPP, calculated by Lineweaver-Burke plots, was similar with K-rasB or Rap1B as substrates (FIG. 30). In both cases a hyperbolic saturation curve was obtained, and the calculated $K_m$ values were 0.17 and 0.13 μM, respectively.

D. Saturation Curves for Various Ras Proteins Prenylated by Recombinant Geranylgeranyltransferase-1

Figure 31A:
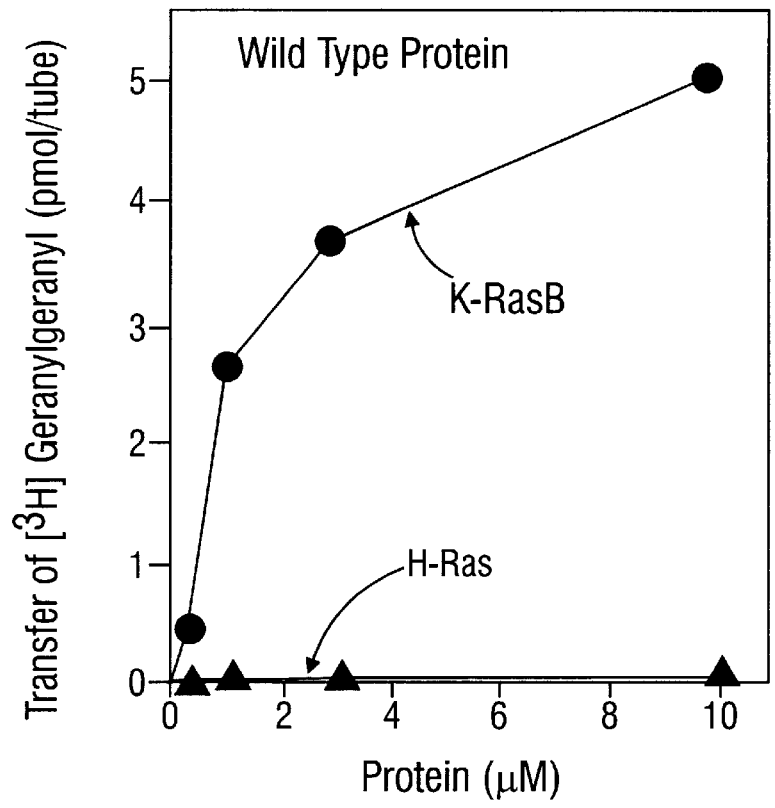
FIG. 31A. Saturation curves for various Ras proteins prenylated by recombinant geranylgeranyltransferase-1. Assays were performed at 37° C. for 30 min as described in Example V. Recombinant geranylgeranyltransferase-1 (100 ng) was incubated with 0.5 μM [³H]GGPP (33,000 dpm/pmol) and the indicated concentration of either wild-type H-Ras (▲) or wild-type K-RasB (●). A blank value determined in a parallel reaction containing no Ras substrate (0.04 pmol) was subtracted from each value. Each value is the average of duplicate determinations.
Figure 31B:
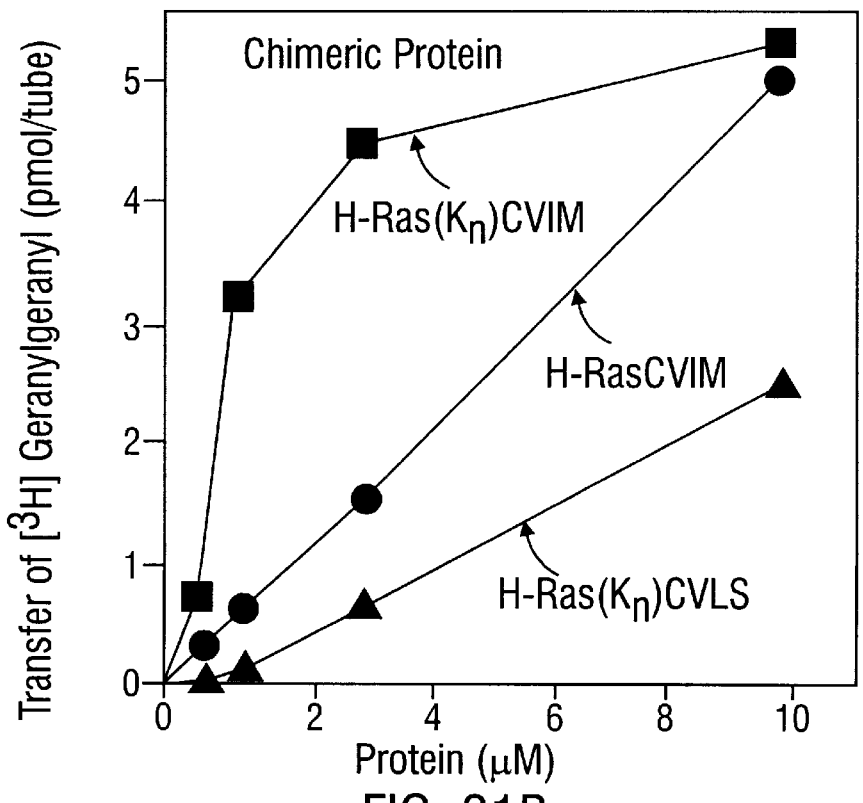
FIG. 31B. Saturation curves for various Ras proteins prenylated by recombinant geranylgeranyltransferase-1. Conditions were as described in FIG. 31A, except that the indicated chimeric H-Ras protein (FIG. 25) was used as a substrate. A blank value determined in a parallel reaction containing no Ras substrate (0.04 pmol) was subtracted from each value. Each value is the average of duplicate determinations.

To determine the structural features of K-rasB that are responsible for its ability to act as a substrate for geranylgeranyltransferase-1, the inventors studied the various chimeric proteins (FIG. 31B). As shown above, geranylgeranyltransferase-1 attached geranylgeranyl groups to K-rasB, but not to H-Ras (FIG. 31A). Insertion of the polylysine sequence of K-rasB into H-Ras increased its ability to act as a substrate, but the apparent affinity remained relatively low (A in FIG. 31B). A similar low affinity was obtained when the inventors substituted the COOH-terminal sequence of K-rasB (CVIM) into H-Ras (● FIG. 31B). However, when both substitutions were made, the affinity of chimeric H-Ras became similar to that of authentic K-rasB (■ FIG. 31B). In studies the inventors found that BZA-2B inhibited the geranylgeranylation of K-rasB by geranylgeranyltransferase-1 ($I_{0.5}$ ~50 nM), whereas it did not inhibit the geranylgeranylation of Rap1B at concentrations up to 3 μM.

3. Discussion

The results demonstrate that the prenylation of K-rasB in vitro differs profoundly from the previously described process for prenylation of H-Ras (Example II, Reiss et al., 1990; Pompliano et al., 1993; Reiss et al., 1992; Brown and Goldstein, 1993; Casey, 1992; Reiss et al., 1991; Moores et al., 1991). In comparison with H-Ras, K-rasB exhibits: (1) a 50-fold higher affinity for CAAX farnesyltransferase; (2) an 8-fold decrease in sensitivity to the farnesyltransferase inhibitor BZA-2B; and (3) a susceptibility to high affinity geranylgeranylation by geranylgeranyltransferase-1. All of these properties of K-rasB are attributable to the combined effects of the CAAX box (CVIM, SEQ ID NO:10) and the polylysine sequence (SEQ ID NO:77) immediately preceding the CAAX box.

Previous studies of the substrate specificity of CAAX farnesyltransferase have used short peptides corresponding to the various CAAX sequences (Example II, Reiss et al., 1991; Moores et al., 1991) or variants of yeast Ras that were mutagenized so as to change the sequence of the CAAX box (Pompliano et al., 1993; Gibbs et al., 1989). These studies concluded that the kinetics of the farnesyl transfer reaction were complex and that the nature of the prenyl pyrophosphate substrate determined in part the relative affinities of the enzyme for different CAAX boxes (Pompliano et al., 1993). None of these studies, including those in previous examples used authentic mammalian K-rasB sequence (SEQ ID NO:73) with its polylysine sequence upstream of the CVIM.

James et al. (1994) found that BZA-5B, a benzodiazepine peptidomimetic, inhibited the farnesylation of H-Ras in wild-type animal cells at concentrations that neither inhibited cell growth nor blocked the acute response to EGF. Both of the latter processes are thought to require prenylated Ras. These findings could be explained most simply if the cells contained a form of Ras whose prenylation was not inhibited by BZA-5B.

These studies show that prenylation of K-rasB is not inhibited efficiently by BZA-5B or by the BZA-2B that is produced from BZA-5B within the cell. Prenylation might persist for either of two reasons: (1) farnesylation of K-rasB is not inhibited by the same concentrations of BZA-5B that inhibit the farnesylation of H-Ras; and (2) K-rasB, but not H-Ras, can be geranylgeranylated by geranylgeranyltransferase-1 in a reaction that is resistant to inhibition by BZA-5B. Previous studies have shown that geranylgeranylated Ras proteins support transformation of animal cells (Cox et al., 1992) and growth of yeast cells (Trueblood et al., 1993).

It is difficult to predict the proportion of farnesylated and geranylgeranylated K-rasB that exists in animal cells. In vitro, K-rasB has a similar affinity for geranylgeranyltransferase-1 as does Rap1B, an authentic leucine-terminated substrate. However, the intracellular concentrations of GGPP and FPP are unknown, as are the concentrations of the non-farnesylated Ras substrates. In addition, it is likely that the geranylgeranyltransferase-1 uses GGPP that is metabolically channeled from the GGPP synthetase, and this may alter the affinity of the enzyme for different protein substrates.

Only one previous study determined the nature of the prenyl group attached to Ras proteins in animal cells (Casey et al., 1989). This study was performed before the existence of geranylgeranyl modifications was widely recognized. The authors showed that Ras proteins, including K-ras4B, contained covalently bound [$^3$]farnesyl derived from [$^3$]mevalonic acid. These studies were not designed to search for relatively small amounts of another isoprenoid such as geranylgeranyl. It is therefore not know whether K-rasB contains any geranylgeranyl groups in vivo. Although cells may preferentially attach farnesyl residues to K-rasB under normal conditions, it is possible that they switch to geranylgeranyl when the farnesyltransferase is inhibited by a compound such as a benzodiazepine peptidomimetic.

Kohl et al. (1994) reported that a non-benzodiazepine CAAX peptidomimetic, L-739,749, inhibits the anchorage-independent growth of Rat-1 cells transformed with oncogenic K-ras4B, as well as with other forms of oncogenic Ras, but not Raf-transformed cells. It is not clear that the growth inhibition is attributable solely to inhibition of Ras farnesylation since this compound also inhibits the anchorage-dependent growth of nontransformed Rat-1 cells (Prendergast et al., 1994). It also exerts effects on the cytoskeleton that are believed to be independent of Ras farnesylation (Prendergast et al., 1994). Data on the ability of L-739,749 to inhibit farnesylation or geranylgeranylation of native or oncogenic K-rasB in vitro have not been reported.

The results together with previous data (Examples I, II, III and IV, Pompliano et al., 1993; Reiss et al., 1992; Seabra et al., 1991; Reiss et al., 1991; Yokoyama et al., 1991; Trueblood et al., 1993; Pompliano et al., 1992) indicate that the CAAX prenyltransferases are highly unusual two-substrate enzymes with substrate specificities that are plastic and can be overlapping.

The two enzymes share a common a-subunit, whose catalytic role has not yet been defined (Example III, Reiss et al., 1992; Moomaw and Casey, 1992; Yokoyama and Gelb, 1993; Seabra et al., 1991; Andres et al., 1993). The farnesyltransferase forms a stable noncovalent complex with FPP (Reiss et al., 1992; Reiss et al., 1991). This binding is inhibited competitively by GGPP. Whereas the bound FPP is transferred to H-Ras, the bound GGPP is not (Reiss et al., 1992). Geranylgeranyltransferase-1 also forms a stable complex with GGPP and to a lesser extent with FPP (Yokoyama and Gelb, 1993). This enzyme appears able to transfer both prenyl groups (Yokoyama and Gelb, 1993).

In general, the COOH-terminal amino acid of the CAAX box determines specificity for the two enzymes (Brown and Goldstein, 1993; Reiss et al., 1991; Moores et al., 1991). Methionine-terminated CAAX boxes such as CVIM have only low affinity for geranylgeranyltransferase-1 (Moores et al., 1991; Kohl et al., 1994). The results presented herein, show that the affinity of the geranylgeranyltransferase-1 for the methionine-terminated CAAX box of K-rasB is enhanced markedly by the polylysine stretch immediately upstream of the CAAX box (FIG. 31B). The polylysine sequence also increases the affinity of K-rasB for farnesyltransferase (FIG. 26A, FIG. 26B and FIG. 26C). Both CAAX prenyltransferases must contain a binding site for the polylysine sequence, most likely on the α-subunit that is shared by the two enzymes.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for or teach methodology, techniques and/or compositions employed herein.

Akada, R., et al. (1989), *Molec. Cell. Biol.,* 9:3491–3498.
Akusjärvi, G., Svensson, C., and Nygard, O. (1987), *Molec. Cell. Biol.* 7:549–551.
Andersson, S., Davis, D. L., Dahlbäck, H., Jörnvall, H. and Russell, D. W. (1989), *J. Biol. Chem.* 264:8222–8229.
Andres, D. A., Goldstein, J. L., Ho, Y. K., and Brown, M. S. (1993) *J. Biol. Chem.* 268:1383–1390.
Ashby, M. N., and Edwards, P. A. (1990), *J. Biol. Chem.* 265:13157–13164.
Aviv, H., et al. (1972), *Proc. Natl. Acad. Sci. USA,* 69:1408–1412.
Barbacid (1987), *Ann. Rev. Biochem.,* 56:779–827.
Bos, J. (1989), *Cancer Res.,* 49:4682–4689.
Brown, M. S. and Goldstein, J. L. (1993) *Nature* 366:14–15.
Capon et al., "Activation of Ki-ras2 gene in human colon and lung carcinomas by two different point mutations," *Nature,* 304:507–513, 1983.

Casey, P. J. (1992) *J. Lipid Res.* 33:1731–1740.
Casey, P. J., et al. (1989), *Proc. Natl. Acad. Sci. U.S.A.*, 86:8323–8327.
Chen, W-J., Andres, D. A., Goldstein, J. L., and Brown, M. S. (1991a), *Proc. Natl. Acad. Sci. USA*, 88:11368–11372.
Chen, W-J., Andres, D. A., Goldstein, J. L., Russell, D. W. and Brown, M. S. (1991b), *Cell* 66:327–334.
Chen, W-J., Moomaw, J. F., Overton, L., Kost, T. A., and Casey, P. J. (1993) *J. Biol. Chem.* 268:9675–9680.
Chirgwin, J. M., et al. (1979), *Biochemistry,* 18:5294–5303.
Cox, A. D., Hisaka, M. M., Buss, J. E., and Der, C. J. (1992) *Mol. Cell. Biol.* 12:2606–2615.
Cremers, F. M., Armstrong, S. A., Seabra, M. C., Brown, M. S., and Goldstein, J. L. (1994) *J. Biol. Chem.* 269:2111–2117.
Crews, C. M. and Erikson, R. L. (1993) *Cell* 74:215–217.
Davisson, V. J., et al. (1986), *J. Org. Chem.,* 51:4768–4779.
Egan, S. E. and Weinberg, R. A. (1993) *Nature* 365:781–783.
Farnsworth, D. C., et al. (1989), *J. Biol. Chem.,* 264:20422–20429.
Farnsworth, C. C., Gelb, N. H., Glomset, J. A. (1990), *Science,* 247:320–322.
Feig, L. A., et al. (1986), *Proc. Natl. Acad. Sci. U.S.A.*, 83:4607–4611.
Frohman, M. A., et al. (1988), *Proc. Natl. Acad. Sci. USA,* 85:8998–9002.
Gautam, N., et al. (1989), *Science,* 244:971–974.
Gibbs, J. B., Schaber, M. D., Schofield, T. L., Scolnick, E. M., and Sigal, I. S. (1989) *Proc. Natl. Acad. Sci. USA* 86:6630–6634.
Gibbs, J. B., Oliff, A., and Kohl, N. E. (1994) *Cell* 77:175–178.
Gibbs, J. B., et al. (1989) *Micro Rev.,* 53:171–185.
Glisin, V., et al. (1974) *Biochemistry,* 13:2633–2640.
Goldstein, J. L., Brown, M. S., Stradley, S. J., Reiss, Y., and Gierasch, L. M. (1991), *J. Biol. Chem.,* 266:15575–15578.
Goldstein, J. L. and Brown, M. S. (1990), *Nature,* 343:425–430.
Goodman, L. E., Judd, S. R., Farnsworth, C. C., Powers, S., Gelb, M. H., Glomset, J. A., and Tamanoi, F. (1990), *Proc. Natl. Acad. Sci. USA,* 87:9665–9669.
Goodman, L. E., Perou, C. M., Fujiyama, A., and Tamanoi, F. (1988), *Yeast* 4:271–281.
Hancock, J. F., Paterson, H., and Marshall, C. J. (1990) *Cell* 63:133–139.
Hancock, J. F., Magee, A. I., Childs, J. E., and Marshall, C. J. (1989) *Cell* 57:1167–1177.
Harlow, E. & Lane, D. (1988), In: Antibodies: A Laboratory Manual. Cold Spring Harbour Laboratory Press, NY, pp. 82–83.
He, B., Chen, P., Chen, S. Y., Vancura, K. L., Michaelis, S., and Powers, S. (1991), *Proc. Natl. Acad. Sci. USA,* 88:11373–11377.
James, G. L., Goldstein, J. L., Brown, M. S., Rawson, T. E., Somers, T. C., McDowell, R. S., Crowley, C. W., Lucas, B. K., Levinson, A. D., and Marsters, J. C., Jr. (1993) *Science* 260:1937–1942.
James, G. L., Brown, M. S., Cobb, M. H., and Goldstein, J. L. (1994) *J. Biol. Chem.* 269:27705–27714.
Kawata, M., Farnsworth, C. C., Yoshida, Y., Gelb, M. H., Glomset, J. A., and Takai, Y. (1990) *Proc. Natl. Acad. Sci. USA* 87:8960–8964.
Khosravi-Far, R., Lutz, R. J., Cox, A. D., Clark, R., Bourne, J. R., Sinensky, M., Balch, W. E., Buss, J. E., and Der, C. J. (1991), *Proc. Natl. Acad. Sci. USA,* 88:6264–6268.

King, H. L. and Rilling, H. C. (1977), *Biochemistry,* 16:3815–3819.
Kohl, N. E., Wilson, F. R., Mosser, S. D., Giuliani, E., deSolms, S. J., Conner, M. W., Anthony, N. J., Holtz, W. J., Gomez, R. P., Lee, T.-J., Smith, R. L., Graham, S. L., Hartman, G. D., Gibbs, J. B., and Oliff, A. (1994) *Proc. Natl. Acad. Sci. USA* 91:9141–9145.
Kohl, N. E., Diehl, R. E., Schaber, M. D., Rands, E., Soderman, D. D., He, B., Moores, S. L., Pompliano, D. L., Ferro-Novick, S., Powers, S., Thomas, K. A., Gibbs, J. B. (1991), *J. Biol. Chem.,* 266:18884–18888.
Kozak, M. (1984) *Nucleic Acids Res.* 12:857–872.
Kyte, J., & Doolittle, (1982) *J. Molec. Biol.,* 157:105–132.
Laemmli, U. K. (1970), *Nature,* 227:680–685.
Lee, C. C., et al. (1988), *Science,* 239:1288–1291.
Lehrman, M. A., et al. (1987), *J. Biol. Chem.,* 262:3354–3361.
Lipscomb, W. N. (1974), *Tetrahedron,* 30:1725–1732.
Lowry, O. H., et al. (1951), *J. Biol. Chem.,* 193:265–275.
McCoy et al., "Human Colon Carcinoma Ki-ras2 Oncogene and its Corresponding Proto-Oncogene," *Molecular and Cellular Biology,* 4(8):1577–1582, 1984.
McGrath et al., "Structure and organization of the human Ki-ras proto-oncogene and a related processed pseudogene," *Nature,* 304:501, 1983.
Maxam, A. M., et al. (1980), *Methods Enzymol,* 65:499–560.
Moomaw, J. F. and Casey, P. J. (1992) *J. Biol. Chem.* 267:17438–17443.
Moores, S. L., Schaber, M. D., Mosser, S. D., Rands, E., O'Hara, M. B., Garsky, V. M., Marshall, M. S., Pompliano, D. L., and Gibbs, J. B. (1991) *J. Biol. Chem.* 266:14603–14610.
Mumby, S. M., et al. (1990), *Proc. Natl. Acad. Sci. USA,* 87:5873–5877.
O'Reilly, D. R., Miller, L. K., and Luckow, V. A. (1992) "Baculovirus Expression Vectors A Laboratory Manual," W. H. Freeman and Co., New York.
Ohya, Y., Goebl, M., Goodman, L. E., Petersen-Bjørn, S., Friesen, J. D., Tamanoi, F., and Anraku, Y. (1991), *J. Biol. Chem.,* 266:12356–12360.
Petrillo, E. W. Jr., Ondetti, M. A. (1982), *Medicinal Res. Rev.,* 2:1–41.
Pizon, V., Lerosey, I., Chardin, P., and Tavitian, A. (1988) *Nucl. Acids Res.* 16:7719.
Pompliano, D. L., Rands, E., Schaber, M. D., Mosser, S. D., Anthony, N. J., and Gibbs, J. B. (1992) *Biochem.* 31:3800–3807.
Pompliano, D. L., Schaber, M. D., Mosser, S. D., Omer, C. A., Shafer, J. A. and Gibbs, J. B. (1993) *Biochem.* 32:8341–8347.
Prendergast, G. C., Davide, J. P., deSolms, S. J., Giuliani, E. A., Graham, S. L., Gibbs, J. B., Oliff, A., and Kohl, N. E. (1994) *Molec. Cell. Biol.* 14:4193–4202.
Reiss, Y., Seabra, M. C., Armstrong, S. A., Slaughter, C. A., Goldstein, J. L., and Brown, M. S. (1991), *J. Biol. Chem.,* 266:10672–10677.
Reiss, Y., Stradley, S. J., Gierasch, L. M., Brown, M. S., and Goldstein, J. L. (1991) *Proc. Natl. Acad. Sci. USA* 88:732–736.
Reiss, Y., Goldstein, J. L., Seabra, M. C., Casey, P. J., and Brown, M. S. (1990) *Cell* 62:81–88.
Reiss, Y., Brown, M. S., and Goldstein, J. L. (1992) *J. Biol. Chem.* 267:6403–6408.
Rilling, H. C. (1985), *Meth. Enzymol.,* 110:145–152.
Rilling, H. C., Breunger, E., Epstein, W. W., and Crain, P. F. (1990), *Science,* 247:318–320.
Robishaw, J. D., et al. (1989), *J. Biol. Chem.,* 264:15758–15761.

Rossi, G., Jiang, Y., Newman, A. P., and Ferro-Novick, S. (1991), *Nature,* 351:158–161.

Saiki, R. K. et al. (1988), *Science,* 239:487–491.

Sambrook, J., et al. (1989), "Molecular Cloning: A Laboratory Manual," Cold Springs Harbor Laboratory, Cold Springs Harbor, N.Y.

Sanger, F., et al. (1977), *Proc. Natl. Acad. Sci. USA,* 74:5463–5467.

Sanger, F., Coulson, A. R., Barrell, B. G., Smith, A. J. H. and Roe, B. A. (1980), *J. Molec. Biol.* 143:161–178.

Schafer, W. R., Trueblood, C. E., Yang, C-C., Mayer, M. P., Rosenberg, S., Poulter, C. D., Kim, S-H., and Rine, J. (1990), *Science,* 249:1133–1139.

Schafer, W. R. and Rine, J. (1992) *Ann. Rev. Genet.* 30:209–237.

Seabra, M. C., Reiss, Y., Casey, P. J., Brown, M. S., and Goldstein, J. L. (1991) *Cell* 65:429–434.

Seabra, M. C., Brown, M. S., and Goldstein, J. L. (1993) *Science* 259:377–381.

Shimizu et al., "Structure of the Ki-ras gene of the human lung carcinoma cell line Calu-1," *Nature,* 304:497, 1983.

Stewart, J. M. et al. (1984), "Solid Phase Peptide Synthesis," 2nd ed., Pierce Chemical Co., Rockford, Ill.

Tabor, S., et al. (1987), *Proc. Natl. Acad. Sci. USA,* 84:4767–4771.

Tamanoi, F. (1993) *TIBS* 18:349–353.

Trueblood, C. E., Ohya, Y., and Rine, J. (1993) *Molec. Cell. Biol.* 13:4260–4275.

Yamamoto, F. et al. (1985), *Prog. Med. Virol.,* 32:101–114.

Yamane, H. K., et al. (1990), *Proc. Natl. Acad. Sci. USA,* 87:5868–5872.

Yokoyama, K., Goodwin, G. W., Ghomashchi, F., Glomset, J. A., and Gelb, M. H. (1991) *Proc. Natl. Acad. Sci. USA* 88:5302–5306.

Yokoyama, K. and Gelb, M. H. (1993) *J. Biol. Chem.* 268:4055–4060.

Zhang, F. L., Diehl, R. E., Kohl, N. E., Gibbs, J. B., Giros, B., Casey, P. J., and Omer, C. A. (1994) *J. Biol. Chem.* 269:3175–3180.

What is claimed is:

1. A method for assaying for the presence of farnesyl protein transferase activity in an enzyme composition, comprising determining the ability of said enzyme composition to catalyze the transfer of a farnesyl moiety to a K-RasB protein or K-RasB peptide fragment having farnesyl acceptor activity.

2. The method of claim 1, wherein the ability of said enzyme composition to catalyze the transfer of a farnesyl moiety to a K-RasB protein or K-RasB peptide fragment having farnesyl acceptor activity is determined by a method comprising the steps of:

(a) admixing said enzyme composition with a substrate composition comprising a K-RasB protein, or K-RasB peptide fragment having farnesyl acceptor activity, and a farnesyl pyrophosphate compound having a labeled farnesyl moiety; and (b) evaluating the ability of said enzyme composition to transfer said labeled farnesyl moiety to said K-RasB protein or K-RasB peptide fragment having farnesyl acceptor activity.

3. The method of claim 2, wherein said substrate composition comprises a K-RasB protein.

4. The method of claim 2, wherein said substrate composition comprises a K-RasB peptide fragment having farnesyl acceptor activity.

5. The method of claim 2, wherein said farnesyl pyrophosphate compound has a radiolabeled farnesyl moiety.

6. A method for determining whether a candidate substance has the ability to inhibit a farnesyl protein transferase enzyme, the method comprising the steps of:

(a) obtaining an enzyme composition comprising a farnesyl protein transferase enzyme;

(b) obtaining a substrate composition comprising a K-RasB protein or K-RasB peptide fragment having farnesyl acceptor activity;

(c) admixing said enzyme composition with said substrate composition, a farnesyl pyrophosphate and a candidate substance; and (d) determining the ability of the farnesyl protein transferase enzyme to transfer a farnesyl moiety to the K-RasB protein or K-RasB peptide fragment having farnesyl acceptor activity in the presence of the candidate substance and in the absence of the candidate substance.

7. The method of claim 6, wherein said enzyme composition is a native enzyme composition obtained by purification from natural sources.

8. The method of claim 6, wherein said enzyme composition is a recombinant enzyme composition obtained by recombinant expression.

9. The method of claim 6, wherein said substrate composition comprises a K-RasB protein.

10. The method of claim 6, wherein said substrate composition comprises a K-RasB peptide fragment having farnesyl acceptor activity.

11. The method of claim 6, wherein said substrate composition is obtained by purification from natural sources.

12. The method of claim 6, wherein said substrate composition is obtained by recombinant expression.

13. The method of claim 6, wherein the farnesyl moiety of said farnesyl pyrophosphate is labeled.

14. The method of claim 13, wherein the farnesyl moiety of said farnesyl pyrophosphate is radiolabeled.

15. A method for inhibiting a farnesyl protein transferase enzyme, comprising contacting the enzyme with an effective amount of a farnesyl protein transferase inhibitor substance identified by the method of claim 6.

16. A method of inhibiting the attachment of a farnesyl moiety to a K-RasB protein in a cell, comprising transferring into said cell an effective amount of a farnesyl protein transferase enzyme inhibitor, the inhibitor identified by a method comprising the steps of:

(a) admixing a farnesyl protein transferase enzyme composition with a K-RasB protein or K-RasB peptide fragment having farnesyl acceptor activity substrate composition, a farnesyl pyrophosphate and a candidate inhibitory substance; and (b) determining the ability of the farnesyl protein transferase enzyme to transfer a farnesyl moiety to the K-RasB protein or K-RasB peptide fragment having farnesyl acceptor activity in the presence of the candidate inhibitory substance and in the absence of the candidate inhibitory substance.

17. A method for inhibiting a farnesyl protein transferase enzyme, comprising contacting the enzyme with an effective amount of a farnesyl protein transferase inhibitor identified by a process comprising the steps of:

(a) obtaining an enzyme composition comprising a farnesyl protein transferase enzyme that is capable of transferring a farnesyl moiety to a farnesyl acceptor substance comprising a K-RasB protein or K-RasB peptide fragment having farnesyl acceptor activity;

(b) admixing a candidate substance with the enzyme composition and farnesyl pyrophosphate; and (c) identifying a farnesyl protein transferase inhibitor by selecting a candidate inhibitor substance that inhibits the ability of the farnesyl protein transferase enzyme to transfer a farnesyl moiety to the farnesyl acceptor substance.

18. A method of providing a farnesyl protein transferase inhibitor comprising:

(a) obtaining a test composition comprising a compound suspected of being a farnesyl protein transferase inhibitor;

(b) obtaining an enzyme composition comprising a farnesyl protein transferase enzyme that is capable of transferring a farnesyl moiety to a farnesyl acceptor substance wherein the farnesyl protein transferase enzyme comprises a recombinant farnesyl protein transferase enzyme obtained by recombinant expression;

(c) admixing farnesyl pyrophosphate, the enzyme composition and the farnesyl acceptor substance with the test composition;

(d) determining the ability of the enzyme composition to transfer a farnesyl moiety to the farnesyl acceptor substance in the presence of the test composition, wherein the ability of the test composition to inhibit the transfer of the farnesyl moiety to the farnesyl acceptor substance confirms the identity of the test composition to be a farnesyl protein transferase inhibitor; and (e) providing the identified farnesyl protein transferase inhibitor.

19. The method of claim 18, wherein the farnesyl acceptor substance comprises a peptide of at least 4 amino acids in length that includes a carboxy terminal amino acid sequence of —C—A—A—X, wherein:

C=cysteine;

A=an aliphatic or hydroxy amino acid; and

X=any amino acid.

20. The method of claim 19, wherein the farnesyl acceptor substance comprises a peptide of at least 6 amino acids in length that includes a carboxy terminal amino acid sequence of Thr Lys Cys Val Ile Met.

21. The method of claim 18, wherein the farnesyl acceptor substance comprises a $p21^{ras}$ protein.

22. The method of claim 21, wherein the $p21^{ras}$ protein comprises a K-RasB protein.

23. The method of claim 18, wherein the farnesyl pyrophosphate comprises a labeled farnesyl moiety.

24. The method of claim 23, wherein the farnesyl pyrophosphate comprises a radiolabeled farnesyl moiety.

25. The method of claim 18, wherein the farnesyl protein transferase enzyme comprises a farnesyl protein transferase enzyme characterized as:

(a) catalyzing the transfer of all-trans farnesol to a protein or peptide having a carboxy terminal farnesyl acceptor moiety;

(b) binding to an affinity chromatography medium that comprises a peptide of the amino acid sequence Thr Lys Cys Val Ile Met coupled to a matrix;

(c) exhibiting a molecular weight of between about 70,000 Da and about 100,000 Da upon gel filtration chromatography, and comprising to two different subunits, each exhibiting a molecular weight of approximately 45,000 Da to 50,000 Da upon SDS-PAGE;

(d) having a farnesyl protein transferase activity that is capable of being inhibited by a peptide having the sequence Thr Lys Cys Val Ile Met; Cys Val Ile Met; or Lys Lys Ser Lys Thr Lys Cys Val Ile Met; and (e) exhibiting a farnesyl protein transferase specific activity of between about 5 and about 600,000 units/mg protein.

26. The method of claim 25, wherein the farnesyl protein transferase enzyme exhibits a farnesyl protein transferase specific activity of between about 500 and about 600,000 units/mg protein.

27. The method of claim 18, wherein the enzyme composition comprises a farnesyl protein transferase enzyme purified by a process that includes the steps of:

(a) preparing a cellular extract that includes the enzyme;

(b) subjecting the extract to affinity chromatography on an affinity chromatography medium to bind the enzyme thereto, the medium comprised of a farnesyl protein transferase binding peptide coupled to a suitable matrix;

(c) washing the medium to remove impurities; and (d) eluting the enzyme from the washed medium.

28. The method of claim 27, wherein said farnesyl protein transferase binding peptide comprises a peptide of at least 4 amino acids in length that includes a carboxy terminal sequence of —C—A—A—X, wherein:

C=cysteine;

A=an aliphatic or hydroxy amino acid; and

X=any amino acid.

29. The method of claim 28, wherein said farnesyl protein transferase binding peptide comprises the sequence Thr Lys Cys Val Ile Met.

30. A method of providing a farnesyl protein transferase inhibitor comprising:

(a) obtaining an enzyme composition comprising an enzyme suspected of having farnesyl protein transferase inhibitor activity;

(b) admixing the enzyme composition, farnesyl pyrophosphate, a farnesyl protein transferase enzyme that is capable of transferring a farnesyl moiety to a farnesyl acceptor substance, and the farnesyl acceptor substance wherein the farnesyl protein transferase enzyme is further defined as exhibiting a farnesyl transferase specific activity of between about 500 and about 600,000 units/mg protein;

(c) determining the ability of the farnesyl protein transferase enzyme to transfer a farnesyl moiety to the farnesyl acceptor substance in the presence and absence of the enzyme composition, wherein the ability of the enzyme composition to inhibit the transfer of the farnesyl moiety to the farnesyl acceptor substance confirms the identity of the enzyme composition to be a farnesyl protein transferase inhibitor; and (d) providing the identified farnesyl protein transferase inhibitor.

31. A method of providing a candidate substance having the ability to inhibit a farnesyl protein transferase enzyme comprising:

(a) obtaining an enzyme composition comprising a farnesyl protein transferase enzyme that is capable of a farnesyl moiety to a farnesyl acceptor substance;

(b) admixing a candidate substance with the enzyme composition and farnesyl pyrophosphate, wherein the enzyme composition comprises an enzyme characterized as follows:

(i) catalyzing the transfer of all-trans farnesol to a protein or peptide having a carboxy terminal farnesyl acceptor moiety;

(ii) binding to an affinity chromatography medium that comprises peptide of the amino acid sequence Thr Lys Cys Val Ile Met coupled to a matrix;

(iii) exhibiting a molecular weight of between about 70,000 Da and about 100,000 Da upon gel filtration chromatography, and comprising two different subunits, each exhibiting a molecular weight of approximately 45,000 Da to 50,000 Da upon SDS-PAGE;

(iv) having a farnesyl protein transferase activity that is capable of being inhibited by a peptide having the sequence Thr Lys Cys Val Ile Met; Cys Val Ile Met; or Lys Lys Ser Lys Thr Lys Cys Val Ile Met; and (v) exhibiting a farnesyl protein transferase specific activity of between about 5 and about 600,000 units/mg protein;

(c) comparing the ability of the farnesyl protein transferase enzyme to transfer a farnesyl moiety to a farnesyl acceptor substance in the presence of the candidate substance to the ability of the farnesyl protein transferase enzyme to transfer a farnesyl moiety to the substrate in the absence of the candidate substance; and (d) the candidate substance that is determined to have the ability to inhibit the farnesyl protein transferase enzyme.

32. The method of claim 31, wherein the enzyme is further defined as exhibiting a farnesyl transferase specific activity of between about 500 and about 600,000 units/mg protein.

33. The method of claim 32, wherein the farnesyl protein transferase enzyme is prepared by recombinant means.

34. The method of claim 32, wherein the farnesyl protein transferase enzyme comprises a native farnesyl protein transferase enzyme obtained by purification from natural sources.

* * * * *

UNITED STATES PATENT AND TRADEMARK OFFICE
CERTIFICATE OF CORRECTION

PATENT NO. : 5,962,243

DATED : October 5, 1999

INVENTOR(S) : Michael S. Brown, Joseph L. Goldstein, Guy L. James, Yuval Reiss,

It is certified that error appears in the above-identified patent and that said Letters Patent is hereby corrected as shown below:

Title page, item [75], after "Tex.", insert --and Yuval Reiss of Gival Shmuel, Israel-- therefor.

In claim 19, column 115, line 36, delete "A-X", and insert --$A$-$A$-$X$-- therefor.
In claim 19, column 115, line 38, delete "A", and insert --$A$-- therefor.
In claim 19, column 115, line 39, delete "X", and insert --$X$-- therefor.
In claim 28, column 116, line 27, delete "A-A-X", and insert --$A$-$A$-$X$-- therefor.
In claim 28, column 115, line 28, delete "A", and insert --$A$-- therefor.
In claim 28, column 115, line 29, delete "X", and insert --$X$-- therefor.

Signed and Sealed this

Eighth Day of August, 2000

Attest:

Q. TODD DICKINSON

*Attesting Officer*

*Director of Patents and Trademarks*